US009353400B2

(12) United States Patent
Meidlinger

(10) Patent No.: US 9,353,400 B2
(45) Date of Patent: May 31, 2016

(54) METHODS FOR ANALYSES OF CYANOBACTERIAL RESTRICTION ENDONUCLEASES

(71) Applicant: Algenol Biofuels Inc., Fort Myers, FL (US)

(72) Inventor: Marc Meidlinger, Schönefeld (DE)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 14/144,361

(22) Filed: Dec. 30, 2013

(65) Prior Publication Data
US 2015/0184221 A1 Jul. 2, 2015

(51) Int. Cl.
C12Q 1/68 (2006.01)
C12Q 1/44 (2006.01)

(52) U.S. Cl.
CPC ............ *C12Q 1/44* (2013.01); *G01N 2333/922* (2013.01)

(58) Field of Classification Search
None
See application file for complete search history.

(56) References Cited

PUBLICATIONS

Lyra et al., J. Appl. Microbiol., 89:979-991, 2000.*
Whitehead et al., Arch. Microbiol. 141:70-74, 1985.*
Heidorn et. al., "Synthetic Biology in Cyanobacteria: Engineering and Analyzing Novel Functions", Methods in Enzymology, vol. 497 (2011), pp. 539-579.
Ruffing et al., "Physiological effects of free fatty acid production in genetically engineered Synechococcus elongatus PCC 7942", Biotech. Bioeng., vol. 109, No. 9 (2012), pp. 2190-2199.
Soper et al., "Identification of a nuclease and host restriction-modification in the unicellular, aerobic nitrogen-fixing cyanobacterium *Cyanothece* sp.", J. Bacteriology, vol. 176, No. 17 (1994), pp. 5565-5570.
Elhai et al., "P. Reduction of conjugal transfer efficiency by three restriction activities of *Anabaena* sp. Strain PCC7120", J. Bacteriology, vol. 179, No. 6 (1997), pp. 1998-2005.
Shibata, "Oligonucleotide-templated reactions for sensing nucleic acids", Molecules, vol. 17, No. 3 (2012), pp. 2446-2463.
Houmard et al., "Cyanobacterial genetic tools: current status.", Methods Enzymol., vol. 167 (1988), pp. 808-847.
Koksharova et al., "Genetic tools for cyanobacteria", Appl. Microbiol. Biotechnol., vol. 58 (2002), pp. 123-137.
Murray et al., "Isolation and Characterization of Two Sequence-Specific Endonucleases from Anabaena variabilis", Biochem. J., vol. 159, No. 2 (1976), pp. 317-322.
Padhy et al., "Restriction analysis and quantitative estimation of methylated bases of filamentous and unicellular cyanobacterial DNAs", J. Bacteriol., vol. 170, No. 4 (1988), pp. 1934-1939.
Reaston et al., "Nostoc PCC7524, a cyanobacterium which contains five sequence-specific deoxyribonucleases", Gene, vol. 20 (1982), pp. 103-110.
Zhao et al., "Genome-wide analysis of restriction-modification system in unicellular and filamentous cyanobacteria", Physiol. Genomics., vol. 24, No. 3 (2006), pp. 181-190.
Scharnagl et al., "The Cyanobacterium *Synechocystis* sp. Strain PCC 6803 Expresses a DNA Methyltransferase Specific for the Recognition Sequence of the Restriction Endonuclease PvuI", J. Bacteriology, vol. 180, No. 6 (1998), pp. 4116-4122.
Miyake et al., "Isolation and identification of restriction endonuclease, SeII from a cyanobacterium, Synechococcus elongatus", Nucleic Acids Research, vol. 20, No. 10 (1992), p. 2605.

* cited by examiner

*Primary Examiner* — Nancy T Vogel
(74) *Attorney, Agent, or Firm* — Lawrence Ebert; Sam Barkley; David Lorenz

(57) ABSTRACT

Methods are provided for analyses of restriction endonucleases.

7 Claims, 20 Drawing Sheets

| Enzyme | General recognition sequence | Specific ROligo realization | Enzyme | General recognition sequence | Specific ROligo realization |
|---|---|---|---|---|---|
| | | | R.MboII | GAAGA | |
| R.AcyI | GRCGYC | GACGCC | R.MstI | TGCGCA | |
| R.AflI | CTTAAG | | R.NcoI | CCATGG | |
| R.AflIII | ACRYGT | ACGTGT | R.NdeI | CATATG | |
| R.AhaIII | TTTAAA | | R.NspBII | CMGCKG | T³ CAGCGG |
| R.ApaI | GGGCCC | | R.NspI | RCATGY | ACATGC |
| R.AsuI | GGNCC | T¹ GGCCC | R.Ppu21I | YACGTR | TACGTG |
| R.AsuII | TTCGAA | | R.PstI | CTGCAG | T³ CTGCAG |
| R.AvaI | CYCGRG | CTCGGG | R.PvuI | CGATCG | |
| R.AvaII | GGWCC | GGACC | R.PvuII | CAGCTG | T CAGCTG |
| R.AvaIII | ATGCAT | | R.RsaI | GTAC | |
| R.AvrII | CCTAGG | | R.SacII | CCGCGG | |
| R.BamHI | GGATCC | | R.SalI | GTCGAC | GTCGAC T⁴ |
| R.BglII | AGATCT | | R.SauI | CCTNAGG | CCTAAGG |
| R.BlpI | GCTNAGC | GCTAAGC | R.ScaI | AGTACT | |
| R.BspMII | TCCGGA | | R.SceI | CGCG | |
| R.BstEII | GGTNACC | GGTAACC | R.SduI | GDGCHC | GAGCCC |
| R.BstXI | CCANNNNNNTGG | CCACCTTCCTGG | R.SphI | GCATGC | |
| R.Cfr10I | RCCGGY | ACCGGC | R.SplI | CGTACG | |
| R.Eco47III | AGCGCT | | R.TaqI | TCGA | |
| R.EcoRI | GAATTC | | | | |
| R.HaeII | RGCGCY | AGCGCC | R.AhaI * | CCSGG | |
| R.HaeIII | GGCC | T² GGCC | R.SecI * | CCNNGG | |
| R.HgiCI | GGYRCC | GGCACC | R.SecII * | CCGG | |

FIG. 2

| Primer no. | SEQ ID NO: | Purpose | Sequence 5'->3' |
|---|---|---|---|
| 472 | 5 | ROligo left arm forward non-K230-derived | CTCCATCTCCAGTCCTCAGTTCAG |
| 473 | 6 | ROligo left arm reverse non-K230-derived | GTGTGACGAAATTGGAAGCTGC |
| 474 | 7 | ROligo left arm forward | CTCCATCTCCAGTCCTCAGTTCAGTCACGTTACTTTCTGAAAAAGCCGG |
| 475 | 8 | ROligo right arm reverse | GTGTGACGAAATTGGAAGCTGGTCCTAAGTGTTTAGCATGTTACGGC |
| 476 | 9 | ROligo.AcyI left arm reverse | GTTATGCCCGGTTACAGTCTGTAACGCGTCAGTTTTCAGCCACTCCAAACGGC |
| 481 | 10 | ROligo.AcyI right arm forward | GCCGTTTGGAGTGGCTGAAAACTGACGCGTTACAGACTGTAACCGGGCATAAC |
| 477 | 11 | ROligo.BipI left arm reverse | GTTATGCCCGGTTACAGTCTGTAACGCTAGCCAGTTTTCAGCCACTCCAAACGGC |
| 478 | 12 | ROligo.BipI right arm forward | GCCGTTTGGAGTGGCTGAAAACTGGCTAAGCGTTACAGACTGTAACCGGGCATAAC |
| 479 | 13 | ROligo.MstI left arm reverse | GTTATGCCCGGTTACAGTCTGTAACTGCGCACAGTTTTCAGCCACTCCAAACGGC |
| 480 | 14 | ROligo.MstI right arm forward | GCCGTTTGGAGTGGCTGAAAACTGTGCGCAGTTACAGACTGTAACCGGGCATAAC |
| 504 | 15 | ROligo.AvaI left arm reverse | GGTTACAGTCTGTAACCTCGGGCAGTTTTCAGCCACTCCAAACG |
| 505 | 16 | ROligo.AvaI right arm forward | GAGTGGCTGAAAACTGCCCGAGGTTACAGACTGTAACCGGGCA |
| 506 | 17 | ROligo.SphI left arm reverse | GGTTACAGTCTGTAAGCATGCCAGTTTCAGCCACTCCAAACG |
| 507 | 18 | ROligo.SphI right arm forward | GAGTGGCTGAAAACTGGCATGCGTTACAGACTGTAACCGGGCA |
| 508 | 19 | ROligo.AvaII left arm reverse | CGGTTACAGTCTGTAACGGTCCAGTTTCAGCCACTCCAAACG |
| 509 | 20 | ROligo.AvaII right arm forward | GGAGTGGCTGAAAACTGGACCGTTACAGACTGTAACCGGGCA |
| 540 | 21 | ROligo.AsuI left arm reverse | GGTTACAGTCTGTACCGGGCCACAGTTTTCAGCCACTCCAAACG |
| 541 | 22 | ROligo.AsuI right arm forward | GAGTGGCTGAAAACTGTGGCCCGGTACAGACTGTAACCGGGCA |
| 542 | 23 | ROligo.AsuII left arm reverse | GGTTACAGTCTGTAACTTCGAACAGTTTTCAGCCACTCCAAACG |
| 543 | 24 | ROligo.AsuII right arm forward | GAGTGGCTGAAAACTGTTCGAAGTTACAGACTGTAACCGGGCA |
| 544 | 25 | ROligo.AvaIII left arm reverse | GGTTACAGTCTGTAACATGCATCAGTTTCAGCCACTCCAAACG |
| 545 | 26 | ROligo.AvaIII right arm forward | GAGTGGCTGAAAACTGATGCATGTTACAGACTGTAACCGGGCA |
| 546 | 27 | ROligo.BamHI left arm reverse | GGTTACAGTCTGTAACGGATCCAGTTTTCAGCCACTCCAAACG |
| 547 | 28 | ROligo.BamHI right arm forward | GAGTGGCTGAAAACTGGATCCGTTACAGACTGTAACCGGGCA |
| 548 | 29 | ROligo.BstEII left arm reverse | GTTACAGTCTGTAACGGTTACCCAGTTTCAGCCACTCCAAACG |
| 549 | 30 | ROligo.BstEII right arm forward | AGTGGCTGAAAACTGGGTAACCGTTACAGACTGTAACCGGGCA |
| 552 | 31 | ROligo.NspI left arm reverse | GGTTACAGTCTGTAACGCATGTCAGTTTCAGCCACTCCAAACG |
| 553 | 32 | ROligo.NspI right arm forward | GAGTGGCTGAAAACTGACATGCGTTACAGACTGTAACCGGGCA |
| 554 | 33 | ROligo.PstI left arm reverse | GTTACAGTCTGTAACCTGCAGACAGTTTCAGCCACTCCAAACG |
| 555 | 34 | ROligo.PstI right arm forward | AGTGGCTGAAAACTGTCTGCAGGTTACAGACTGTAACCGGGCA |
| 556 | 35 | ROligo.PvuII left arm reverse | GTTACAGTCTGTAACCAGCTGACAGTTTCAGCCACTCCAAACG |
| 557 | 36 | ROligo.PvuII right arm forward | AGTGGCTGAAAACTGTCAGCTGGTTACAGACTGTAACCGGGCA |
| 558 | 37 | ROligo.RsaI left arm reverse | CGGTTACAGTCTGTAACGTACCAGTTTCAGCCACTCCAAACG |
| 559 | 38 | ROligo.RsaI right arm forward | TGGAGTGGCTGAAAACTGGTACGTTACAGACTGTAACCGCGCA |
| 560 | 39 | ROligo.ScaI left arm reverse | GGTTACAGTCTGTAACAGTACTCAGTTTTCAGCCACTCCAAACG |
| 561 | 40 | ROligo.ScaI right arm forward | GAGTGGCTGAAAACTGAGTACTGTTACAGACTGTAACCGGGCA |
| 562 | 41 | ROligo.SduI left arm reverse | GGTTACAGTCTGTAACCGCGTCCAGTTTTCAGCCACTCCAAACG |
| 563 | 42 | ROligo.SduI right arm forward | GAGTGGCTGAAAACTGGAGCGCGGTTACAGACTGTAACCGGGCA |
| 564 | 43 | ROligo.TaqI left arm reverse | CCGGTTACAGTCTGTAAGTCGACAGTTTCAGCCACTCCAAACG |
| 565 | 44 | ROligo.TaqI right arm forward | TGGAGTGGCTGAAAACTGTCGAGTTACAGACTGTAACCGGGCA |
| 566 | 45 | ROligo.NspBII left arm reverse | GTTACAGTCTGTAACCCGCGGCGTTTTCAGCCACTCCAAACG |
| 567 | 46 | ROligo.NspBII right arm forward | AGTGGCTGAAAACTGTCAGCGCGGTTACAGACTGTAACCGGGCA |
| 577 | 47 | ROligo.AflII left arm reverse | GGTTACAGTCTGTAACCTTAAGCAGTTTTCAGCCACTCCAAACG-3' |

FIG. 3

| 578 | 48 | ROligo.AflII right arm forward | GAGTGGCTGAAAACTGCTTAAGGTTACAGACTGTAACCGGGGA-3' |
|-----|----|-------------------------------|------------------------------------------------|
| 579 | 49 | ROligo.AflIII left arm reverse | GGTTACAGTCTGTAACACGTCAGTTTTCAGCCACTCCAAACG-3' |
| 580 | 50 | ROligo.AflIII right arm forward | GAGTGGCTGAAAACTGACGTGTTACAGACTGTAACCGGGGA-3' |
| 583 | 51 | ROligo.ApaI left arm reverse | GGTTACAGTCTGTAACGGGCCCAGTTTTCAGCCACTCCAAACG-3' |
| 584 | 52 | ROligo.ApaI right arm forward | GAGTGGCTGAAAACTGGGCCCGTTACAGACTGTAACCGGGGA-3' |
| 585 | 53 | ROligo.AvrII left arm reverse | GGTTACAGTCTGTAACCCTAGGCAGTTTTCAGCCACTCCAAACG-3' |
| 586 | 54 | ROligo.AvrII right arm forward | GAGTGGCTGAAAACTGCCTAGGGTTACAGACTGTAACCGGGGA-3' |
| 587 | 55 | ROligo.BglII left arm reverse | GGTTACAGTCTGTAACAGATCTCAGTTTTCAGCCACTCCAAACG-3' |
| 588 | 56 | ROligo.BglII right arm forward | GAGTGGCTGAAAACTGAGATCTGTTACAGACTGTAACCGCGCA-3' |
| 589 | 57 | ROligo.HaeIII left arm reverse | CGGTTACAGTCTGTAACGGCCACAGTTTTCAGCCACTCCAAACG-3' |
| 590 | 58 | ROligo.HaeIII right arm forward | GGACTGGCTGAAAACTGTGGCCGTTACAGACTGTAACCGGGCA-3' |
| 591 | 59 | ROligo.NcoI left arm reverse | GGTTACAGTCTGTAACCCATGGCAGTTTTCAGCCACTCCAAACG-3' |
| 592 | 60 | ROligo.NcoI right arm forward | GAGTGGCTGAAAACTGCCATGGGTTACAGACTGTAACCGGGGA-3' |
| 593 | 61 | ROligo.SalI left arm reverse | GTTACAGTCTGTAACAGTCGACCAGTTTTCAGCCACTCCAAACG-3' |
| 594 | 62 | ROligo.SalI right arm forward | ACTCGCTGAAAACTGCTCGACTGTTACAGACTGTAACCGCGCA-3' |

Combining the digested ROligos

ROligos cut in extract ↑
___
ROligos not cut in extract ↓

| | HaeIII | SphI | | Combination HaeIII + SphI |
|---|---|---|---|---|
| ROligo.ASUI | | | | |
| ROligo.HAEIII | ■ | | | ■ |
| ROligo.SPHI | | ■ | | |
| ROligo.ACYI | | | | |
| ROligo.ASUII | | | | |
| ROligo.AVAI | | | | |
| ROligo.AVAII | | | | |
| ROligo.AVAIII | | | | |
| ROligo.BAMHI | | | | |
| ROligo.BLPI | | | | |
| ROligo.BSTEII | | | | |
| ROligo.MSTI | | | | |
| ROligo.NSPBII | | | | |
| ROligo.NSPI | | | | |
| ROligo.PSTI | | | | |
| ROligo.PVUII | | | | |
| ROligo.RSAI | | | | |
| ROligo.SCAI | | | | |
| ROligo.SDUI | | | | |
| ROligo.TAQI | | | | |

FIG. 14

| Strain | RM systems predicted | RENs detected in extract | Protected by methylation |
|---|---|---|---|
| A first *Lyngbya* strain | R.PvuII<br>R.SacII<br>R.NspI | R.PvuII / CAGCTG ##<br>not detected<br>not detected | blocked by commercial M.CviPI |
| A *Chlorogloeopsis* strain | R.BlpI<br>R.SphI<br>R.NspV | R.BlpI / GCTNAGC<br>R.SphI / GCATGC<br>not detected | blocked by commercial M.CviPI *<br>blocked by commercial M.CviPI * |
| A first *Cyanobacterium* strain | R.AcyI<br>R.AvaI<br>R.AvaIII<br>R.BstEII | R.AcyI / GRCGYC<br>R.AvaI / CYCGRG<br>not detected<br>not detected | blocked by commercial M.SssI<br>blocked by commercial M.SssI<br>blocked by M.AvaI(pRL528) |
| A first *Calothrix* strain | | R.AvaII / GGWCC<br>R.BglII / AGATCT | blocked by M.AvaII(pRL528) |
| A *Cyanothece* strain | R.SduI | no REN activity detected | |
| A *Geitlerinema* strain | | R.SauI / CCTNAGG | |
| A second *Cyanobacterium* strain | | R.AsuI / TTCGAA<br>R.HaeIII / GGCC | blocked by commercial M.SssI<br>blocked by commercial M.CviPI |
| A *Euhalothece* strain | | R.NarI / GGCGCC # | |
| A second *Lyngbya* strain | | R.AvaII / GGWCC<br>R.PvuII / CAGCTG | blocked by M.AvaII(pRL528)<br>blocked by commercial M.CviPI |
| A third *Cyanobacterium* strain | | R.BglII / AGATCT<br>R.HaeIII / GGCC<br>R.SphI / GCATGC | blocked by commercial M.CviPI<br>blocked by commercial M.CviPI * |
| A fourth *Cyanobacterium* strain | | R.EcoRV / GATATC # | |
| A *LPP* group strain | | R.BlpI / GCTNAGC<br>R.MstI / TGCGCA<br>R.PvuII / CAGCTG | blocked by commercial M.CviPI *<br>blocked by commercial M.CviPI *<br>blocked by commercial M.CviPI |
| A second *Nostoc* strain | R.AvaII<br>not predicted<br>not predicted | R.AvaII / GGWCC<br>R.MstI / TGCGCA<br>R.SalI / GTCGAC | blocked by M.AvaII(pRL528)<br>blocked by M.CviPI * and M.SssI<br>blocked by commercial M.SssI |
| A third *Lyngbya* strain | | R.HaeIII / GGCC | blocked by commercial M.CviPI |
| A second *Calothrix* strain | | R.AvaII / GGWCC | blocked by M.AvaII(pRL528) |

FIG. 15

SEQUENCE LISTING

```
<160> NUMBER OF SEQ ID NOS: 62

<210> SEQ ID NO 1
<211> LENGTH: 13729
<212> TYPE: DNA
<213> ORGANISM: Artificial Sequence
<220> FEATURE:
<223> OTHER INFORMATION: Plasmid K230 with restriction endonuclease free
      polynucleotide sequence from base pairs 7550 to 7926

<400> SEQUENCE: 1
gatccccggg taccagtaaa ggagaagaac tattcactgg agttgtccca attcttgttg      60
aattagatgg tgatgttaat gggcacaaat tttctgtcag tggagagggt gaaggtgatg     120
caacatacgg aaaacttacc cttaaattta tttgcactac tggaaaacta cctgttccat     180
ggccaacact tgtcactact ttcgcgtatg gtcttcaatg ctttgcgaga tacccagatc     240
atatgaaaca gcatgacttt ttcaagagtg ccatgcccga aggttatgta caggaaagaa     300
ctatattttt caaagatgac gggaactaca agacacgtgc tgaagtcaag tttgaaggtg     360 ataccctttgt taatagaatc gagttaaaag gtattgattt taaagaagat ggaaacattc     420
ttggacacaa attggaatac aactataact cacacaatgt atacatcatg gcagacaaac     480
aaaagaatgg aatcaaagtt aacttcaaaa ttagacacaa cattgaagat ggaagcgttc     540
aactagcaga ccattatcaa caaaatactc caattggcga tggccctgtc cttttaccag     600
acaaccatta cctgtccaca caatctgccc tttcgaaaga tcccaacgaa aagagagacc     660
acatggtcct tcttgagttt gtaacagctg ctgggattac acatggcatg gatgaactat     720
acaaataaga gctcgaattg atccttttg ataatctcat gaccaaaatc ccttaacgtg     780
agttttcgtt ccactgagcg tcagacccccg tagaaaagat caaaggatct tcttgagatc     840 cttttttct gcgcgtaatc tgctgcttgc aaacaaaaaa accaccgcta ccagcggtgg     900
tttgtttgcc ggatcaagag ctaccaactc tttttccgaa ggtaactggc ttcagcagag     960
cgcagatacc aaatactgtc cttctagtgt agccgtagtt aggccaccac ttcaagaact    1020
ctgtagcacc gcctacatac ctcgctctgc taatcctgtt accagtggct gctgccagtg    1080
gcgataagtc gtgtcttacc gggttggact caagacgata gttaccggat aaggcgcagc    1140
ggtcgggctg aacggggggt tcgtgcacac agcccagctt ggagcgaacg acctacaccg    1200
aactgagata cctacagcgt gagctatgag aaagcgccac gcttcccgaa gggagaaagg    1260
cggacaggta tccggtaagc ggcagggtcg gaacaggaga gcgcacgagg gagcttccag    1320
```

```
ggggaaacgc ctggtatctt tatagtcctg tcgggtttcg ccacctctga cttgagcgtc    1380 gattttgtg atgctcgtca gggggcgga gcctatggaa aaacgccagc aacgcggcct     1440
ttttacggtt cctggccttt tgctggcctt ttgctcacat gttctttcct gcgttatccc    1500
ctgattctgt ggataaccgt attaccgcct tgagtgagc tgataccgct cgccgcagcc    1560
gaacgaccga gcgcagcgag tcagtgagcg aggaagcgga agagcgcctg atgcggtatt    1620
ttctccttac gcatctgtgc ggtatttcac accgcatatg gtgcactctc agtacaatct    1680
gctctgatgc cgcatagtta agccagtata cactccgcta tcgctacgtg actgggtcat    1740
ggctgcgccc cgacacccgc caacaccgc tgacgcgccc tgacgggctt gtctgctccc    1800
ggcatccgct tacagacaag ctgtgaccgt ctccgggagc tgcatgtgtc agaggttttc    1860
accgtcatca ccgaaacgcg cgaggcagct gcggtaaagc tcatcagcgt ggtcgtgaag    1920
cgattcacag atgtctgcct gttcatccgc gtccagctcg ttgagtttct ccagaagcgt    1980
taatgtctgg cttctgataa agcgggcctg ccaccatacc cacgccgaaa caagcgctca    2040
tgagcccgaa gtggcgagcc cgatcttccc catcggtgat gtcggcgata taggcgccag    2100
caaccgcacc tgtggcgccg gtgatgcccg aagaactcca gcatgagatc cccgcgctgg    2160
aggatcatcc agccggcgtc ccggaaaacg attccgaagc ccaaccttc atagaaggcg    2220 gcggtggaat cgaaatctcg tgatggcagg ttgggcgtcg cttggtcggt catttcgaac    2280
cccagagtcc cgctcagaag aactcgtcaa gaaggcgata gaaggcgatg cgctgcgaat    2340
cgggagcggc gataccgtaa agcacgagga agcggtcagc ccattcgccg ccaagctctt    2400
cagcaatatc acgggtagcc aacgctatgt cctgatagcg gtccgccaca cccagccggc    2460
cacagtcgat gaatccagaa aagcggccat tttccaccat gatattcggc aagcaggcat    2520
cgccatgggt cacgacgaga tcatcgccgt cgggcatgcg cgccttgagc ctggcgaaca    2580
gttcggctgg cgcgagcccc tgatgctctt cgtccagatc atcctgatcg acaagaccgg    2640
cttccatccg agtacgtgct cgctcgatgc gatgtttcgc ttggtggtcg aatgggcagg    2700
tagccggatc aagcgtatgc agccgccgca ttgcatcagc catgatggat actttctcgg    2760
caggagcaag gtgagatgac aggagatcct gccccggcac ttcgcccaat agcagccagt    2820
cccttcccgc ttcagtgaca acgtcgagca cagctgcgca aggaacgccc gtcgtggcca    2880
gccacgatag ccgcgctgcc tcgtcctgca gttcattcag gcaccggac aggtcggtct    2940 tgacaaaaag aaccgggcgc cctgcgctg acagccggaa cacggcggca tcagagcagc    3000
cgattgtctg ttgtgcccag tcatagccga atagcctctc cacccaagcg gccggagaac    3060
ctgcgtgcaa tccatcttgt tcaatcatgc gaaacgatcc tcatcctgtc tcttgatcag    3120
atcttgatcc cctgcgccat cagatccttg gcggcaagaa agccatccag tttactttgc    3180
agggcttccc aaccttacca gagggcgccc cagctggcaa ttccggttcg cttgctgtcc    3240
ataaaaccgc ccagtctagc tatcgccatg taagcccact gcaagctacc tgctttctct    3300
ttgcgcttgc gttttccctt gtccagatag cccagtagct gacattcatc cggggtcagc    3360
accgtttctg cggactggct ttctacgtgt tccgcttcct ttagcagccc ttgcgccctg    3420
agtgcttgcg gcagcgtgaa gctttctctg agctgtaaca gcctgaccgc aacaaacgag    3480
aggatcgaga ccatccgctc cagattatcc ggctcctcca tgcgttgcct ctcggctcct    3540
gctccggttt tccatgcctt atggaactcc tcgatccgcc agcgatgggt ataaatgtcg    3600
atgacgcgca aggcttgggc tagcgactcg accggttcgc tggtcagcaa caaccatttc    3660
aacggggtct caccccttggg cgggttaatc tcctcggcca gcaccgcgtt gagcgtgata    3720
```

```
ttcccctgtt ttagcgtgat gcgcccactg cgcatagaaa ttgcatcaac gcatatagcg    3780
ctagcagcac gccatagtga ctggcgatgc tgtcggaatg gacgatatct agacttatat    3840
agacactaat atagacaata gtttatactg ctatctatac aagtatagac attatctaat    3900
catggcagac aaaactctag ccacttttcg tattgactcc gaagaatggg agtcttttaa    3960
aaaccttgct agttctgaaa gttccaacgc ctcagcactg ttaacagaat ttgttcgttg    4020
gtatttggca ggtaacaggt ttaatactcc cacttctcac actcccaccc atctagacac    4080
atccctcgaa cagcgtatag acaatattga acaacgtcta gataaagtca caactaataa    4140
tctagacaat atagatgaat ttatagacaa gcgtatagaa gataatctag caacacgtct    4200
agacaaactt caatcgcaac tggaggaact gcggggaaaa tcgaaagccc ggtagttcag    4260
gcagaaggac aagctaccgg gcaagacaga aagaatatag acaatagtat agacaatcta    4320
gacaaattgg aggcaacccg cgatcgcacc ctcaataagc taaaaatggg taggcagtca    4380
gccgccggga aagccatcga cgcgtttatc aaagagttgc tttcttcagg agacaacata    4440
agctgaagtt atcaaaattc tgtccttacg tcgaaagcct gattttaccg tgcaacgatt    4500
gataagcttg gctaaactag cactggcttt caacagaaag catacgaaga atcaatagat    4560
atagccacca attccacaaa atgcagataa cgtgtagagt attggaatgc ttaatctgta    4620
agggttatga aggttaacgg caacggacga gccaaaatac tcacctccga cgaactcagg    4680
cgactgttta gcgacggatt caccacaccg cgcgatcgcg ttttgtttgg catctgtcta    4740
ttcaccggtt gccgcgttag tgaagctcta gcactccaaa caacggacat aaaggcgaa    4800 acactaacct ttaggaagtc taccaccaaa gggaaactca aaacccgcgt ggttgacatc    4860
cagccaggac tagccgcact catggctgac tatcacccca aaccgggaac cctgttccct    4920
ggcatgaggg gagtcagcga taggctcacg cgatacgcgg cggataaaat cttgcgcgat    4980
gcagccaaaa gaatcgggct agaaggcatc agtacccaca gtttccgccg tactgccctc    5040
aaccaaatgt ctagcgccgg tatcccgttg cgacacattc aagagatatc cggtcacaat    5100
gaccttggca cactgcaacg ctatcttgaa gttacacccg aacagcgacg caaagctgta    5160
tccgtgattg gcttctaatg tacgccaacg ctgtttagac ccctatgggt gctaaaaaaa    5220
gacgcagcct aaacacacgc tctacacttg aggatacttt taaagtatcc atcggttcta    5280
gaactctgca cacgttccgg actttggaaa cgttatacct ttccctgtgt tgcagaatgc    5340
tgcaatattt cttcgacaag ttaacttgtg actggtttaa tatttctca aattgcccca     5400 aaacaacacg cctaaatcct tagacgtttc tgtggaaacc tattaggttt ttatcgccgt    5460
tgttttagtg gtaaacccaa agggtttgta tattcttgta tgaagttcga ctctgagggt    5520
taagaagaat ggctcgccga atttttttaca agtggaaacc gattaaaggt taagggtcaa    5580
tcgggacgat gaatattttc taattgtgac cttctccatc taataagctt tctttggggt    5640
taaggtcgaa gaaagtacta cgcatgatct gcatacgatc tctattgcca aaaagccgcg    5700
accctatagg ctctcggtca tgctgcacta gttcgtgtcg atcactatac tggttgccgc    5760
agcatttcac gctaaaaaaa aattcttaaa aatgtccttc atatctcgcc agagtggcaa    5820
cctattacaa aacggttgcc tacccgaccg gctcgatttt cgctgaagtg gcactgtgac    5880
agtttgaaat ggtacttccg ccgtgctgct gacatcgttg ttagggtgaa ttgttcgcgg    5940
tagatgttgc accgattcat gaacaccttg tcacccactt tgaataatcg accgtcaaat    6000
tcagtcgcgt caatttggta agtgttgggc tgtctctttt tggctccagg ggcaatgcca    6060
```

```
tcagaaaaca caaccgcgtc acccataact tgataaccga tatcagttttt ggttccagtg   6120 aaagcccaaa attcagacgc gtcattattc cgagcgtgcc ggagttgatt gtactcaatt   6180
ttggcttggc aaagttgacg gcgattcatg cccagctgct tttgatgtcg tcgcactgtg   6240
cgcttgtgaa tacccaactc acagctgaca gcttttttgag atgtaccata gtggatgaaa   6300 cttttttgaga cgaatatccg cgacgaacta atgtgaagta cacaaggtac ttccccctct   6360
ggcgatttaa gagaggattg ccttgtgtcc ttcactagct cgttcgggtg tggcgctcca   6420
aaaagttttc tgtactctgg tttaagttgt ctgttggccg catagcggct cttttgttga   6480
aagctttgtg tgactatgcc agtggtcagt gagcgtaaat cgcttaacac ttggactaaa   6540
ggcactactg caacatcacc ccatcttttt aaatttaggt tgtaacaaac ttgaaacata   6600
ccgcccaagt agacggttat cattcctgct ttaattttgt agcggcggaa tgctcctatt   6660 tttttttccat cctgtaacca acggtaaaca gacttatcac tacaatctaa gaacgtctgt   6720
actacaggca atggcaatgt taaatgacca gacccatcct tatcaagcgc tcgacacaaa   6780
taccacaacc gcgcacaagg ttctcgacca atgcgagtgt gtaccctgac cgtgtaagtg   6840
ccaagaatta tttcagtttg tagttcccctt gtaagcaggg ttagtgatac atttgtattt   6900
aagctttctg ggctgatcat ttggaaatgt ctcagtccag tacctattga atgttatttg   6960
cttaacctga agctaaataa aacttgttaa ctacacccat taattgataa attcaaagca   7020
cgttttttct gtttggtgtt tggtgtggta acaattctgt gtatgtgtgt tttatttagc   7080
ttcggttaag tagcataaca accccccaagc actgaacttt ttttaatagg taatttaaac   7140
tttgcctatc ggcaaaattt tcaatcaatt gtacgccaaa gtgttgcatg atcaacgttt   7200
gacttatttt tgtatttact aaatactgaa tttcgccgtg acgctttta cagatggaaa   7260 ttcacggcaa aatgtttttt gctaactttg ctatgtaaaa caagaaactt ggcactcggt   7320
tattactaaa taaactggta aaaataacc attagaacca aaagaacga aaaccagtac   7380 acccttgcca gttttcaagc ttttgctatg acgactctaa taatcgggtt taacaccatt   7440
ccgctttgag aaaattatcc ttgtacagca agtaacagtc aatgctaaac cgcaccgcta   7500
caaatcctta agttttttcca gtagcgattt accttcttgg taacgcccgc cttgatagcc   7560
caaaatttct ttaatcacct tactttctga aaacccgct tccagacagg cttttaccac   7620
ttttgctagg gtttcatctc ttggttctgg gagggatgaa acgggctgta atgcttgttc   7680
tgaggtcggt tgagccgttt ggagtggctg aaaactggtt acagactgta accggggcat   7740
aaccattttg taactgctta catctggtaa ctgacacggc atatcatcca ccatgcagcg   7800
atatttcccc gactttaacc actccacaag ggcaaggtct tttaaggact tggcgtggct   7860
aactgcaaac ttacccaggc gtaacatcct aaaacactta cggacaccgc cttcaccctc   7920
gatacctaag gtcttgacat tatcatcttg agtcagccca ataacaaaac gcttgggctt   7980
gcggccgcgc ctggcgtgtt tgatgagcca ttcggttgct atctcgactt catctctcag   8040
cagtggcagt tcttcagcaa ttaaaacgct ttctttttcct gctagtgcct tatccccaga   8100 ctcacccccgt agctcaatcc ggcgctgcaa ttcctccagg tcagcagcca tgcccgactg   8160
tatagcctca aagtcaccac ggcggccaat gacatttaac cccgtccact cgtccggtgc   8220
agcgtcagcg tcatagactg tcacctcacc cccgacttga taagcaagcc attgggctat   8280
ggtgcttttg ccagttcccg tatccccaac tattaaacag tgcttaccag acagagcttg   8340
catcaagtcg gtgatgattc cctctggttc gaccgcaagg gtgacggcgg tagtgtcaat   8400
gatagccgcg ccgtaagtgc cagcataggg caattggtcg taaactttga ccaagttgta   8460
```

```
tacagactgt ctacaccact tcaccactgt taacgctgtt tgcaaagcgt aagacgtggc   8520
atcaaataaa aatatgctgg cactaaaagt taatcgcccc aatccccaca gtaaaaacct   8580
gcctagctgt tgacgactag gcaagtgcat ttcaatccag tcatttgcca taaatcaccc   8640
cgtctttaaa gccttgcagt tgagcgcgac aggtatttaa ctgtgcttgt aactctgttt   8700
gctggttttg ataccacaga ctgacggcgg cggccgccag tcctaaaaat agaaactggc   8760
gatcgctcat tattgactta ctccctgttg attagcgtgg tagtgagtca tagccgcatt   8820
gaccgcttct tgggcttggg gtgttctgcc aagattgggt tttgtagggt catcgttggc   8880
tacgactaag gacgcttgtt cggctatcgc ttgcgggaca ccaactttag ttaactctgt   8940
caaggatact tggtaaagtc gctcgttcat tagccgattc tccggtacat aaaactgttg   9000
ctggcagtcc cttcattggc gacgagttct tcagccggag tatcagcgat aatgtcagcc   9060
cagccggtga cattattatt aataatgttt tgttcggcaa ttgcacccaa gccaggacgc   9120
gccgtttcaa actcagagat gacttgctgc tctttctcgg tgagtggtct atctgtcatg   9180
ataattatgt ccttcattat gtaggcgatt ccagtgggtg tttacgaggc agtccacagg   9240
aatcagtgcg attcaccttt aaggtgaatc gtcatcaaaa aatcactcgg tagcaacgac   9300
ccgaaccgac caggattgat ttcccggttc tcagttcgca ggcttttgag cgcgtcacct   9360
tgaccattgg gtaactgcca tcagccgata agctaaacgg gctgtatagc ggtaaagcat   9420
cccacacagt cgggctggca tcaactttgc aggaatagct cacgtcactc atctcactcg   9480
cgcctgggtt ggatggcagc gaaggcagat tacgacgcag tttttttactg gcacttttac   9540 ccgcattaaa aacgggtaca gtgccattgt tgacggtctg tacttcggtc atatactcgg   9600
tgtacactta atacactcta tactattact gccgattagt acatttgtca atcactcttt   9660
gcacaaggtg tatgatatgg actcaggagt acaccaaacg tcatgccaac caataaaggg   9720
agaatagcag tcactctaga agctgaaatt taccaatgga ttgctaaccg agcgtctgag   9780
gaaggaagac cgttggctaa tcttgccgct ttcttactca cacgagttgt taaagaacaa   9840
atggaacaag aagccaagga caaccaagac aagcagggg cagcatgagc gaagacagac   9900
tagccagaat agaagctgcg ttagacagcc aagttgcagt gaatgccgac ctccgcacat   9960
cggttacaga actccgcgca accgcagaag cattgttgca aacagttcaa atccatcagc  10020
agaactttga aattcttacc gctaggcaat tacaaaccga agcacggctt gatgagtacc  10080
aacgtaccac tagcgcggca ctcgacagaa ttggcgcggt cttagactac ctcgttaggc  10140
agcaaaacgg ttgaggtgag ggatgagcga tgactatcta gacggatatc ccgcaagagg  10200 cccttttcgtc ttcaagaatt cccgtttgac tggcgatgct gctactgaaa ctaacaacta  10260
catcgactac gcaattaacg ccctcagcta attttgctta gtctaggccc ggatgggtaa  10320
gtggttttca gcttaagtgt tgggttctac ttacttctcc gggtcttgct ctatctaaaa  10380
acattggttt aacaaggagt attaggcaaa tgccagttac tgtcgctgcc tctcgcttgg  10440
gaaccgctgc gttttgaccaa tcacccgtcg aactgcgcgc taactattct cgacctgcag  10500
gtcgactttt ttgctgaggt actgagtaca cagctaataa aattgggcaa tctccgcgcc  10560
tctatgactt gaaggagagt gtaggggtat agggaaaga tatctttat ctacatcaca  10620 taaataaaaa atttaatttg tcgctctggc tgcatatatt gatgtatttt tagccataag  10680
ttttttagtg ccatgtaatt atagtgattt ttagcgatcg cagagcattt ttccctggat  10740
ttatcgcgat ctcaaaaaaa atttgcccga agtatgacag attgtcatat ttggtgtcga  10800
```

-continued

```
ttttatttaa aatgaaataa gaaaaataaa actacaggtt aggagaacgc catgaattct    10860
tatactgtcg gtacctattt agcggagcgg cttgtccaga ttggtctcaa gcatcacttc    10920
gcagtcgcgg gcgactacaa cctcgtcctt cttgacaacc tgcttttgaa caaaaacatg    10980
gagcaggttt attgctgtaa cgaactgaac tgcggtttca gtgcagaagg ttatgctcgt    11040
gccaaaggcg cagcagcagc cgtcgttacc tacagcgtcg gtgcgctttc cgcatttgat    11100
gctatcggtg gcgcctatgc agaaaacctt ccggttatcc tgatctccgg tgctccgaac    11160
aacaatgatc acgctgctgg tcacgtgttg catcacgctc ttggcaaaac cgactatcac    11220
tatcagttgg aaatggccaa gaacatcacg gccgcagctg aagcgattta cacccccagaa    11280 gaagctccgg ctaaaatcga tcacgtgatt aaaactgctc ttcgtgagaa gaagccggtt    11340
tatctcgaaa tcgcttgcaa cattgcttcc atgccctgcg ccgctcctgg accggcaagc    11400
gcattgttca atgacgaagc cagcgacgaa gcttctttga atgcagcggt tgaagaaacc    11460
ctgaaattca tcgccaaccg cgacaaagtt gccgtcctcg tcggcagcaa gctgcgcgca    11520
gctggtgctg aagaagctgc tgtcaaattt gctgatgctc tcggtggcgc agttgctacc    11580
atggctgctg caaaaagctt cttcccagaa gaaaacccgc attacatcgg tacctcatgg    11640
ggtgaagtca gctatccggg cgttgaaaag acgatgaaag aagccgatgc ggttatcgct    11700
ctggctcctg tcttcaacga ctactccacc actggttgga cggatattcc tgatcctaag    11760
aaactggttc tcgctgaacc gcgttctgtc gtcgttaacg gcgttcgctt ccccagcgtt    11820
catctgaaag actatctgac ccgtttggct cagaaagttt ccaagaaaac cggtgctttg    11880
gacttcttca aatcccctcaa tgcaggtgaa ctgaagaaag ccgctccggc tgatccgagt    11940
gctccgttgg tcaacgcaga aatcgcccgt caggtcgaag ctcttctgac cccgaacacg    12000
acggttattg ctgaaaccgg tgactcttgg ttcaatgctc agcgcatgaa gctcccgaac    12060
ggtgctcgcg ttgaatatga aatgcagtgg ggtcacatcg gttggtccgt tcctgccgcc    12120
ttcggttatg ccgtcggtgc tccggaacgt cgcaacatcc tcatggttgg tgatggttcc    12180
ttccagctga cggctcagga agtcgctcag atggttcgcc tgaaactgcc ggttatcatc    12240
ttcttgatca ataactatgg ttacaccatc gaagttatga tccatgatgg tccgtacaac    12300
aacatcaaga actgggatta tgccggtctg atggaagtgt tcaacggtaa cggtggttat    12360
gacagcggtg ctggtaaagg cctgaaggct aaaaccggtg gcgaactggc agaagctatc    12420
aaggttgctc tggcaaacac cgacggccca accctgatcg aatgcttcat cggtcgtgaa    12480
gactgcactg aagaattggt caaatggggt aagcgcgttg ctgccgccaa cagccgtaag    12540
cctgttaaca agctcctcta gtttttgggg atcaattcga gctctctgga taaaactaat    12600
aaactctatt acccatgatt aaagcctacg ctgccctgga agccaacgga aaactccaac    12660
cctttgaata cgaccccggt gccctgggtg ctaatgaggt ggagattgag gtgcagtatt    12720
gtggggtgtg ccacagtgat ttgtccatga ttaataacga atggggcatt tccaattacc    12780
ccctagtgcc gggtcatgag gtggtgggta ctgtggccgc catgggcgaa ggggtgaacc    12840
atgttgaggt gggggattta gtggggctgg gttggcattc gggctactgc atgacctgcc    12900
atagttgttt atctggctac cacaacccttt gtgccacggc ggaatcgacc attgtgggcc    12960
actacggtgg cttttggcgat cgggttcggg ccaagggagt cagcgtggtg aaattaccta    13020
aaggcattga cctagccagt gccgggcccc ttttctgtgg aggaattacc gttttcagtc    13080
ctatggtgga actgagtttta aagcccactg caaaagtggc agtgatcggc attggggct    13140 tgggccattt agcggtgcaa tttctccggg cctggggctg tgaagtgact gcctttacct    13200
```

```
ccagtgccag gaagcaaacg gaagtgttgg aattgggcgc tcaccacata ctagattcca   13260
ccaatccaga ggcgatcgcc agtgcggaag gcaaatttga ctatattatc tccactgtga   13320
acctgaagct tgactggaac ttatacatca gcaccctggc gccccaggga catttccact   13380
ttgttggggt ggtgttggag cctttggatc taaatctttt tccccttttg atgggacaac   13440
gctccgtttc tgcctcccca gtgggtagtc ccgccaccat tgccaccatg ttggactttg   13500
ctgtgcgcca tgacattaaa cccgtggtgg aacaatttag ctttgatcag atcaacgagg   13560
cgatcgccca tctagaaagc ggcaaagccc attatcgggt agtgctcagc catagtaaaa   13620
attagctctg caaaggttgc ttctgggtcc gtggaatgtg caaacggagt cgatctcagt   13680
tttgatacgc tctatctgga aagcttgaca ttcgatctgc agcccgggg             13729

<210> SEQ ID NO 2
<211> LENGTH: 8921
<212> TYPE: DNA
<213> ORGANISM: Artificial Sequence
<220> FEATURE:
<223> OTHER INFORMATION: K236Cm plasmid

<400> SEQUENCE: 2
tcgacgggtt gatgatgggt agtcgttccg gtgccatcga tccgggatc attgttcact      60 taatgcgaca atcagattac tctgctgaaa gattggacta tgttttaaat aaagcttccg     120
gcttacgcgg tatttctggg gtttccagcg atttacccca ggtcatagaa gccattaccc     180
aaggtaacta ccgcgcccaa ctggcgtggg atatgtacgt acatcggctg cgttctggga     240
ttggttccat gttggcgagt ctgggggggtt tggatgtgtt ggtgtttacc gcaggcgtag     300
gggaaaaatc agcaggtatt cgccaagcag cttgtgaagc ctttgggttt ttagggttaa     360
aacttgaccc agaaaagaac caaaacaaac cagtagatat agatatcgcc actgctgatt     420
ctacagtacg ggtgttagta attcatactc aagaagattg ggcgatcgca caacaatgtt     480
ggcatttgtt aaaaaggtaa gcgggagagt gagcgtatca tgaatttacc tagtagtggc     540
cagatataac gtaaagtacg tttgacaatt tctggtgtca accacgaaag aattagcaac     600
aacaataagt aaatgttact caactcccca acgccatgag aaataatacc agaaacacta     660
caaacgatag cccaaaccca attaatgcag caatggcaac aacgttgcgc aaactattaa     720
ctggcgaact acttactcta gcttcccggc aacaattaat agactggatg gaggcggata     780
aagttgcagg accacttctg cgctcggccc ttccggctgg ctggtttatt gctgataaat     840
ctggagccgg tgagcgtggg tctcgcggta tcattgcagc actggggcca gatggtaagc     900
cctcccgtat cgtagttatc tacacgacgg ggagtcaggc aactatggat gaacgaaata     960
gacagatcgc tgagataggt gcctcactga ttaagcattg gtaactgtca gaccaagttt    1020
actcatatat actttagatt gatttaaaac ttcatttttta atttaaaagg atctaggtga    1080
agatcctttt tgataatctc atgaccaaaa tcccttaacg tgagttttcg ttccactgag    1140
cgtcagaccc cgtagaaaag atcaaggat cttcttgaga tccttttttt ctgcgcgtaa    1200
tctgctgctt gcaaacaaaa aaaccaccgc taccagcggt ggtttgtttg ccggatcaag    1260
agctaccaac tcttttccg aaggtaactg gcttcagcag agcgcagata ccaaatactg    1320
tccttctagt gtagccgtag ttaggccacc acttcaagaa ctctgtagca ccgcctacat    1380
acctcgctct gctaatcctg ttaccagtgg ctgctgccag tggcgataag tcgtgtctta    1440
ccgggttgga ctcaagacga tagttaccgg ataaggcgca gcggtcgggc tgaacggggg    1500
```

-continued

```
gttcgtgcac acagcccagc ttggagcgaa cgacctacac cgaactgaga tacctacagc   1560
gtgagcattg agaaagcgcc acgcttcccg aagggagaaa ggcggacagg tatccggtaa   1620
gcggcagggt cggaacagga gagcgcacga gggagcttcc aggggggaaac gcctggtatc   1680
tttatagtcc tgtcgggttt cgccacctct gacttgagcg tcgatttttg tgatgctcgt   1740
cagggggggcg gagcctatgg aaaaacgcca gcaacgcggc cttttttacgg ttcctggcct   1800
tttgctggcc ttttgctcac atgttctttc ctgcgttatc ccctgattct gtggataacc   1860
gtattaccgc ctttgagtga gctgataccg ctcgccgcag ccgaacgacc gagcgcagcg   1920
agtcagtgag cgaggaagcg gaagagcgcc tgatgcggta ttttctcctt acgcatctgt   1980
gcggtatttc acaccgcata tggtgcactc tcagtacaat ctgctctgat gccgcatagt   2040
taagccagta tacactccgc tatcgctacg tgactgggtc atggctgcgc ccgacaccc    2100
gccaacaccc gctgacgcgc cctgacgggc ttgtctgctc ccggcatccg cttacagaca   2160
agctgtgacc gtctccggga gctgcatgtg tcagaggttt tcaccgtcat caccgaaacg   2220
cgcgaggcag gctggctgtt ttacgcgtat gacaggctcc ggaagacggt tgttgcgcac   2280
gtattcggtg aacgcactat ggcgacgctg ggcgtctta tgagcctgct gtcacccttt    2340
gacgtggtga tatggatgac ggatggctgg ccgctgtatg aatcccgcct gaagggaaag   2400
ctgcacgtaa tcagcaagcg atatacgcag cgaattgagc ggcataacct gaatctgagg   2460
cagcacctgg cacggctggg acggaagtcg ctgtcgttct caaaatcggt ggagctgcat   2520
gacaaagtca tcgggcatta tctgaacata aaacactatc aataagttgg agtcattacc   2580
aaaaggttag gaatacggtt agccatttgc ctgcttttat atagttcata tgggattcac   2640
ctttatgttg ataagaaata aagaaaatg ccaataggat atcggcattt tcttttgcgt    2700
ttttatttgt taactgttaa ttgtccttgt tcaaggatgc tgtctttgac aacagatgtt   2760
ttcttgcctt tgatgttcag caggaagctt ggcgcaaacg ttgattgttt gtctgcgtag   2820
aatcctctgt ttgtcatata gcttgtaatc acgacattgt ttccttttcgc ttgaggtaca   2880
gcgaagtgtg agtaagtaaa ggttacatcg ttaggatcaa gatccatttt taacacaagg   2940
ccagttttgt tcagcggctt gtatgggcca gttaaagaat tagaaacata accaagcatg   3000
taaatatcgt tagacgtaat gccgtcaatc gtcattttg atccgcggga gtcagtgaac    3060
aggtaccatt tgccgttcat tttaaagacg ttcgcgcgtt caatttcatc tgttactgtg   3120
ttagatgcaa tcagcggttt catcactttt ttcagtgtgt aatcatcgtt tagctcaatc   3180
ataccgagag cgccgtttgc taactcagcc gtgcgtttt tatcgctttg cagaagtttt    3240
tgactttctt gacggaagaa tgatgtgctt ttgccatagt atgctttgtt aaataaagat   3300
tcttcgcctt ggtagccatc ttcagttcca gtgtttgctt caaatactaa gtatttgtgg   3360
cctttatctt ctacgtagtg aggatctctc agcgtatggt tgtcgcctga gctgtagttg   3420
ccttcatcga tgaactgctg tacatttga tacgttttc cgtcaccgtc aaagattgat    3480
ttataatcct ctacaccgtt gatgttcaaa gagctgtctg atgctgatac gttaacttgt   3540
gcagttgtca gtgtttgttt gccgtaatgt ttaccggaga atcagtgta gaataaacgg    3600
attttttccgt cagatgtaaa tgtggctgaa cctgaccatt cttgtgtttg gtcttttagg   3660
atagaatcat ttgcatcgaa tttgtcgctg tcttttaaga cgcggccagc gttttttccag  3720
ctgtcaatag aagtttcgcc gacttttttga tagaacatgt aaatcgatgt gtcatccgca  3780
tttttaggat ctccggctaa tgcaaagacg atgtggtagc cgtgatagtt tgcgacagtg   3840
ccgtcagcgt tttgtaatgg ccagctgtcc caaacctcca ggccttttgc agaagagata   3900
```

-continued

```
tttttaattg tggacgaatc gaattcagga acttgatatt tttcattttt ttgctgttca   3960
gggatttgca gcatatcatg gcgtgtaata tgggaaatgc cgtatgtttc cttatatggc   4020
ttttggttcg tttctttcgc aaacgcttga gttgcgcctc ctgccagcag tgcggtagta   4080
aaggttaata ctgttgcttg ttttgcaaac tttttgatgt tcatcgttca tgtctccttt   4140
tttatgtact gtgttagcgg tctgcttctt ccagccctcc tgtttgaaga tggcaagtta   4200
gttacgcaca ataaaaaaag acctaaaata tgtaaggggt gacgccaaag tatacactttt  4260
gcccttttaca cattttaggt cttgcctgct ttatcagtaa caaacccgcg cgatttactt   4320
ttcgacctca ttctattaga ctctcgtttg gattgcaact ggtctatttt cctcttttgt   4380
ttgatagaaa atcataaaag gatttgcaga ctacgggcct aaagaactaa aaaatctatc   4440
tgtttctttt cattctctgt atttttata gtttctgttg catgggcata aagttgcctt    4500
tttaatcaca attcagaaaa tatcataata tctcatttca ctaaataata gtgaacggca   4560
ggtatatgtg atgggttaaa aaggatcgat cctctagcta gagtcgacct gcatccctta   4620
acttacttat taaataattt atagctattg aaaagagata agaattgttc aaagctaata   4680
ttgtttaaat cgtcaattcc tgcatgtttt aaggaattgt taaattgatt ttttgtaaat   4740
attttcttgt attctttgtt aacccatttc ataacgaaat aattatactt tgtttatct   4800
ttgtgtgata ttcttgatttt ttttctactt aatctgataa gtgagctatt cactttaggt  4860
ttaggatgaa aaaaaataaa aaagggggacc tctagggtcc ccaattaatt agtaatataa  4920
tctattaaag gtcattcaaa aggtcatcca ccggatcagc ttagtaaagc cctcgctaga   4980
ttttaatgcg gatgttgcga ttacttcgcc aactattgcg ataacaagaa aaagccagcc   5040
tttcatgata tatctcccaa tttgtgtagg gcttattatg cacgcttaaa aataataaaa   5100
gcagacttga cctgatagtt tggctgtgag caattatgtg cttagtgcat ctaacgcttg   5160
agttaagccg cgccgcgaag cggcgtcggc ttgaacgaat tgttagacat tatttgccga   5220
ctaccttggt gatctcgcct ttcacgtagt ggacaaattc ttccaactga tctgcgcgcg   5280
aggccaagcg atcttcttct tgtccaagat aagcctgtct agcttcaagt atgacgggct   5340
gatactgggc cggcaggcgc tccattgccc agtcggcagc gacatccttc ggcgcgattt   5400
tgccggttac tgcgctgtac caaatgcggg acaacgtaag cactacattt cgctcatcgc   5460
cagcccagtc gggcggcgag ttccatagcg ttaaggtttc atttagcgcc tcaaatagat   5520
cctgttcagg aaccggatca aagagttcct ccgccgctgg acctaccaag gcaacgctat   5580
gttctcttgc ttttgtcagc aagatagcca gatcaatgtc gatcgtggct ggctcgaaga   5640
tacctgcaag aatgtcattg cgctgccatt ctccaaattg cagttcgcgc ttagctggat   5700
aacgccacga aatgatgtcg tcgtgcacaa caatggtgac ttctacagcg cggagaatct   5760
cgctctctcc aggggaagcc gaagtttcca aaaggtcgtt gatcaaagct cgccgcgttg   5820
tttcatcaag ccttacggtc accgtaacca gcaaatcaat atcactgtgt ggcttcaggc   5880
cgccatccac tgcggagccg tacaaatgta cggccagcaa cgtcggttcg agatggcgct   5940
cgatgacgcc aactacctct gatagttgag tcgatacttc ggcgatcacc gcttccctca   6000
tgatgtttaa ctttgtttta gggcgactgc cctgctgcgt aacatcgttg ctgctccata   6060
acatcaaaca tcgacccacg gcgtaacgcg cttgctgctt ggatgcccga ggcatagact   6120
gtaccccaaa aaaacagtca taacaagcca tgaaaaccgc cactgcgccg ttaccaccgc   6180
tgcgttcggt caaggttctg gaccagttgc gtgagcgcat acgctacttg cattacagct   6240
```

```
tacgaaccga acaggcttat gtccactggg ttcgtgcctt catccgtttc cacggtgtgc   6300 gtcaccggc  aaccttgggc agcagcgaag tcgaggcatt tctgtcctgg ctggcgaacg   6360
agcgcaaggt ttcggtctcc acgcatcgtc aggcattggc ggccttgctg ttcttctacg   6420
gcaaggtgct gtgcacggat ctgccctggc ttcaggagat cggaagacct cggccgtcgc   6480
ggcgcttgcc ggtggtgctg accccggatg aagtggttcg catcctcggt tttctggaag   6540
gcgagcatcg tttgttcgcc cagcttctgt atggaacggg catgcggatc agtgagggtt   6600
tgcaactgcg ggtcaaggat ctggatttcg atcacggcac gatcatcgtg cgggagggca   6660
agggctccaa ggatcgggcc ttgatgttac ccgagagctt ggcacccagc ctgcgcgagc   6720
aggggaattg atccggtgga tgaccttttg aatgaccttt aatagattat attactaatt   6780
aattggggac cctagaggtc ccctttttta ttttactgcg atgagtggca gggcggggcg   6840 taatttttt  aaggcagtta ttggtgccct aaaacgcctg gtgctacgcc tgaataagtg   6900
ataataagcg gatgaatggc agaaattcga tatctagatc tcgagctgga tacttcccgt   6960
ccgccagggg gacatgccgg cgatgctgaa ggtcgcgcgc attcccgatg aagaggccgg   7020
ttaccgcctg tttgaggata tagtaatctt tctaaatagc tttggattgg aggagtatgg   7080
ccactaatac taagttcagc taataaaaaa atttgctaaa gaactccagc tggatttcac   7140
tgatgagaat atcgtcggag ataaatataa taattccacg gactatagac tatactagtc   7200
acgaacaagt tcccatcctc cacgacgata gtattgaccg cgataatttg ctctacgata   7260
atgccgacca cgataacgtc cattacgata gtaatgcctg taataatgcc gattatgata   7320
gcgccgtctg tggtaatgcc gtctagcccg tcttcttccg tgataacgcc gtctatattg   7380
tcggtgagct attaatgttt ctttgtgttc accttcgact aagtttgttt ctgcttcaat   7440
agtttgctca ttcaaagcat tattgagagt attctcttta gcttcaacta atgtaggcgg   7500
atagatgaaa gctaataaca ggaacacgat tgaggatagc ttttggaaac ggttcacgtc   7560
tttgcttttc ctaaaatatc ggtaataagt ttaataaata cctgaaatta ggaaatgata   7620
tagctcacac ttcacaaacc tgaatcacgt aaatgtaatg aaagtactaa ttttgaatgc   7680
tggttcaagc agccaaaaga gttgtctata tgaaattccc gatgatgctc tcctgagtga   7740
agcaccccag ccgctttggg aagggaaagt taactggact caagacagaa gtgtggcgga   7800
aattgaggtc aaaacagcta gaggtgaaac gctccatgag tctatatatg gtgattcccg   7860
tcaagcacac gtcacctata tgctttatac cctcagtcgc ggccgccctg tgacggaaga   7920
tcacttcgca gaataaataa atcctggtgt ccctgttgat accgggaagc cctgggccaa   7980
cttttggcga aaatgagacg ttgatcggca cgtaagaggt tccaactttc accataatga   8040
aataagatca ctaccgggcg tatttttga  gttatcgaga ttttcaggag ctaaggaagc   8100
taaaatggag aaaaaaatca ctggatatac caccgttgat atatcccaat ggcatcgtaa   8160
agaacatttt gaggcatttc agtcagttgc tcaatgtacc tataaccaga ccgttcagct   8220
ggatattacg gcctttttaa agaccgtaaa gaaaaataag cacaagtttt atccggcctt   8280
tattcacatt cttgcccgcc tgatgaatgc tcatccggaa ttccgtatgg caatgaaaga   8340
cggtgagctg gtgatatggg atagtgttca cccttgttac accgttttcc atgagcaaac   8400
tgaaacgttt tcatcgctct ggagtgaata ccacgacgat ttccggcagt ttctacacat   8460
atattcgcaa gatgtggcgt gttacggtga aaacctggcc tatttcccta aagggtttat   8520
tgagaatatg ttttttcgtct cagccaatcc ctgggtgagt ttcaccagtt ttgatttaaa   8580
cgtggccaat atgacaaact tcttcgcccc cgttttcacc atgggcaaat attatacgca   8640
```

```
aggcgacaag gtgctgatgc cgctggcgat tcaggttcat catgccgttt gtgatggctt    8700
ccatgtcggc agaatgctta atgaattaca acagtactgc gatgagtggc agggcggggc    8760 gtaattttt taaggcagtt attggtgccc ttaaacgcct ggtgctacgc ctgaataagt    8820
gataataagc ggatgaatgg cagaaattcg atatctagat ctcgagctgg atacttcccg    8880
tccgccaggg ggacatgccg gcgatggcgg ccgcctgcag g                       8921
```

<210> SEQ ID NO 3
<211> LENGTH: 12288
<212> TYPE: DNA
<213> ORGANISM: Artificial Sequence
<220> FEATURE:
<223> OTHER INFORMATION: K244 plasmid

<400> SEQUENCE: 3

```
actttcttcg accttaaccc caaagaaagc ttattagatg gagaaggtca caattagaaa      60
atattcatcg tcccgattga cccttaacct ttaatcggtt tccacttgta aaaaattcgg     120
cgagccattc ttcttaaccc tcagagtcga acttcataca agaatataca aacccctttgg    180 gtttaccact aaaacaacgg cgataaaaac ctaataggtt tccacagaaa cgtctaagga    240
tttaggcgtg ttgttttggg gcaatttgag aaaatattaa accagtcaca agttaacttg    300
tcgaagaaat attgcagcat tctgcaacac agggaaaggt ataacgtttc caaagtccgg    360
aacgtgtgca gagttctaga accgatggat actttaaaag tatcctcaag tgtagagcgt    420
gtgtttaggc tgcgtctttt tttagcaccc atagggtct aaacagcgtt ggcgtacatt     480
agaagccaat cacggataca gctttgcgtc gctgttcggg tgtaacttca agatagcgtt    540
gcagtgtgcc aaggtcattg tgaccggata tctcttgaat gtgtcgcaac gggataccgg    600
cgctagacat ttggttgagg gcagtacggc ggaaactgtg ggtactgatg ccttctagcc    660
cgattctttt ggctgcatcg cgcaagattt tatccgccgc gtatcgcgtg agcctatcgc    720
tgactcccct catgccaggg aacagggttc ccggtttggg gtgatagtca gccatgagtg    780
cggctagtcc tggctggatg tcaaccacgc ggggttttgag tttccctttg gtggtagact    840
tcctaaaggt tagtgtttcg ccttaatgt ccgttgtttg gagtgctaga gcttcactaa    900
cgcggcaacc ggtgaataga cagatgccaa acaaaacgcg atcgcgcggt gtggtgaatc    960
cgtcgctaaa cagtcgcctg agttcgtcgg aggtgagtat tttggctcgt ccgttgccgt   1020
taaccttcat aaccctaca gattaagcat tccaatactc tacacgttat ctgcatttg    1080 tggaattggt ggctatatct attgattctt cgtatgcttt ctgttgaaag ccagtgctag    1140
tttagccaag cttatcaatc gttgcacggt aaaatcaggc tttcgacgta aggacagaat   1200
tttgataact tcagcttatg ttgtctcctg aagaaagcaa ctctttgata aacgcgtcga    1260
tggctttccc ggcggctgac tgcctaccca ttttagctt attgagggtg cgatcgcggg    1320
ttgcctccaa tttgtctaga ttgtctatac tattgtctat attctttctg tcttgcccgg   1380
tagcttgtcc ttctgcctga actaccgggc tttcgatttt cccgcagtt cctccagttg    1440 cgattgaagt tgtctagac gtgttgctag attatcttct atacgcttgt ctataaattc    1500
atctatattg tctagattat tagttgtgac tttatctaga cgttgttcaa tattgtctat   1560
acgctgttcg agggatgtgt ctagatgggt gggagtgtga aagtgggag tattaaacct    1620 gttacctgcc aaataccaac gaacaaattc tgttaacagt gctgaggcgt tggaactttc    1680
agaactagca aggtttttaa aagactccca ttcttcggag tcaatacgaa aagtggctag   1740
```

```
agttttgtct gccatgatta gataatgtct atacttgtat agatagcagt ataaactatt    1800
gtctatatta gtgtctatat aagtctagat atcgtccatt ccgacagcat cgccagtcac    1860
tatgcgtgc tgctagtggt tcccctcagc ttgcgactag atgttgaggc ctaacatttt     1920
attagagagc aggctagttg cttagataca tgatcttcag gccgttatct gtcagggcaa    1980
gcgaaaattg gccatttatg acgaccaatg ccccgcagaa gctccatct ttgccgccat     2040
agacgccgcg ccccccttttt ggggtgtaga acatcctttt gccagatgtg gaaaagaagt   2100
tcgttgtccc attgttggca atgacgtagt agccggcgaa agtgcgagac ccatttgcgc    2160
tatatataag cctacgattt ccgttgcgac tattgtcgta attggatgaa ctattatcgt    2220
agttgctctc agagttgtcg taatttgatg gactattgtc gtaattgctt atggagttgt    2280
cgtagttgct tggagaaatg tcgtagttgg atggggagta gtcataggga agacgagctt    2340
catccactaa aacaattggc aggtcagcaa gtgcctgccc cgatgccatc gcaagtacga    2400
ggcttagaac caccttcaac agatcgcgca tagtcttccc cagctctcta acgcttgagt    2460
taagccgcgc cgcgaagcgg cgtcggcttg aacgaattgt tagacattat ttgccgacta    2520
ccttggtgat ctcgcctttc acgtagtgaa caaattcttc caactgatct gcgcgcgagg    2580
ccaagcgatc ttcttgtcca agataagcct gcctagcttc aagtatgacg ggctgatact    2640
gggccggcag gcgctccatt gcccagtcgg cagcgacatc cttcggcgcg attttgccgg    2700
ttactgcgct gtaccaaatg cgggacaacg taagcactac atttcgctca tcgccagccc    2760
agtcgggcgg cgagttccat agcgttaagg tttcatttag cgcctcaaat agatcctgtt    2820
caggaaccgg atcaaagagt tcctccgccg ctggacctac caaggcaacg ctatgttctc    2880
ttgcttttgt cagcaagata gccagatcaa tgtcgatcgt ggctggctcg aagatacctg    2940
caagaatgtc attgcgctgc cattctccaa attgcagttc gcgcttagct ggataacgcc    3000
acggaatgat gtcgtcgtgc acaacaatgg tgacttctac agcgcggaga atctcgctct    3060
ctccagggga agccgaagtt ccaaaaaggt cgttgatcaa agctcgccgc gttgtttcat    3120
caagccttac ggtcaccgta accagcaaat caatatcact gtgtggcttc aggccgccat    3180
ccactgcgga gccgtacaaa tgtacggcca gcaacgtcgg ttcgagatgg cgctcgatga    3240
cgccaactac ctctgatagt tgagtcgata cttcggcgat caccgcttcc ctcatgatgt    3300
ttaactcctg aattaagccg cgccgcgaag cggtgtcggc ttgaatgaat tgttaggcgt    3360
catcctgtgc tccaagcttg catgaatcaa cctatcatca atcggaacca tttattgaag    3420
cccagaagcg agatttgatt tgatttgctt aacgctggct catgccctgc ttattgaaga    3480
tgaggagcga tcgctgaacc atggcaaaag ccgcctcccg tctagcttga aggcgttgac    3540
atcactctgt acttaggtct actgagtccg aaactttcag ccaaaaacca agggaattac    3600
agtgcttttt ccatcactga tcatcacgag gatatcgccg acatcaccga tggggaagat    3660
cgggctcgcc acttcgggct catgagcgct tgtttcggcg tgggtatggt ggcaggcccg    3720
ctttatcaga agccagacat taacgcttct ggagaaactc aacgagctgg acgcggatga    3780
acaggcagac atctgtgaat cgcttcacga ccacgctgat gagctttacc gcagctgcct    3840
cgcgcgtttc ggtgatgacg gtgaaaaacct ctgacacatg cagctcccgg agacggtcac   3900
agcttgtctg taagcggatg ccgggagcag acaagcccgt cagggcgcgt cagcgggtgt    3960
tggcgggtgt cggggcgcag ccatgaccca gtcacgtagc gatagcggag tgtatactgg    4020
cttaactatg cggcatcaga gcagattgta ctgagagtgc accatatgcg gtgtgaaata    4080
ccgcacagat gcgtaaggag aaaataccgc atcaggcgct cttccgcttc ctcgctcact    4140
```

```
gactcgctgc gctcggtcgt tcggctgcgg cgagcggtat cagctcactc aaaggcggta    4200
atacggttat ccacagaatc aggggataac gcaggaaaga acatgtgagc aaaaggccag    4260
caaaaggcca ggaaccgtaa aaaggccgcg ttgctggcgt ttttccatag gctccgcccc    4320
cctgacgagc atcacaaaaa tcgacgctca agtcagaggt ggcgaaaccc gacaggacta    4380
taaagatacc aggcgtttcc ccctggaagc tccctcgtgc gctctcctgt tccgaccctg    4440
ccgcttaccg gatacctgtc cgcctttctc ccttcgggaa gcgtggcgct ttctcaatgc    4500
tcacgctgta ggtatctcag ttcggtgtag gtcgttcgct ccaagctggg ctgtgtgcac    4560
gaaccccccg ttcagcccga ccgctgcgcc ttatccggta actatcgtct tgagtccaac    4620
ccggtaagac acgacttatc gccactggca gcagccactg gtaacaggat tagcagagcg    4680
aggtatgtag gcggtgctac agagttcttg aagtggtggc ctaactacgg ctacactaga    4740
aggacagtat ttggtatctg cgctctgctg aagccagtta ccttcggaaa aagagttggt    4800
agctcttgat ccggcaaaca aaccaccgct ggtagcggtg gtttttttgt ttgcaagcag    4860
cagattacgc gcagaaaaaa aggatctcaa gaagatcctt tgatcttttc tacggggtct    4920
gacgctcagt ggaacgaaaa ctcacgttaa gggattttgg tcatgagatt atcaaaaagg    4980
atctcgatcc cgcgaaatta atacgactca ctatagggag accacaacgg tttccctcta    5040
ccgggatccg cgctgctaaa caaagcccga aggaagctga agttggactg ctgccaccgc    5100
tgagcaataa ctagcataac cccttggggc ctctaaacgg gtcttgaggg gttttttgct    5160
gaaaggagga actatatgcg ccggatcgag atccttttaa attaaaaatg aagttttaaa    5220
tcaatctaaa gtatatatga gtaaacttgg tctgacagtt accaatgctt aatcagtgag    5280
gcacctatct cagcgatctg tctatttcgt tcatccatag ttgcctgact ccccgtcgtg    5340
tagataacta cgatacggga gggcttacca tctggcccgg cagtaccggc ataaccaagc    5400
ctatgcctac agcatccagg gtgacggtgc cgaggatgac gatgagcgca ttgttagatt    5460
tcatacacgg tgcctgactg cgttagcaat ttaactgtga taaactaccg cattaaagct    5520
tatcgatgat aagctgtcaa acatgagaat tcttgaagac gaaagggcct cttgcgggat    5580
atccgtctag atagtcatcg ctcatccctc acctcaaccg ttttgctgcc taacgaggta    5640
gtctaagacc gcgccaattc tgtcgagtgc cgcgctagtg gtacgttggt actcatcaag    5700
ccgtgcttcg gtttgtaatt gcctagcggt aagaatttca aagttctgct gatggatttg    5760
aactgtttgc aacaatgctt ctgcggttgc gcggagttct gtaaccgatg tgcggaggtc    5820
ggcattcact gcaacttggc tgtctaacgc agcttctatt ctggctagtc tgtcttcgct    5880
catgctgccc cctgcttgtc ttggttgtcc ttggcttctt gttccatttg ttctttaaca    5940
actcgtgtga gtaagaaagc ggcaagatta gccaacggtc ttccttcctc agacgctcgg    6000
ttagcaatcc attggtaaat ttcagcttct agagtgactg ctattctccc tttattggtt    6060
ggcatgacgt tggtgtact cctgagtcca tatcatacac cttgtgcaaa gagtgattga    6120
caaatgtact aatcggcagt aatagtatag agtgtattaa gtgtacaccg agtatatgac    6180
cgaagtacag accgtcaaca atggcactgt acccgttttt aatgcgggta aaagtgccag    6240
taaaaaactg cgtcgtaatc tgccttcgct gccatccaac ccaggcgcga gtgagatgag    6300
tgacgtgagc tattcctgca agttgatgc cagcccgact gtgtggatg ctttaccgct    6360
atacagcccg tttagcttat cggctgatgg cagttaccca atggtcaagg tgacgcgctc    6420
aaaagcctgc gaactgagaa ccgggaaatc aatcctggtc ggttcgggtc gttgctaccg    6480
```

-continued

```
agtgattttt tgatgacgat tcaccttaaa ggtgaatcgc actgattcct gtggactgcc      6540
tcgtaaacac ccactggaat cgcctacata atgaaggaca taattatcat gacagataga      6600
ccactcaccg agaaagagca gcaagtcatc tctgagtttg aaacggcgcg tcctggcttg      6660
ggtgcaattg ccgaacaaaa cattattaat aataatgtca ccggctgggc tgacattatc      6720
gctgatactc cggctgaaga actcgtcgcc aatgaaggga ctgccagcaa cagttttatg      6780
taccggagaa tcggctaatg aacgagcgac tttaccaagt atccttgaca gagttaacta      6840
aagttggtgt cccgcaagcg atagccgaac aagcgtcctt agtcgtagcc aacgatgacc      6900
ctacaaaacc caatcttggc agaacacccc aagcccaaga agcggtcaat gcggctatga      6960
ctcactacca cgctaatcaa cagggagtaa gtcaataatg agcgatcgcc agtttctatt      7020
tttaggactg gcggccgccg ccgtcagtct gtggtatcaa aaccagcaaa cagagttaca      7080
agcacagtta aatacctgtc gcgctcaact gcaaggcttt aaagacgggg tgatttatgg      7140
caaatgactg gattgaaatg cacttgccta gtcgtcaaca gctaggcagg ttttttactgt     7200 ggggattggg gcgattaact tttagtgcca gcatattttt atttgatgcc acgtcttacg      7260
ctttgcaaac agcgttaaca gtggtgaagt ggtgtagaca gtctgtatac aacttggtca      7320
aagtttacga ccaattgccc tatgctggca cttacgcgc ggctatcatt gacactaccg       7380
ccgtcaccct tgcggtcgaa ccagagggaa tcatcaccga cttgatgcaa gctctgtctg      7440
gtaagcactg tttaatagtt ggggatacgg gaactggcaa aagcaccata gcccaatggc      7500
ttgcttatca agtcgggggt gaggtgacag tctatgacgc tgacgctgca ccggacgagt      7560
ggacggggtt aaatgtcatt ggccgccgtg gtgactttga ggctatacag tcgggcatgg      7620
ctgctgacct ggaggaattg cagcgccgga ttgagctacg gggtgagtct ggggataagg      7680
cactagcagg aaaagaaagc gttttaattg ctgaagaact gccactgctg agagatgaag      7740
tcgagatagc aaccgaatgg ctcatcaaac acgccaggcg cggccgcaag cccaagcgtt      7800
ttgttattgg gctgactcaa gatgataatg tcaagaccttt aggtatcgag ggtgaaggcg      7860
gtgtccgtaa gtgttttagg atgttacgcc tgggtaagtt tgcagttagc cacgccaagt      7920
ccttaaaaga ccttgccctt gtggagtggt taaagtcggg gaaatatcgc tgcatggtgg      7980
atgatatgcc gtgtcagtta ccagatgtaa gcagttacaa aatggttatg ccccggttac      8040
agtctgtaac cagttttcag ccactccaaa cggctcaacc gacctcagaa caagcattac      8100
agcccgtttc atccctccca gaaccaagag atgaaccct agcaaaagtg gtaaaagcct       8160
gtctggaagc gggttttttca gaaagtaagg tgattaaaga aattttgggc tatcaaggcg      8220
ggcgttacca agaaggtaaa tcgctactgg aaaaacttaa ggatttgtag cggtgcggtt      8280
tagcattgac tgttacttgc tgtacaagga taattttctc aaagcggaat ggtgttaaac      8340
ccgattatta gagtcgtcat agcaaaagct tgaaaactgg caagggtgta ctggttttcg      8400 ttcttttttgg ttctaatggt tattttttac cagtttattt agtaataacc gagtgccaag      8460
tttcttgttt tacatagcaa agttagcaaa aaacattttg ccgtgaattt ccatctgtaa      8520
aaagcgtcac ggcgaaattc agtatttagt aaatacaaaa ataagtcaaa cgttgatcat      8580
gcaacacttt ggcgtacaat tgattgaaaa ttttgccgat aggcaaagtt taaattacct      8640
attaaaaaaa gttcagtgct tgggggttgt tatgctactt aaccgaagct aaataaaaca      8700
cacatacaca gaattgttac cacaccaaac accaaacaga aaaacgtgc tttgaattta      8760 tcaattaatg ggtgtagtta acaagtttta tttagcttca ggttaagcaa ataacattca      8820
ataggtactg gactgagaca tttccaaatg atcagcccag aaagcttaaa tacaaatgta      8880
```

-continued

```
tcactaaccc tgcttacaag ggaactacaa actgaaataa ttcttggcac ttacacggtc    8940
agggtacaca ctcgcattgg tcgagaacct tgtgcgcggt tgtggtattt gtgtcgagcg    9000
cttgataagg atgggtctgg tcatttaaca ttgccattgc ctgtagtaca gacgttctta    9060
gattgtagtg ataagtctgt ttaccgttgg ttacaggatg gaaaaaaaat aggagcattc    9120
cgccgctaca aaattaaagc aggaatgata accgtctact tgggcggtat gtttcaagtt    9180
tgttacaacc taaatttaaa aagatggggt gatgttgcag tagtgccttt agtccaagtg    9240
ttaagcgatt tacgctcact gaccactggc atagtcacac aaagctttca acaaaagagc    9300
cgctatgcgg ccaacagaca acttaaacca gagtacagaa acttttttgg agcgccacac    9360
ccgaacgagc tagtgaagga cacaaggcaa tcctctctta aatcgccaga gggggaagta    9420
ccttgtgtac ttcacattag ttcgtcgcgg atattcgtct caaaaagttt catccactat    9480
ggtacatctc aaaaagctgt cagctgtgag ttgggtattc acaagcgcac agtgcgacga    9540
catcaaaagc agctgggcat gaatcgccgt caactttgcc aagccaaaat tgagtacaat    9600
caactccggc acgctcggaa taatgacgcg tctgaatttt gggctttcac tggaaccaaa    9660
actgatatcg gttatcaagt tatgggtgac gcggttgtgt tttctgatgg cattgcccct    9720
ggagccaaaa agagacagcc caacacttac caaattgacg cgactgaatt tgacggtcga    9780
ttattcaaag tgggtgacaa ggtgttcatg aatcggtgca acatctaccg cgaacaattc    9840
accctaacaa cgatgtcagc agcacggcgg aagtaccatt tcaaactgtc acagtgccac    9900
ttcagcgaaa atcgagccgg tcgggtaggc aaccgttttg taataggttg ccactctggc    9960
gagatatgaa ggacattttt aagaattttt ttttagcgtg aaatgctgcg gcaaccagta   10020
tagtgatcga cacgaactag tgcagcatga ccgagagcct atagggtcgc ggcttttttgg  10080 caatagagat cgtatgcaga tcatgcgtag taacagacta acaagtaatg cttcctccat   10140
tgtggctaat gcttatcgtg ctttagttgc tgagcgtcca caaatattta atgctggtgg   10200
tgcttgtttc cacaaccgta accaagctgc ttgtatccgt gatttaggat ttattctgcg   10260
ttacgtcacc tattctgtat tagcaggtga tgctagtgtc atggacgatc gctgcttaaa   10320
tggtctgcgg gaaacatatc aagctttggg tactcctggc gatgcagtag catctggaat   10380
ccaaaaaatg aaagatgctg caattggcga tcgcggctca tattctcagt caaccgaaaa   10440
gtccgaggaa gcaatggggt gacggtaaag tctataacta aggcttaact gatgacctca   10500
aagtctgtct cgtgtccctc ctcatgaatt tggggaggga ttttttagtac actattacaa  10560 ataaacgtca cgattaaagt tacaggaaag cctgatccct atgactattg aagcagcaat   10620
gggagaagaa gccattaagg aaaatttaga acagttcctg attgttctat cagtttcttt   10680
aggcgtagca accctctccc aaatttccag tttctttcgc caaattccct atacgttact   10740
tttggttatt gttggcttag gattagcatt tgttgacatc cgactcgtta atctttctcc   10800
cgaattaatc ttagaaatct ttttaccccc actcttattt gaagcagcgt ggaatattcg   10860
ctggcgtaat ctcaaaaaaa atttatttcc cgttgtttta cttgccatta ttggggttgt   10920
tatatcagtg gttgggattg gttttagtct caactatttt agtggcttat ccctccccat   10980
tgctttgtta gtcggtgcta ttttagcagc aaccgatcct gttctgttta ttgctttatt   11040
ccgagaacta ggagtgggag aacgcttaac ggttctcatg aaggagaaa gtttatttaa    11100 tgatggtgtt gcgttgttg cttttagtct attagtggga attcccctcg gaacgcaaga   11160
attttcggtc actaataccc tcattcaatt tgttacccttt acaggattg gcatcggtgc   11220
```

```
ggggcgtta attggctttg gaatttctta tttaacgcag cgttttgatt tgcccttagt   11280
ggaacaatct ctgactttaa tttctgctta cggaacttat ttaatcactg aagaattagg   11340
cggttctggt gtgattggtg tggtgacagt cgggctaatt ttagggaact ttggctctcg   11400
cattggcatg aatccgcgga ctcgtttatt agtttcagaa ttttgggagt tcattgcttt   11460
tttcgtcaat tcaattgtct ttctcctgat tggcgatcaa atcaatattc gcggtttagc   11520
cgataatgga cagttaattt taatcacaat tatcgcccta gtgatcattc gtgctatcag   11580
tatttatggc ttaggaacaa ttagtaattt aatcacgaaa caggatatta gttggcaaga   11640
agaaacggtt ttatggtggg gcggtttacg cggttcggtt tccattgcgt tggcgttaag   11700
tgtccctgtc atgttagatg ggagacaaga tattattgaa gcggtgtttg gcgttgtcct   11760 tttaccttg ttagtccaag gattgacgat gcaaaccgtt attgagaagc taggcttaat   11820
cggcgatcgc gctcaacgtc gtacctatag cgaattaatc gcccgtcgca gtgcgctcga   11880
acgggtttta gcccacttaa atgcggttcc cccctccccc agtattgatg aagagtttaa   11940
agactaccaa agaggcttag tcaaaggaca actcgaaagc gtcaaccaag aaattacgaa   12000
gctacaacaa tcttatcccc agttacgatc tttagaacaa gaacaactgc gggaacaact   12060
tttagaagtg gaagcagaca cttacgctga gttgattcgg gcgggtaaac tcaataataa   12120
tctatctccc ttattgcaag aagtcctcgc caaaccagag tgagcggccg cttggcccag   12180
ggcttcccgg tatcaacagg gacaccagga tttatttatt ctgcgaagtg atcttccgtc   12240
acaggtattt attcgatgaa ttcgcgtgct ataattatac taattttta              12288
```

<210> SEQ ID NO 4
<211> LENGTH: 14338
<212> TYPE: DNA
<213> ORGANISM: Artificial Sequence
<220> FEATURE:
<223> OTHER INFORMATION: TK018 plasmid

<400> SEQUENCE: 4

```
tcgactctag aggatccgat aacatcaccg tcgttatcgt cgctttagaa taacgttccc     60
aaaatagctc atttccaact ggcaactcac aaccaaaaac cgcattttta gtaaatatac    120
tcagcaattt gttcaacctg agcatttttc ccatttgcaa cttgatacaa atatttttag    180
cagcaaattt tcctactgcc agcttagttt acataaattt tgtctgttga catcttgcac    240
acaataaggt atggcgcata taatgcgata ttactaccat taatttacta cctagtcatt    300
aacgtctccc gccagagaac agttttgaat aggtagtcaa ttttaggtat tgaacctgct    360
gtaaatttat taaatcgatg aatttccccg aaatctgctc tagcagactt gggttatata    420
ccagtaggct caggtgcaaa acaacaaagc acaaattta cccattaagg atataggcaa     480
tctgtcaaat agttgttatc tttcttaata cagaggaata atcaacaata tggggcaggt    540
actaactaaa gtcctatgcc tgtggggctt ctgtaaccga cataaccttt acgcgttgtc    600
ttttaggagt ctgttatgaa cggtaccagt aaaggagaag aactattcac tggagttgtc    660
ccaattcttg ttgaattaga tggtgatgtt aatgggcaca atttttctgt cagtggagag    720
ggtgaaggtg atgcaacata cggaaaactt accctttaaat ttatttgcac tactggaaaa    780
ctacctgttc catggccaac acttgtcact actttcgcgt atggtcttca atgctttgcg    840
agatacccag atcatatgaa acagcatgac tttttcaaga gtgccatgcc cgaaggttat    900
gtacaggaaa gaactatatt tttcaaagat gacgggaact acaagacacg tgctgaagtc    960
aagtttgaag gtgataccct tgttaataga atcgagttaa aaggtattga ttttaaagaa   1020
```

```
gatggaaaca ttcttggaca caaattggaa tacaactata actcacacaa tgtatacatc    1080
atggcagaca aacaaaagaa tggaatcaaa gttaacttca aaattagaca caacattgaa    1140
gatggaagcg ttcaactagc agaccattat caacaaaata ctccaattgg cgatggccct    1200
gtccttttac cagacaacca ttacctgtcc acacaatctg cccttcgaa agatcccaac     1260 gaaaagagag accacatggt ccttcttgag tttgtaacag ctgctgggat tacacatggc    1320
atggatgaac tatacaaata agagctcgaa ttgatccttt tgataatct catgaccaaa     1380 atcccttaac gtgagttttc gttccactga gcgtcagacc ccgtagaaaa gatcaaagga    1440
tcttcttgag atcctttttt tctgcgcgta atctgctgct tgcaaacaaa aaaaccaccg    1500
ctaccagcgg tggtttgttt gccggatcaa gagctaccaa ctcttttcc gaaggtaact     1560 ggcttcagca gagcgcagat accaaatact gtccttctag tgtagccgta gttaggccac    1620
cacttcaaga actctgtagc accgcctaca tacctcgctc tgctaatcct gttaccagtg    1680
gctgctgcca gtggcgataa gtcgtgtctt accgggttgg actcaagacg atagttaccg    1740
gataaggcgc agcggtcggg ctgaacgggg ggttcgtgca cacagcccag cttggagcga    1800
acgacctaca ccgaactgag atacctacag cgtgagctat gagaaagcgc cacgcttccc    1860
gaagggagaa aggcggacag gtatccggta agcggcaggg tcggaacagg agagcgcacg    1920
agggagcttc cagggggaaa cgcctggtat ctttatagtc ctgtcgggtt tcgccacctc    1980
tgacttgagc gtcgattttt gtgatgctcg tcagggggc ggagcctatg gaaaaacgcc     2040
agcaacgcgg cctttttacg gttcctggcc ttttgctggc cttttgctca catgttcttt    2100
cctgcgttat cccctgattc tgtggataac cgtattaccg cctttgagtg agctgatacc    2160
gctcgccgca gccgaacgac cgagcgcagc gagtcagtga gcgaggaagc ggaagagcgc    2220
ctgatgcggt attttctcct tacgcatctg tgcggtattt cacaccgcat atggtgcact    2280
ctcagtacaa tctgctctga tgccgcatag ttaagccagt atacactccg ctatcgctac    2340
gtgactgggt catggctgcg ccccgacacc cgccaacacc cgctgacgcg ccctgacggg    2400
cttgtctgct cccggcatcc gcttacagac aagctgtgac cgtctccggg agctgcatgt    2460
gtcagaggtt ttcaccgtca tcaccgaaac gcgcgaggca gctgcggtaa agctcatcag    2520
cgtggtcgtg aagcgattca cagatgtctg cctgttcatc cgcgtccagc tcgttgagtt    2580
tctccagaag cgttaatgtc tggcttctga taaagcgggc ctgccaccat cccacgccg     2640 aaacaagcgc tcatgagccc gaagtggcga gcccgatctt ccccatcggt gatgtcggcg    2700
atataggcgc cagcaaccgc acctgtggcg ccggtgatgc cgaagaact ccagcatgag     2760 atccccgcgc tggaggatca tccagccggc gtcccggaaa acgattccga agcccaacct    2820
ttcatagaag gcggcggtgg aatcgaaatc tcgtgatggc aggttgggcg tcgcttggtc    2880
ggtcatttcg aaccccagag tcccgctcag aagaactcgt caagaaggcg atagaaggcg    2940
atgcgctgcg aatcgggagc ggcgataccg taaagcacga ggaagcggtc agcccattcg    3000
ccgccaagct cttcagcaat atcacgggta gccaacgcta tgtcctgata gcggtccgcc    3060
acacccagcc ggccacagtc gatgaatcca gaaaagcggc cattttccac catgatattc    3120
ggcaagcagg catcgccatg ggtcacgacg agatcatcgc cgtcgggcat gcgcgccttg    3180
agcctggcga acagttcggc tggcgcgagc ccctgatgct cttcgtccag atcatcctga    3240
tcgacaagac cggcttccat ccgagtacgt gctcgctcga tgcgatgttt cgcttggtgg    3300
tcgaatgggc aggtagccgg atcaagcgta tgcagccgcc gcattgcatc agccatgatg    3360
```

```
gatactttct cggcaggagc aaggtgagat gacaggagat cctgccccgg cacttcgccc   3420
aatagcagcc agtcccttcc cgcttcagtg acaacgtcga gcacagctgc gcaaggaacg   3480
cccgtcgtgg ccagccacga tagccgcgct gcctcgtcct gcagttcatt cagggcaccg   3540
gacaggtcgg tcttgacaaa agaaccgggc gcccctgcg  ctgacagccg gaacacggcg   3600
gcatcagagc agccgattgt ctgttgtgcc cagtcatagc cgaatagcct ctccacccaa   3660
gcggccggag aacctgcgtg caatccatct tgttcaatca tgcgaaacga tcctcatcct   3720
gtctcttgat cagatcttga tcccctgcgc catcagatcc ttggcggcaa gaaagccatc   3780
cagtttactt tgcagggctt cccaaccta  ccagagggcg ccccagctgg caattccggt   3840
tcgcttgctg tccataaaac cgcccagtct agctatcgcc atgtaagccc actgcaagct   3900
acctgctttc tctttgcgct tgcgttttcc cttgtccaga tagcccagta gctgacattc   3960
atccggggtc agcaccgttt ctgcggactg gctttctacg tgttccgctt cctttagcag   4020
cccttgcgcc ctgagtgctt gcggcagcgt gaagctttct ctgagctgta acagcctgac   4080
cgcaacaaac gagaggatcg agaccatccg ctccagatta tccggctcct ccatgcgttg   4140
cctctcggct cctgctccgg ttttccatgc cttatggaac tcctcgatcc gccagcgatg   4200
ggtataaatg tcgatgacgc gcaaggcttg gctagcgac  tcgaccggtt cgctggtcag   4260
caacaaccat ttcaacgggg tctcacccctt gggcgggtta atctcctcgg ccagcaccgc   4320
gttgagcgtg atattcccct gttttagcgt gatgcgccca ctgcgcatag aaattgcatc   4380
aacgcatata gcgctagcag cacgccatag tgactggcga tgctgtcgga atggacgata   4440
tctagactta tatagacact aatatagaca atagtttata ctgctatcta tacaagtata   4500
gacattatct aatcatggca gacaaaactc tagccacttt tcgtattgac tccgaagaat   4560 gggagtctt  taaaaacctt gctagttctg aaagttccaa cgcctcagca ctgttaacag   4620
aatttgttcg ttggtatttg gcaggtaaca ggtttaatac tcccacttct cacactccca   4680
cccatctaga cacatccctc gaacagcgta tagacaatat tgaacaacgt ctagataaag   4740
tcacaactaa taatctagac aatatagatg aatttataga caagcgtata aagataatc    4800 tagcaacacg tctagacaaa cttcaatcgc aactggagga actgcgggga aaatcgaaag   4860
cccggtagtt caggcagaag gacaagctac cgggcaagac agaaagaata tagacaatag   4920
tatagacaat ctagacaaat tggaggcaac ccgcgatcgc accctcaata agctaaaaat   4980
gggtaggcag tcagccgccg ggaaagccat cgacgcgttt atcaaagagt tgcttcttc    5040 aggagacaac ataagctgaa gttatcaaaa ttctgtcctt acgtcgaaag cctgattta    5100 ccgtgcaacg attgataagc ttggctaaac tagcactggc tttcaacaga aagcatacga   5160
agaatcaata gatatagcca ccaattccac aaaatgcaga taacgtgtag agtattggaa   5220
tgcttaatct gtaagggtta tgaaggttaa cggcaacgga cgagccaaaa tactcacctc   5280
cgacgaactc aggcgactgt ttagcgacgg attcaccaca ccgcgcgatc gcgttttgtt   5340
tggcatctgt ctattcaccg gttgccgcgt tagtgaagct ctagcactcc aaacaacgga   5400
cattaaaggc gaaacactaa cctttaggaa gtctaccacc aaagggaaac tcaaacccg    5460 cgtggttgac atccagccag gactagccgc actcatggct gactatcacc ccaaaccggg   5520
aaccctgttc cctggcatga ggggagtcag cgataggctc acgcgatacg cggcggataa   5580
aatcttgcgc gatgcagcca aaagaatcgg gctagaaggc atcagtaccc acagtttccg   5640
ccgtactgcc ctcaaccaaa tgtctagcgc cggtatcccg ttgcgacaca ttcaagagat   5700
atccggtcac aatgaccttg gcacactgca acgctatctt gaagttacac ccgaacagcg   5760
```

```
acgcaaagct gtatccgtga ttggcttcta atgtacgcca acgctgttta gacccctatg    5820
ggtgctaaaa aaagacgcag cctaaacaca cgctctacac ttgaggatac ttttaaagta    5880
tccatcggtt ctagaactct gcacacgttc cggactttgg aaacgttata cctttccctg    5940
tgttgcagaa tgctgcaata tttcttcgac aagttaactt gtgactggtt taatattttc    6000
tcaaattgcc ccaaaacaac acgcctaaat ccttagacgt ttctgtggaa acctattagg    6060
tttttatcgc cgttgtttta gtggtaaacc caaagggttt gtatattctt gtatgaagtt    6120
cgactctgag ggttaagaag aatggctcgc cgaattttt acaagtggaa accgattaaa    6180
ggttaagggt caatcgggac gatgaatatt ttctaattgt gaccttctcc atctaataag    6240 cttctttgg ggttaaggtc gaagaaagta ctacgcatga tctgcatacg atctctattg    6300
ccaaaaagcc gcgaccctat aggctctcgg tcatgctgca ctagttcgtg tcgatcacta    6360
tactggttgc cgcagcattt cacgctaaaa aaaaattctt aaaaatgtcc ttcatatctc    6420
gccagagtgg caacctatta caaaacggtt gcctacccga ccggctcgat tttcgctgaa    6480
gtggcactgt gacagtttga atggtacttc ccgccgtgct gctgacatcg ttgttagggt    6540
gaattgttcg cggtagatgt tgcaccgatt catgaacacc ttgtcaccca ctttgaataa    6600
tcgaccgtca aattcagtcg cgtcaatttg gtaagtgttg ggctgtctct ttttggctcc    6660 agggcaatg ccatcagaaa acacaaccgc gtcacccata acttgataac cgatatcagt    6720
tttggttcca gtgaaagccc aaaattcaga cgcgtcatta ttccgagcgt gccggagttg    6780
attgtactca attttggctt ggcaaagttg acggcgattc atgcccagct gcttttgatg    6840
tcgtcgcact gtgcgcttgt gaatacccaa ctcacagctg acagcttttt gagatgtacc    6900
atagtggatg aaacttttg agacgaatat ccgcgacgaa ctaatgtgaa gtacacaagg    6960
tacttccccc tctggcgatt taagagagga ttgccttgtg tccttcacta gctcgttcgg    7020
gtgtggcgct ccaaaaagtt ttctgtactc tggtttaagt tgtctgttgg ccgcatagcg    7080
gctcttttgt tgaaagcttt gtgtgactat gccagtggtc agtgagcgta aatcgcttaa    7140
cacttggact aaaaggcacta ctgcaacatc accccatctt tttaaattta ggttgtaaca    7200
aacttgaaac ataccgccca gtagacggt tatcattcct gctttaattt tgtagcggcg    7260
gaatgctcct atttttttc catcctgtaa ccaacggtaa acagacttat cactacaatc    7320
taagaacgtc tgtactacag gcaatggcaa tgttaaatga ccagacccat ccttatcaag    7380
cgctcgacac aaataccaca accgcgcaca aggttctcga ccaatgcgag tgtgtaccct    7440
gaccgtgtaa gtgccaagaa ttatttcagt ttgtagttcc cttgtaagca gggttagtga    7500
tacatttgta tttaagcttt ctgggctgat catttggaaa tgtctcagtc cagtacctat    7560
tgaatgttat ttgcttaacc tgaagctaaa taaaacttgt taactacacc cattaattga    7620
taaattcaaa gcacgttttt tctgtttggt gtttggtgtg gtaacaattc tgtgtatgtg    7680
tgttttattt agcttcggtt aagtagcata acaaccccca agcactgaac tttttttaat    7740
aggtaattta aactttgcct atcggcaaaa ttttcaatca attgtacgcc aaagtgttgc    7800
atgatcaacg tttgacttat ttttgtattt actaaatact gaatttcgcc gtgacgcttt    7860
ttacagatgg aaattcacgg caaatgtttt ttgctaact ttgctatgta aaacaagaaa    7920
cttggcactc ggttattact aaataaactg gtaaaaaata accattagaa ccaaaagaa    7980 cgaaaaccag tacaccctg ccagttttca agcttttgct atgacgactc taataatcgg    8040
gtttaacacc attccgcttt gagaaaatta tccttgtaca gcaagtaaca gtcaatgcta    8100
```

```
aaccgcaccg ctacaaatcc ttaagttttt ccagtagcga tttaccttct tggtaacgcc    8160
cgccttgata gcccaaaatt tctttaatca ccttactttc tgaaaaaccc gcttccagac    8220
aggcttttac cacttttgct agggtttcat ctcttggttc tgggagggat gaaacgggct    8280
gtaatgcttg ttctgaggtc ggttgagccg tttggagtgg ctgaaaactg gttacagact    8340
gtaaccgggg cataaccatt ttgtaactgc ttacatctgg taactgacac ggcatatcat    8400
ccaccatgca gcgatatttc cccgacttta accactccac aagggcaagg tcttttaagg    8460
acttggcgtg gctaactgca aacttaccca ggcgtaacat cctaaaacac ttacggacac    8520
cgccttcacc ctcgatacct aaggtcttga cattatcatc ttgagtcagc ccaataacaa    8580
aacgcttggg cttgcggccg cgcctggcgt gtttgatgag ccattcggtt gctatctcga    8640
cttcatctct cagcagtggc agttcttcag caattaaaac gctttctttt cctgctagtg    8700
ccttatcccc agactcaccc cgtagctcaa tccggcgctg caattcctcc aggtcagcag    8760
ccatgcccga ctgtatagcc tcaaagtcac cacggcggcc aatgacattt aaccccgtcc    8820
actcgtccgg tgcagcgtca gcgtcataga ctgtcacctc accccgact tgataagcaa     8880
gccattgggc tatggtgctt ttgccagttc ccgtatcccc aactattaaa cagtgcttac    8940
cagacagagc ttgcatcaag tcggtgatga ttccctctgg ttcgaccgca agggtgacgg    9000
cggtagtgtc aatgatagcc gcgccgtaag tgccagcata gggcaattgg tcgtaaactt    9060
tgaccaagtt gtatacagac tgtctacacc acttcaccac tgttaacgct gtttgcaaag    9120
cgtaagacgt ggcatcaaat aaaaatatgc tggcactaaa agttaatcgc cccaatcccc    9180
acagtaaaaa cctgcctagc tgttgacgac taggcaagtg catttcaatc cagtcatttg    9240
ccataaatca ccccgtcttt aaagccttgc agttgagcgc gacaggtatt taactgtgct    9300
tgtaactctg tttgctggtt ttgataccac agactgacgg cggcggccgc cagtcctaaa    9360
aatagaaact ggcgatcgct cattattgac ttactccctg ttgattagcg tggtagtgag    9420
tcatagccgc attgaccgct tcttgggctt ggggtgttct gccaagattg ggttttgtag    9480
ggtcatcgtt ggctacgact aaggacgctt gttcggctat cgcttgcggg acaccaactt    9540
tagttaactc tgtcaaggat acttggtaaa gtcgctcgtt cattagccga ttctccggta    9600
cataaaactg ttgctggcag tcccttcatt ggcgacgagt tcttcagccg gagtatcagc    9660
gataatgtca gcccagccgg tgacattatt attaataatg ttttgttcgg caattgcacc    9720
caagccagga cgcgccgttt caaactcaga gatgacttgc tgctctttct cggtgagtgg    9780
tctatctgtc atgataatta tgtccttcat tatgtaggcg attccagtgg gtgtttacga    9840
ggcagtccac aggaatcagt gcgattcacc tttaaggtga atcgtcatca aaaaatcact    9900
cggtagcaac gacccgaacc gaccaggatt gatttcccgg ttctcagttc gcaggctttt    9960
gagcgcgtca ccttgaccat tgggtaactg ccatcagccg ataagctaaa cgggctgtat   10020
agcggtaaag catcccacac agtcgggctg gcatcaactt gcaggaata gctcacgtca   10080
ctcatctcac tcgcgcctgg gttggatggc agcgaaggca gattacgacg cagttttta   10140
ctggcacttt tacccgcatt aaaaacgggt acagtgccat tgttgacggt ctgtacttcg   10200
gtcatatact cggtgtacac ttaatacact ctatactatt actgccgatt agtacatttg   10260
tcaatcactc tttgcacaag gtgtatgata tggactcagg agtacaccaa acgtcatgcc   10320
aaccaataaa gggagaatag cagtcactct agaagctgaa atttaccaat ggattgctaa   10380
ccgagcgtct gaggaaggaa gaccgttggc taatcttgcc gctttcttac tcacacgagt   10440
tgttaaagaa caaatggaac aagaagccaa ggacaaccaa gacaagcagg gggcagcatg   10500
```

```
agcgaagaca gactagccag aatagaagct gcgttagaca gccaagttgc agtgaatgcc   10560
gacctccgca catcggttac agaactccgc gcaaccgcag aagcattgtt gcaaacagtt   10620
caaatccatc agcagaactt tgaaattctt accgctaggc aattacaaac cgaagcacgg   10680
cttgatgagt accaacgtac cactagcgcg gcactcgaca gaattggcgc ggtcttagac   10740
tacctcgtta ggcagcaaaa cggttgaggt gagggatgag cgatgactat ctagacggat   10800
atcccgcaag aggcccttc gtcttcaaga attcccgttt gactggcgat gctgctactg    10860
aaactaacaa ctacatcgac tacgcaatta acgccctcag ctaattttgc ttagtctagg   10920
cccggatggg taagtggttt tcagcttaag tgttgggttc tacttacttc tccgggtctt   10980
gctctatcta aaacattgg tttaacaagg agtattaggc aaatgccagt tactgtcgct    11040
gcctctcgct tgggaaccgc tgcgtttgac caatcacccg tcgaactgcg cgctaactat   11100
tctcgacctg caggtcgatc gacttttttg ctgaggtact gagtacacag ctaataaaat   11160
tgggcaatct ccgcgcctct atgacttgaa ggagagtgta ggggtatagg ggaaagatat   11220
cttttatcta catcacataa ataaaaaatt taatttgtcg ctctggctgc atatattgat   11280
gtatttttag ccataagttt tttagtgcca tgtaattata gtgattttta gcgatcgcag   11340 agcattttc cctggattta tcgcgatctc aaaaaaaatt tgcccgaagt atgacagatt    11400
gtcatatttg gtgtcgattt tatttaaaat gaataagaa aaataaaact acaggttagg    11460
agaacgccat gaattcttat actgtcggta cctatttagc ggagcggctt gtccagattg   11520
gtctcaagca tcacttcgca gtcgcgggcg actacaacct cgtccttctt gacaacctgc   11580
ttttgaacaa aaacatggag caggtttatt gctgtaacga actgaactgc ggtttcagtg   11640
cagaaggtta tgctcgtgcc aaaggcgcag cagcagccgt cgttacctac agcgtcggtg   11700
cgctttccgc atttgatgct atcggtggcg cctatgcaga aaaccttccg gttatcctga   11760
tctccggtgc tccgaacaac aatgatcacg ctgctggtca cgtgttgcat cacgctcttg   11820
gcaaaaccga ctatcactat cagttggaaa tggccaagaa catcacggcc gcagctgaag   11880
cgatttacac cccagaagaa gctccggcta aaatcgatca cgtgattaaa actgctcttc   11940
gtgagaagaa gccggtttat ctcgaaatcg cttgcaacat tgcttccatg ccctgcgccg   12000
ctcctggacc ggcaagcgca ttgttcaatg acgaagccag cgacgaagct tctttgaatg   12060
cagcggttga agaaaccctg aaattcatcg ccaaccgcga caagttgcc gtcctcgtcg    12120 gcagcaagct gcgcgcagct ggtgctgaag aagctgctgt caaatttgct gatgctctcg   12180
gtggcgcagt tgctaccatg gctgctgcaa aaagcttctt cccagaagaa acccgcatt    12240 acatcggtac ctcatggggt gaagtcagct atccgggcgt tgaaagacg atgaaagaag    12300 ccgatgcggt tatcgctctg gctcctgtct tcaacgacta ctccaccact ggttggacgg   12360
atattcctga tcctaagaaa ctggttctcg ctgaaccgcg ttctgtcgtc gttaacggcg   12420
ttcgcttccc cagcgttcat ctgaaagact atctgacccg tttggctcag aaagtttcca   12480
agaaaaccgg tgctttggac ttcttcaaat ccctcaatgc aggtgaactg aagaaagccg   12540
ctccggctga tccgagtgct ccgttggtca acgcagaaat cgcccgtcag gtcgaagctc   12600
ttctgacccc gaacacgacg gttattgctg aaaccggtga ctcttggttc aatgctcagc   12660
gcatgaagct cccgaacggt gctcgcgttg aatatgaaat gcagtggggt cacatcggtt   12720
ggtccgttcc tgccgccttc ggttatgccg tcggtgctcc ggaacgtcgc aacatcctca   12780
tggttggtga tggttccttc cagctgacgg ctcaggaagt cgctcagatg gttcgcctga   12840
```

```
aactgccggt tatcatcttc ttgatcaata actatggtta caccatcgaa gttatgatcc    12900
atgatggtcc gtacaacaac atcaagaact gggattatgc cggtctgatg gaagtgttca    12960
acggtaacgg tggttatgac agcggtgctg gtaaaggcct gaaggctaaa accggtggcg    13020
aactggcaga agctatcaag gttgctctgg caaacaccga cggcccaacc ctgatcgaat    13080
gcttcatcgg tcgtgaagac tgcactgaag aattggtcaa atggggtaag cgcgttgctg    13140
ccgccaacag ccgtaagcct gttaacaagc tcctctagtt tttggggatc aattcgagct    13200
ctctggataa aactaataaa ctctattacc catgattaaa gcctacgctg ccctggaagc    13260
caacggaaaa ctccaaccct tgaatacga ccccggtgcc ctgggtgcta atgaggtgga     13320
gattgaggtg cagtattgtg gggtgtgcca cagtgatttg tccatgatta ataacgaatg    13380
gggcatttcc aattaccccc tagtgccggg tcatgaggtg gtgggtactg tggccgccat    13440
gggcgaaggg gtgaaccatg ttgaggtggg ggatttagtg gggctgggtt ggcattcggg    13500
ctactgcatg acctgccata gttgtttatc tggctaccac aacctttgtg ccacggcgga    13560
atcgaccatt gtgggccact acggtggctt tggcgatcgg gttcgggcca agggagtcag    13620
cgtggtgaaa ttacctaaag gcattgacct agccagtgcc gggcccctttt tctgtggagg    13680 aattaccgtt ttcagtccta tggtggaact gagtttaaag cccactgcaa aagtggcagt    13740
gatcggcatt gggggcttgg gccatttagc ggtgcaattt ctccgggcct ggggctgtga    13800
agtgactgcc tttacctcca gtgccaggaa gcaaacggaa gtgttggaat tgggcgctca    13860
ccacatacta gattccacca atccagaggc gatcgccagt gcggaaggca aatttgacta    13920
tattatctcc actgtgaacc tgaagcttga ctggaactta tacatcagca ccctggcgcc    13980
ccagggacat ttccactttg ttggggtggt gttggagcct ttggatctaa atcttttttcc   14040 cctttttgatg ggacaacgct ccgtttctgc ctccccagtg ggtagtcccg ccaccattgc   14100
caccatgttg gactttgctg tgcgccatga cattaaaccc gtggtggaac aatttagctt    14160
tgatcagatc aacgaggcga tcgcccatct agaaagcggc aaagcccatt atcgggtagt    14220
gctcagccat agtaaaaatt agctctgcaa aggttgcttc tgggtccgtg gaatggtcaa    14280
acggagtcga tctcagttttt gatacgctct atctggaaag cttgacattc gatctgca     14338
```

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
ctccatctcc agtcctcagt tcag                                            24

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gtgtgacgaa attggaagct gc                                              22

<210> SEQ ID NO 7
<211> LENGTH: 49
<212> TYPE: DNA
<213> ORGANISM: Artificial Sequence

```
<220> FEATURE:
<223> OTHER INFORMATION: Primer

<400> SEQUENCE: 7
ctccatctcc agtcctcagt tcagtcacct tactttctga aaaacccgc         49

<210> SEQ ID NO 8
<211> LENGTH: 49
<212> TYPE: DNA
<213> ORGANISM: Artificial Sequence
<220> FEATURE:
<223> OTHER INFORMATION: Primer

<400> SEQUENCE: 8
gtgtgacgaa attggaagct gctccgtaag tgttttagga tgttacgcc         49

<210> SEQ ID NO 9
<211> LENGTH: 56
<212> TYPE: DNA
<213> ORGANISM: Artificial Sequence
<220> FEATURE:
<223> OTHER INFORMATION: Primer

<400> SEQUENCE: 9
gttatgcccc ggttacagtc tgtaacggcg tccagttttc agccactcca aacggc   56

<210> SEQ ID NO 10
<211> LENGTH: 56
<212> TYPE: DNA
<213> ORGANISM: Artificial Sequence
<220> FEATURE:
<223> OTHER INFORMATION: Primer

<400> SEQUENCE: 10
gccgtttgga gtggctgaaa actggacgcc gttacagact gtaaccgggg cataac   56

<210> SEQ ID NO 11
<211> LENGTH: 57
<212> TYPE: DNA
<213> ORGANISM: Artificial Sequence
<220> FEATURE:
<223> OTHER INFORMATION: Primer

<400> SEQUENCE: 11
gttatgcccc ggttacagtc tgtaacgctt agccagtttt cagccactcc aaacggc   57

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
gccgtttgga gtggctgaaa actggctaag cgttacagac tgtaaccggg gcataac   57

<210> SEQ ID NO 13
<211> LENGTH: 56
<212> TYPE: DNA
<213> ORGANISM: Artificial Sequence
<220> FEATURE:
<223> OTHER INFORMATION: Primer

<400> SEQUENCE: 13
gttatgcccc ggttacagtc tgtaactgcg cacagttttc agccactcca aacggc    56
```

<210> SEQ ID NO 14
<211> LENGTH: 56
<212> TYPE: DNA
<213> ORGANISM: Artificial Sequence
<220> FEATURE:
<223> OTHER INFORMATION: Primer

<400> SEQUENCE: 14
gccgtttgga gtggctgaaa actgtgcgca gttacagact gtaaccgggg cataac        56

<210> SEQ ID NO 15
<211> LENGTH: 44
<212> TYPE: DNA
<213> ORGANISM: Artificial Sequence
<220> FEATURE:
<223> OTHER INFORMATION: Primer

<400> SEQUENCE: 15
ggttacagtc tgtaacctcg ggcagttttc agccactcca aacg                    44

<210> SEQ ID NO 16
<211> LENGTH: 44
<212> TYPE: DNA
<213> ORGANISM: Artificial Sequence
<220> FEATURE:
<223> OTHER INFORMATION: Primer

<400> SEQUENCE: 16
gagtggctga aaactgcccg aggttacaga ctgtaaccgg ggca                    44

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
ggttacagtc tgtaacgcat gccagttttc agccactcca aacg                    44

<210> SEQ ID NO 18
<211> LENGTH: 44
<212> TYPE: DNA
<213> ORGANISM: Artificial Sequence
<220> FEATURE:
<223> OTHER INFORMATION: Primer

<400> SEQUENCE: 18
gagtggctga aaactggcat gcgttacaga ctgtaaccgg ggca                    44

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
cggttacagt ctgtaacggt cccagttttc agccactcca aacg                    44

<210> SEQ ID NO 20
<211> LENGTH: 44
<212> TYPE: DNA
<213> ORGANISM: Artificial Sequence
<220> FEATURE:
<223> OTHER INFORMATION: PRimer

```
<400> SEQUENCE: 20
ggagtggctg aaaactggga ccgttacaga ctgtaaccgg ggca                44

<210> SEQ ID NO 21
<211> LENGTH: 44
<212> TYPE: DNA
<213> ORGANISM: Artificial Sequence
<220> FEATURE:
<223> OTHER INFORMATION: Primer

<400> SEQUENCE: 21
ggttacagtc tgtaacgggc cacagttttc agccactcca aacg                44

<210> SEQ ID NO 22
<211> LENGTH: 44
<212> TYPE: DNA
<213> ORGANISM: Artificial Sequence
<220> FEATURE:
<223> OTHER INFORMATION: Primer

<400> SEQUENCE: 22
gagtggctga aaactgtggc ccgttacaga ctgtaaccgg ggca                44

<210> SEQ ID NO 23
<211> LENGTH: 44
<212> TYPE: DNA
<213> ORGANISM: Artificial Sequence
<220> FEATURE:
<223> OTHER INFORMATION: Primer

<400> SEQUENCE: 23
ggttacagtc tgtaacttcg aacagttttc agccactcca aacg                44

<210> SEQ ID NO 24
<211> LENGTH: 44
<212> TYPE: DNA
<213> ORGANISM: Artificial Sequence
<220> FEATURE:
<223> OTHER INFORMATION: Primer

<400> SEQUENCE: 24
gagtggctga aaactgttcg aagttacaga ctgtaaccgg ggca                44

<210> SEQ ID NO 25
<211> LENGTH: 44
<212> TYPE: DNA
<213> ORGANISM: Artificial Sequence
<220> FEATURE:
<223> OTHER INFORMATION: Primer

<400> SEQUENCE: 25
ggttacagtc tgtaacatgc atcagttttc agccactcca aacg                44

<210> SEQ ID NO 26
<211> LENGTH: 44
<212> TYPE: DNA
<213> ORGANISM: Artificial Sequence
<220> FEATURE:
<223> OTHER INFORMATION: Primer

<400> SEQUENCE: 26
gagtggctga aaactgatgc atgttacaga ctgtaaccgg ggca                44

<210> SEQ ID NO 27
```

```
<211> LENGTH: 44
<212> TYPE: DNA
<213> ORGANISM: Artificial Sequence
<220> FEATURE:
<223> OTHER INFORMATION: Primer

<400> SEQUENCE: 27
ggttacagtc tgtaacggat cccagttttc agccactcca aacg            44

<210> SEQ ID NO 28
<211> LENGTH: 44
<212> TYPE: DNA
<213> ORGANISM: Artificial Sequence
<220> FEATURE:
<223> OTHER INFORMATION: Primewr

<400> SEQUENCE: 28
gagtggctga aaactgggat ccgttacaga ctgtaaccgg ggca            44

<210> SEQ ID NO 29
<211> LENGTH: 44
<212> TYPE: DNA
<213> ORGANISM: Artificial Sequence
<220> FEATURE:
<223> OTHER INFORMATION: Primer

<400> SEQUENCE: 29
gttacagtct gtaacggtta cccagttttc agccactcca aacg             44

<210> SEQ ID NO 30
<211> LENGTH: 44
<212> TYPE: DNA
<213> ORGANISM: Artificial Sequence
<220> FEATURE:
<223> OTHER INFORMATION: Primer

<400> SEQUENCE: 30
agtggctgaa aactgggtaa ccgttacaga ctgtaaccgg ggca             44

<210> SEQ ID NO 31
<211> LENGTH: 44
<212> TYPE: DNA
<213> ORGANISM: Artificial Sequence
<220> FEATURE:
<223> OTHER INFORMATION: Primer

<400> SEQUENCE: 31
ggttacagtc tgtaacgcat gtcagttttc agccactcca aacg             44

<210> SEQ ID NO 32
<211> LENGTH: 44
<212> TYPE: DNA
<213> ORGANISM: Artificial Sequence
<220> FEATURE:
<223> OTHER INFORMATION: Primer

<400> SEQUENCE: 32
gagtggctga aaactgacat gcgttacaga ctgtaaccgg ggca             44

<210> SEQ ID NO 33
<211> LENGTH: 44
<212> TYPE: DNA
<213> ORGANISM: Artificial Sequence
<220> FEATURE:
<223> OTHER INFORMATION: Primer

<400> SEQUENCE: 33
```

-continued gttacagtct gtaacctgca gacagttttc agccactcca aacg　　　　　　　44

<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34
agtggctgaa aactgtctgc aggttacaga ctgtaaccgg ggca　　　　　　　44

<210> SEQ ID NO 35
<211> LENGTH: 44
<212> TYPE: DNA
<213> ORGANISM: Artificial Sequence
<220> FEATURE:
<223> OTHER INFORMATION: Primer

<400> SEQUENCE: 35
gttacagtct gtaaccagct gacagttttc agccactcca aacg　　　　　　　44

<210> SEQ ID NO 36
<211> LENGTH: 44
<212> TYPE: DNA
<213> ORGANISM: Artificial Sequence
<220> FEATURE:
<223> OTHER INFORMATION: Primer

<400> SEQUENCE: 36
agtggctgaa aactgtcagc tggttacaga ctgtaaccgg ggca　　　　　　　44

<210> SEQ ID NO 37
<211> LENGTH: 44
<212> TYPE: DNA
<213> ORGANISM: Artificial Sequence
<220> FEATURE:
<223> OTHER INFORMATION: Primer

<400> SEQUENCE: 37
ccggttacag tctgtaacgt accagttttc agccactcca aacg　　　　　　　44

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
tggagtggct gaaaactggt acgttacaga ctgtaaccgg ggca　　　　　　　44

<210> SEQ ID NO 39
<211> LENGTH: 44
<212> TYPE: DNA
<213> ORGANISM: Artificial Sequence
<220> FEATURE:
<223> OTHER INFORMATION: Primer

<400> SEQUENCE: 39
ggttacagtc tgtaacagta ctcagttttc agccactcca aacg　　　　　　　44

<210> SEQ ID NO 40
<211> LENGTH: 44
<212> TYPE: DNA

<213> ORGANISM: Artificial Sequence
<220> FEATURE:
<223> OTHER INFORMATION: Primer

<400> SEQUENCE: 40
gagtggctga aaactgagta ctgttacaga ctgtaaccgg ggca        44

<210> SEQ ID NO 41
<211> LENGTH: 44
<212> TYPE: DNA
<213> ORGANISM: Artificial Sequence
<220> FEATURE:
<223> OTHER INFORMATION: Primer

<400> SEQUENCE: 41
ggttacagtc tgtaacgggc tccagttttc agccactcca aacg        44

<210> SEQ ID NO 42
<211> LENGTH: 44
<212> TYPE: DNA
<213> ORGANISM: Artificial Sequence
<220> FEATURE:
<223> OTHER INFORMATION: Primer

<400> SEQUENCE: 42
gagtggctga aaactggagc ccgttacaga ctgtaaccgg ggca        44

<210> SEQ ID NO 43
<211> LENGTH: 44
<212> TYPE: DNA
<213> ORGANISM: Artificial Sequence
<220> FEATURE:
<223> OTHER INFORMATION: Primer

<400> SEQUENCE: 43
ccggttacag tctgtaactc gacagttttc agccactcca aacg        44

<210> SEQ ID NO 44
<211> LENGTH: 44
<212> TYPE: DNA
<213> ORGANISM: Artificial Sequence
<220> FEATURE:
<223> OTHER INFORMATION: Primer

<400> SEQUENCE: 44
tggagtggct gaaaactgtc gagttacaga ctgtaaccgg ggca        44

<210> SEQ ID NO 45
<211> LENGTH: 44
<212> TYPE: DNA
<213> ORGANISM: Artificial Sequence
<220> FEATURE:
<223> OTHER INFORMATION: Primer

<400> SEQUENCE: 45
gttacagtct gtaacccgct gacagttttc agccactcca aacg        44

<210> SEQ ID NO 46
<211> LENGTH: 44
<212> TYPE: DNA
<213> ORGANISM: Artificial Sequence
<220> FEATURE:
<223> OTHER INFORMATION: Primer

<400> SEQUENCE: 46
agtggctgaa aactgtcagc gggttacaga ctgtaaccgg ggca        44

<210> SEQ ID NO 47
<211> LENGTH: 44
<212> TYPE: DNA
<213> ORGANISM: Artificial Sequence
<220> FEATURE:
<223> OTHER INFORMATION: Primer

<400> SEQUENCE: 47
ggttacagtc tgtaacctta agcagttttc agccactcca aacg    44

<210> SEQ ID NO 48
<211> LENGTH: 44
<212> TYPE: DNA
<213> ORGANISM: Artificial Sequence
<220> FEATURE:
<223> OTHER INFORMATION: Primer

<400> SEQUENCE: 48
gagtggctga aaactgctta aggttacaga ctgtaaccgg ggca    44

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
ggttacagtc tgtaacacac gtcagttttc agccactcca aacg    44

<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50
gagtggctga aaactgacgt gtgttacaga ctgtaaccgg ggca    44

<210> SEQ ID NO 51
<211> LENGTH: 44
<212> TYPE: DNA
<213> ORGANISM: Artificial Sequence
<220> FEATURE:
<223> OTHER INFORMATION: Primer

<400> SEQUENCE: 51
ggttacagtc tgtaacgggc cccagttttc agccactcca aacg    44

<210> SEQ ID NO 52
<211> LENGTH: 44
<212> TYPE: DNA
<213> ORGANISM: Artificial Sequence
<220> FEATURE:
<223> OTHER INFORMATION: Primer

<400> SEQUENCE: 52
gagtggctga aaactggggc ccgttacaga ctgtaaccgg ggca    44

<210> SEQ ID NO 53
<211> LENGTH: 44
<212> TYPE: DNA
<213> ORGANISM: Artificial Sequence
<220> FEATURE:

<223> OTHER INFORMATION: Primer

<400> SEQUENCE: 53
ggttacagtc tgtaaccota ggcagttttc agccactcca aacg                44

<210> SEQ ID NO 54
<211> LENGTH: 44
<212> TYPE: DNA
<213> ORGANISM: Artificial Sequence
<220> FEATURE:
<223> OTHER INFORMATION: Primer

<400> SEQUENCE: 54
gagtggctga aaactgccta gggttacaga ctgtaaccgg ggca                44

<210> SEQ ID NO 55
<211> LENGTH: 44
<212> TYPE: DNA
<213> ORGANISM: Artificial Sequence
<220> FEATURE:
<223> OTHER INFORMATION: Primer

<400> SEQUENCE: 55
ggttacagtc tgtaacagat ctcagttttc agccactcca aacg                44

<210> SEQ ID NO 56
<211> LENGTH: 44
<212> TYPE: DNA
<213> ORGANISM: Artificial Sequence
<220> FEATURE:
<223> OTHER INFORMATION: Primer

<400> SEQUENCE: 56
gagtggctga aaactgagat ctgttacaga ctgtaaccgg ggca                44

<210> SEQ ID NO 57
<211> LENGTH: 44
<212> TYPE: DNA
<213> ORGANISM: Artificial Sequence
<220> FEATURE:
<223> OTHER INFORMATION: Primer

<400> SEQUENCE: 57
cggttacagt ctgtaacggc cacagttttc agccactcca aacg                44

<210> SEQ ID NO 58
<211> LENGTH: 44
<212> TYPE: DNA
<213> ORGANISM: Artificial Sequence
<220> FEATURE:
<223> OTHER INFORMATION: Primer

<400> SEQUENCE: 58
ggagtggctg aaaactgtgg ccgttacaga ctgtaaccgg ggca                44

<210> SEQ ID NO 59
<211> LENGTH: 44
<212> TYPE: DNA
<213> ORGANISM: Artificial Sequence
<220> FEATURE:
<223> OTHER INFORMATION: Primer

<400> SEQUENCE: 59
ggttacagtc tgtaacccat ggcagttttc agccactcca aacg                44

```
<210> SEQ ID NO 60
<211> LENGTH: 44
<212> TYPE: DNA
<213> ORGANISM: Artificial Sequence
<220> FEATURE:
<223> OTHER INFORMATION: Primer

<400> SEQUENCE: 60
gagtggctga aaactgccat gggttacaga ctgtaaccgg ggca            44

<210> SEQ ID NO 61
<211> LENGTH: 44
<212> TYPE: DNA
<213> ORGANISM: Artificial Sequence
<220> FEATURE:
<223> OTHER INFORMATION: Primer

<400> SEQUENCE: 61
gttacagtct gtaacagtcg accagttttc agccactcca aacg            44

<210> SEQ ID NO 62
<211> LENGTH: 44
<212> TYPE: DNA
<213> ORGANISM: Artificial Sequence
<220> FEATURE:
<223> OTHER INFORMATION: Primer

<400> SEQUENCE: 62
agtggctgaa aactggtcga ctgttacaga ctgtaaccgg ggca            44
```

METHODS FOR ANALYSES OF CYANOBACTERIAL RESTRICTION ENDONUCLEASES

REFERENCE TO SEQUENCE LISTING

This application contains a sequence listing submitted by EFS-Web, thereby satisfying the requirements of 37 C.F.R. §§1.821-1.825. The Sequence Listing, created on Dec. 15, 2013, is named "Sequence listing P0031.01.US ST25".

BACKGROUND

Cyanobacteria, also known as blue-green algae, are photosynthetic bacteria widespread in marine and freshwater environments. Cyanobacteria have simple growth requirements and grow to high densities by using light, carbon dioxide, and other inorganic nutrients for growth. They are useful hosts for the production of a wide range of compounds of interest including biofuels and other commodity chemicals, for example.

A barrier to using cyanobacteria for the production of compounds of interest is that efficient introduction of engineered vectors in cyanobacteria is hampered, or completely prohibited, due to the presence of restriction nucleases, see Thorsten H. et. al., Ch. 24, Synthetic Biology in Cyanobacteria: Engineering and Analyzing Novel Functions, In: Methods in Enzymology, Academic Press, 2011, Vol. 497, pp. 539-579, These nucleases can significantly decrease or completely prevent the uptake of exogenous DNA into cyanobacteria) cells, see for example Ruffing AM. et. al., Biotech. Bioeng., 2012, Vol. 109, pp. 2190-2199. Enzymes exhibiting nuclease activity are usually either endonucleolytic (an endonuclease) or exonucleolytic (an exonuclease) and may be either sugar specific or non-sugar specific. A catalog of restriction enzymes and their recognition sites is compiled and maintained by New England Biolabs in Ipswich, Massachusetts and can be accessed at http: //rebase.neb.com/ (REBASE).

In a prophetic embodiment, ROligos could be labeled with fluorescent dyes, radiolabels, antigens or other labels. The labels could be incorporated through post-labeling techniques or could be incorporated using pre-labeled nucleotides through polynucleotide synthetic techniques well known in the art, see for example oligonucleotide synthetic services available through Iba life sciences in Olivette, MO at http://www.lba-lifesciences.com/Service Custom oliqos.html and Shibata A., Molecules 2012 Feb. 29; 17(3)(42446-63 which discloses various techniques and references to techniques well known in the art of oligonucleotide labeling, Various restriction endonucleases exhibit restriction activity to varying degrees in various buffer conditions. Buffer conditions conunonly used for known restriction enzymes are mostly covered across four different buffers available through New England Biolabs, P1, P2, P3 and P4 buffers. Their compositions can be found at REBASE and are well known to those having skill in the art.

Cyanobacteria often contain one or more sequence-specific restriction endonucleases. These nucleases are almost always associated with their cognate methyltransferase. The methyltransferase methylates the host chromosomal and plasmid DNA to provide protection against its associated restriction enzyme. Endogenous cyanobacterial DNA is thus protected against specific nuclease activity by specific methylation, but foreign DNA is not methylated and is therefore targeted for destruction by the cyanobacterial nucleases, see Soper, B W et. al, J. Bacteriology 1994, 176(17):556-5570 and Elhai, J, et. al, J. Bacteriology 1997, 179(6): 1998-2005.

SUMMARY

Disclosed herein are methods that provide for the identification of cyanobacterial restriction endonucleases that are present in crude extracts. The method is based on specific PCR products (ROligos) which are designed with unique restriction endonuclease ("REN") recognition sequences leading to two easily distinguishable bands upon digestions with cyanobacterial crude extract. In addition, incubation of methylated ROligos in cyanobacterial extracts allows the determination of whether endonucleases present can be rendered ineffective by the provided methylation type. Hence, any methyltransferase that provides the desired type of methylation can be used to methylate and protect DNA in vitro or in vivo prior to transformation.

In an aspect, a method for identifying restriction endonucleases in a cyanobacterial cell is disclosed having the steps of a) incubating oligonucleotides from a ROligo library with a cyanobacterial cell extract from said cyanobacterial cell, wherein each oligonucleotide comprises a recognition sequence of a cyanobacterial restriction endonuclease, and b) analyzing digestion products of said oligonucleotides for digestion at said recognition sequences, and c) identifying restriction endonucleases in said cyanobacterial cell extract by analyzing digestion products of said oligonucleotides. In an embodiment, the method is can be used on cyanobacterial cells including *Prochlorococcus, Synechocystis, Synechococus, Chroococcales, Cyanobium, Oscillatoriales, Cyanobacterium, Pleurocapsales, Geitlerinema, Phormidiumn, Euhalothece, Anabaena, Lyngbya, Spirulina, Nostoc, Pleurocapsa,* and *Leptoiyngbya*. In another embodiment, the method discloses restriction endonucleases of step c) that are analyzed through depicting the results of digestion patterns at recognition sequences of said oligomcleotides from a ROligo library in an infographic table having all incubated oligonucleotides and all restriction endonucleases whose recognition sequences are part of the oligonucleotides, and wherein restriction endonucleases are identified from said cyanobacterial cell extract through the following stepwise manipulations of the digestion patterns depicted in the infographic table including the steps of a) first, restriction endonucleases which do not digest at least one of the oligonucleotides incubated with said cyanobacterial cell extract are removed from the infographic table, and b) second, restriction endonucleases which do not digest oligonucleotides from the ROligo library containing their recognition sequences, but are capable of recognizing other oligonucleotides that have been digested are removed from the infographic table, and c) third, restriction endonucleases in the cyanobacterial extract are identified as the restriction endonucleases not removed from the infographic table. In another embodiment, the uses an infographic table that is a digestion matrix. In an embodiment, the method is disclosed where each oligonucleotide comprises a left arm, a right arm, and a recognition sequence for a cyanobacterial restriction endonuclease wherein the oligonucleotide is produced through using a polymerase chain reaction wherein the left arm is a double stranded polynucleotide and the right arm is a double stranded polynucleotide and wherein the 5' end of a single stranded reverse primer of said left arm and the 5' end of a single stranded forward primer of the right arm overlap and make a recognition sequence for a cyanobacterial restriction endonuclease and wherein the left arm and the right arm primers use a template lacking any recognition sites for cyanobacterial restriction endonucleases. In yet another embodiment, the method uses a recognition sequence that is positioned asymmetrically along the length of each oligonucleotide such that digestion by the restriction endonuclease creates two digestion products of different sizes. In an embodiment, the method uses a template that is SEQ ID NO: 1 and wherein said left arm primer and said right arm primer include primers selected from the group consisting of SEQ ID NOs: 5-62.

In an aspect, a method for transforming cyanobacterial host cells with vectors is disclosed including a) incubating oligonucleotides from a ROligo library with a cyanobacterial cellular extract from the cyanobacterial host cell, wherein each oligonucleotide comprises a recognition sequence of a restriction endonuclease, and b) analyzing digestion products of the oligonucleotides for digestion at the recognition sequences, and c) identifying restriction endonucleases in said cyanobacterial cellular extract by analyzing digestion products of the oligonucleotides, and d) constructing a vector lacking said recognition sequences of the identified restriction endonucleases of step c), and e) transforming said cyanobacterial host cell with said vector of step d). In an embodiment, the method uses restriction endonucleases of step c) that are analyzed through depicting the results of digestion patterns at recognition sequences of said oligonucleotides from a ROligo library in an infographic table comprising all incubated oligonucleotides and all restriction endonucleases whose recognition sequences are part of the oligonucleotides, and wherein restriction endonucleases are identified from the cyanobacterial cell extract through the following stepwise manipulations of the digestion patterns depicted in said infographic table by the following steps: a) first, restriction endonucleases which do not digest at least one of the oligonucleotides incubated with said cyanobacterial cell extract are removed from said infographic table, and b) second, restriction endonucleases which do not digest oligonucleotides containing their recognition sequences, but are capable of recognizing other oligonucleotides that have been digested are removed from said infographic table, and c) third, restriction endonucleases in the cyanobacterial extract are identified as the restriction endonucleases not removed from said infographic table. In another embodiment, the method uses an infographic table that is a digestion matrix. In yet another embodiment, the method uses oligonucleotides wherein each oligonucleotide includes a left arm, a right arm, and a recognition sequence for a cyanobacterial restriction endonuclease, and wherein the oligonucleotide is produced through using a polymerase chain reaction wherein said left arm is a double stranded polynucleotide and the right arm is a double stranded polynucleotide and wherein the 5' end of a single stranded reverse primer of said left arm and the 5' end of a single stranded forward primer of said right arm overlap and comprise a recognition sequence for a cyanobacterial restriction endonuclease and wherein the left arm and said right arm primers use a template lacking any recognition sites for cyanobacterial restriction endonucleases. In yet another embodiment, the method uses oligonucleotides having a recognition sequence that is positioned asymmetrically along the length of the each oligonucleotide such that digestion by the restriction endonuclease creates two digestion products of different sizes. In an embodiment, the method uses a template that is SEQ ID NO: 1, and wherein the left arm primer and the right arm primer comprise single stranded polynucleotide primers are selected from the group consisting of SEQ ID NOs: 5-62.

In another aspect a method for transforming cyanobacterial host cells with vectors is disclosed and includes a) incubating oligonucleotides from a ROligo library with a cyanobacterial cellular extract from the cyanobacterial host cell, wherein each oligonucleotide comprises a recognition sequence of a restriction endonuclease, and b) analyzing digestion products of the oligonucleotides for digestion at the recognition sequences, and c) identifying restriction endonucleases in said cyanobacterial cellular extract by analyzing digestion products of the oligonucleotides, and d) methylating recognition sequences of the identified restriction endonucleases in a vector, and e) transforming the cyanobacterial host cell with said vector of step d). In an embodiment, the method uses recognition sequences in a vector that are methylated in step d) and are methylated by methyltransferases. In another embodiment, the method uses methyltransferases that are selected from the group consisting of M.CviPI, M.SssI and M.AvaII. In yet another embodiment, the method of uses restriction endonucleases of step c) that are analyzed through depicting the results of digestion patterns at recognition sequences of the oligonucleotides from a ROligo library in an infographic table comprising all incubated oligonucleotides and all restriction endonucleases whose recognition sequences are part of the oligonucleotides, and wherein restriction endonucleases are identified from the cyanobacterial cell extract through the following stepwise manipulations of the digestion patterns depicted in the infographic table including the steps of a) first, restriction endonucleases which do not digest at least one of the oligonucleotides incubated with the cyanobacterial cell extract are removed from said infographic table, and b) second, restriction endonucleases which do not digest oligonucleotides containing their recognition sequences, but are capable of recognizing other oligonucleotides that have been digested are removed from the infographic table, and c) third, restriction endonucleases in said cyanobacterial extract are identified as the restriction endonucleases not removed from the infographic table. In another embodiment, the method uses an infographic table that is a digestion matrix. In an embodiment, the method uses oligonucleotides wherein each oligonucleotide includes a left arm, a right arm, and a recognition sequence for a cyanobacterial restriction endonuclease, and wherein the oligonucleotide is produced through using a polymerase chain reaction wherein the left arm is a double stranded polynucleotide and the right arm is a double stranded polynucleotide and wherein the 5' end of a single stranded reverse primer of said left arm and the 5' end of a single stranded forward primer of the right arm overlap and make a recognition sequence for a cyanobacterial restriction endonuclease and wherein the left arm and the right arm primers use a template lacking any recognition sites for cyanobacterial restriction endonucleases. In yet another embodiment, the method uses oligonucleotides that have recognition sequences that are positioned asymmetrically along the length of each oligonucleotide such that digestion by the restriction endonuclease creates two digestion products of different sizes. In another embodiment, the method uses a template that is SEQ ID NO: 1, and wherein the left arm primer and the right arm primer comprise single stranded polynucleotide primers selected from the group consisting of SEQ ID NOs: 5-62.

In an aspect, a method for identifying restriction endonucleases is disclosed having the steps of a) incubating oligonucleotides including a ROligo library with a cyanobacterial cell extract wherein each oligonucleotide of said ROligo library includes a recognition sequence of a restriction endonuclease, and b) wherein each oligonucleotide of said ROligo library is labeled with a unique marker that is uniquely visualized, and c) analyzing digestion products of said ROligo library of oligonucleotides for digestion at said recognition sequences by visualizing said markers, and d) identifying restriction endonucleases in said cyanobacterial cell extract by correlating said visualized markers of step c) with their corresponding oligonucleotides. In an embodiment, the method uses oligonucleotides wherein each oligonucleotide includes a left arm, a right arm, a marker, and a recognition sequence for a cyanobacterial restriction endonuclease wherein the oligonucleotide is produced through using a polymerase chain reaction wherein the left arm is a double stranded polynucleotide and the right arm is a double stranded polynucleotide and wherein the 5' end of a single stranded reverse primer of the left arm and the 5' end of a single stranded forward primer of the right arm overlap and comprise a recognition sequence for a cyanobacterial restriction endonuclease and wherein the left arm and the right arm primers use a template lacking any recognition sites for cyanobacterial restriction endonucleases. In another embodiment, the method uses oligonucleotides wherein the recognition sequence is positioned asymmetrically along the length of said each oligonucleotide such that digestion by the restriction endonuclease creates two digestion products of different sizes. In yet another embodiment, the method uses a template that is SEQ ID NO: 1, and wherein the left arm primer and the right arm primer comprise single stranded polynucleotide primers selected from the group consisting of SEQ ID NOs: 5-62, and wherein the marker is selected from the group consisting of fluorescent dyes, radiolabels, and antigens.

BRIEF DESCRIPTION OF DRAWINGS

FIG. 2 depicts a list of known cyanobacterial restriction endonucleases, their recognition sequences and the sequences that were used to construct ROligos.

FIG. 3 depicts sequences of primers used to construct the left and right arms of various ROligos.

FIG. 6 is an infographic chart depicting the theoretical capability of various nucleases to produce a double band pattern when acting upon various ROligos.

FIG. 14 is an infographic chart depicting the results of incubation of various ROligos as a step in the exemplification of the ROligos method for identifying restriction enzymes in a first *Cyanobacterium* strain extracts.

FIG. 15 is a table depicting cyanobacterial strains analyzed for restriction endonuclease activity using the ROligo method.

DETAILED DESCRIPTION

Figure 1:
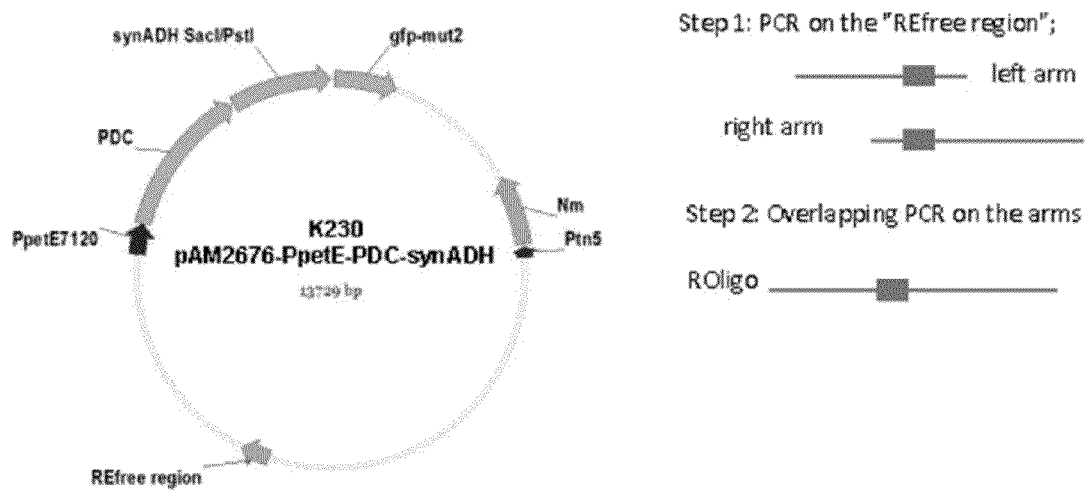
FIG. 1 depicts a plasmid map of K230 (left portion of FIG. 1) and a schematic depiction of ROligo construction (right portion of FIG. 1).

Disclosed herein are methods for the identification of restriction endonucleases in cyanobacterial extracts. Identifying restriction endonucleases present within a cyanobacterial strain allows for protection against digestion of introduced vectors or other constructs. In an embodiment, engineered vectors to be used for transformation of a cyanobacterial strain do not contain the recognition site of restriction endonucleases identified in that strain. In another embodiment, engineered vectors to be used for transformation are protected against digestion (restriction) by methylating at extant recognition sites of the identified restriction endonucleases.

Definitions

The section headings used herein are for organizational purposes only and are not to be construed as limiting the described subject matter in any way. When definitions of terms in incorporated references appear to differ from the definitions provided in the present teachings, the definition provided in the present teachings shall control. Slight and insubstantial deviations from metrics used herein are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Generally, nomenclatures utilized in connection with, and techniques of, cell and tissue culture, molecular biology, protein and nucleotide/polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The nomenclatures utilized in connection with, and the laboratory procedures and techniques of described herein are those well-known and commonly used in the art, see, e.g., Sambrook et al., Molecular Cloning: A Laboratory Manual (Third ed., Cold Spring Harbor Laboratory Press, Cold Spring Harbor, N.Y. 2000). Standard recombinant DNA procedures were used for gene cloning, plasmid isolation, and electroporation. Manufacturer protocols and standard methods (Sambrook et al., 2000) were followed for DNA purification (e.g., Qiagen, Valencia, Calif.), restriction endonuclease digestion (NEB, Ipswich, Mass.), and DNA amplification using DNA polymerases (NEB, Ipswich, Mass.).

As used in accordance with the embodiments provided herein, the following terms, unless otherwise indicated, shall be understood to have the following meanings:

The term "nucleic acid" and "nucleic acid molecule" refer to natural nucleic acid sequences such as DNA (deoxyribonucleic acid) and RNA (ribonucleic acid), artificial nucleic acids, analogs thereof, or combinations thereof.

The term "oligonucleotide" and "polynucleotide" are synonymous as used herein with each referring to nucleic acids comprising more than one nucleotide. Oligonucleotides and polynucleotides as used herein may be single stranded, double stranded, or a mixture of both single and double strands.

The term "nuclease" applies to enzymes that cleave a phosphodiester bond between nucleotides in a polynucleotide.

The term "recognition sequence" refers to the sequence of polynucleotides comprising the substrate of a nuclease.

The term "endonuclease" applies to nucleases that break nucleic acid chains somewhere in the interior, rather than at the ends, of a polynucleotide.

The term "exonuclease" applies to nucleases that functions by removing nucleotides from the ends of a polynucleotide.

The term "restriction endonuclease" refers to an endonuclease that "restricts", meaning "digests", meaning "cuts", meaning breaks/cleaves phosphodiester bonds between nucleotides on each strand (parallel and antiparallel) in a polynucleotide, thus creating smaller polynucleotides. The terms "restricts", "digests" and "cleaves" as used herein are synonymous when used in the context of nuclease activity.

The term "plasmid" refers to a circular nucleic acid vector. Generally, plasmids contain an origin of replication that allows many copies of the plasmid to be produced in a bacterial (or sometimes eukaryotic) cell.

A "shuttle vector" refers to a vector which can propagate in two different host species.

The term "construct" as used herein refers to a recombinant nucleic acid molecule that has been generated for the purpose of the expression of a specific nucleotide sequence or sequences, or is to be used in the construction of other recombinant nucleotide sequences. In general, "construct" is used herein to refer to a recombinant nucleic acid molecule. Generally, the term "construct" and the term "vector" are synonymous as used herein.

The term "host cell" as used herein refers to a cell into which DNA can be introduced by any appropriate means (e.g. natural uptake, transformation, transfection, electroporation, and conjugation).

The term "transformation" as used herein refers to a permanent or transient genetic change, e.g., a permanent genetic change induced in a cell following incorporation of non-host nucleic acid sequences.

The term "ROligo" as used herein refers to an oligonucleotide containing a recognition sequence of at least one restriction endonuclease.

The term "ROligo library" refers to multiple ROligos. A ROligo library can consist of a group of ROligos that each individually contain a recognition sequence of a restriction endonuclease from a particular organism and the group of ROligos together make up a ROligo library whose ROligos together contain all of the known recognition sequences of that particular organism.

The terms "information graphics" or "infographics" are used herein refer to graphic visual representations of information, data or knowledge intended to present complex information quickly and clearly. Infographics utilize graphics to enhance the human visual system's ability to see patterns and trends. As used herein, an example of an infographic is a digestion matrix.

The term "digestion matrix" as used herein refers to an infographic table depicting the theoretical capability of various restriction endonucleases to cleave a ROligo oligonucleotide to the double band pattern. A digestion matrix can be used as an infographic. A digestion matrix depicting the theoretical results of the digestion of all constructed oligonucleotides can be manipulated through the application of a set of rules to afford the identity of active restriction endonuclease in a cyanobacterial extract.

The following figures, description, and examples illustrate certain embodiments of the present disclosure in detail. Those of skill in the art will recognize that there are numerous variations and modifications that are encompassed by its scope. Accordingly, the description of certain embodiments should not be deemed to limit the scope of the present disclosure.

Sequencing Method of Determining Restriction Endonucleases

Incubation of a plasmid in a cyanobacterial extract often results in a large number of bands, especially if enzymes with 4-5 bp recognition sequences like R.HaeIII which has a recognition sequence of GGCC or R.AvaII which has a recognition sequence of GGWCC (where W is A or T) are active. Gel isolation and cloning of every fragment after treatment with mung bean nuclease to degrade both 5' and 3' single-stranded extensions from the ends of DNA molecules, to generate blunt ends to enable ligation for sequencing would be very time and labor consuming. In case of multiple cutting enzymes, the same enzyme would be identified repeatedly, rendering most of the work non-informative.

As an example of the sequencing method of identifying recognition sequences, a plasmid, K230 (SEQ ID NO: 1) was incubated with a *Chlorogloeopsis* strain extract. A plasmid map of K230 is depicted in the left portion of FIG. 1. The digested plasmidial DNA was subjected to sequencing reactions without gel purification of individual bands. For the sequencing reaction, a set of spanning primers (with around 1 kb distance between two adjacent primers) covering the whole K230 plasmid was used because the cleavage points were not known. FIG. 2 depicts the result of the sequencing reaction for a digested portion of the K230 plasmid. As depicted in FIG. 2 for K230 digested with a *Chlorogloeopsis* strain crude extract, a cleavage point was identified when the sequencing signal dropped sharply at an R.SphI site.

Through multiple rounds of using the labor-intensive and time-consuming sequencing method, enzymes R.BlpI and R.SphI in a *Chlorogloeopsis* strain. R.AvaII and R.MstI in a second *Nostoc* strain and R.AcyI in a second *Cyanobacterium* strain were identified.

The sequencing method for identifying active restriction endonucleases in a cyanobacterial extract has at least two disadvantages. First, the DNA sent to be sequenced contained a vast amount of cyanobacterial genomic DNA from the extract incubation, so the background often was high and rendered many sequencing reactions non-readable and thus required several repetitions reliable sequencing information. Secondly, the sequencing method relies on complete digestion at least at some cleavage points as even traces of undigested plasmid would allow a read-through instead of a signal drop. Therefore, the sequencing method can only be reliably used if completeness of digestion is assured.

Both gel isolation of bands with subsequent cloning and the direct sequencing method share the same disadvantages as the same enzyme might be identified repeatedly. A different method is disclosed herein that improves identification of restriction endonucleases in cyanobacterial extracts, reduces work load, simplifies and accelerates analyses to provide information about whether all restriction enzymes that are present in a cellular extract have been identified.

ROligo Method for Identification of Restriction Endonucleases

In an embodiment, a method is disclosed (herein referred to as the "ROligo" method "R" from restriction site, "Oligo" from oligonucleotide) to identify restriction endonucleases in cellular extracts. In an embodiment, the ROligo method disclosed herein is an improvement over isolating and sequencing digested polynucleotides using the sequencing method in order to identify restriction endonucleases present in a cell.

In an embodiment, ROligos are an oligonucleotide with one introduced recognition site for a known cyanobacterial restriction enzyme that are constructed by performing overlapping PCR on two sequences (the "left arm" and "right arm"), whose ends contain the recognition sequence of a given restriction endonuclease to be introduced between the two arms, see the right portion of FIG. 1. In another embodiment, ROligos contain recognition sequences for restriction endonucleases from any given organism such as, for example, *E. coli*.

In an embodiment, a collection of multiple different ROligos is referred to as a ROligo library. In an embodiment, a ROligo library contains ROligos designed to test for restriction endonucleases from a particular organism. As an example, a ROligo library could be created containing ROligos that cumulatively contain all of the known recognition sequences of cyanobacterial restriction endonucleases as listed in REBASE or any other catalog listing cyanobacterial restriction endonucleases.

In an embodiment, the ROligo method includes incubating various combinations of different ROligos from a ROligo library in a cellular extract and observing a cleavage pattern of the ROligos by agarose gel electrophoretic analysis. The cleavage pattern (pattern of bands of ethidium bromide stained polynucleotides as visualized in the agarose gel using ultraviolet light) indicates the occurrence of enzymes recognizing the introduced restriction sites. Individual restriction endonucleases can then be identified by subsequent incubation of single ROligos from the digested ROligo pool. Thus, in an embodiment of the ROligo method, specific restriction endonucleases can be rapidly identified without additional isolation and sequencing of digested DNA. Additionally, the ROligo method, in contrast to the sequencing method, does not rely on complete digestion of a polynucleotide sequence, i.e. even if only a fraction of the incubated ROligo molecules are digested at the introduced recognition site, the double band pattern will occur.

Figure 13:
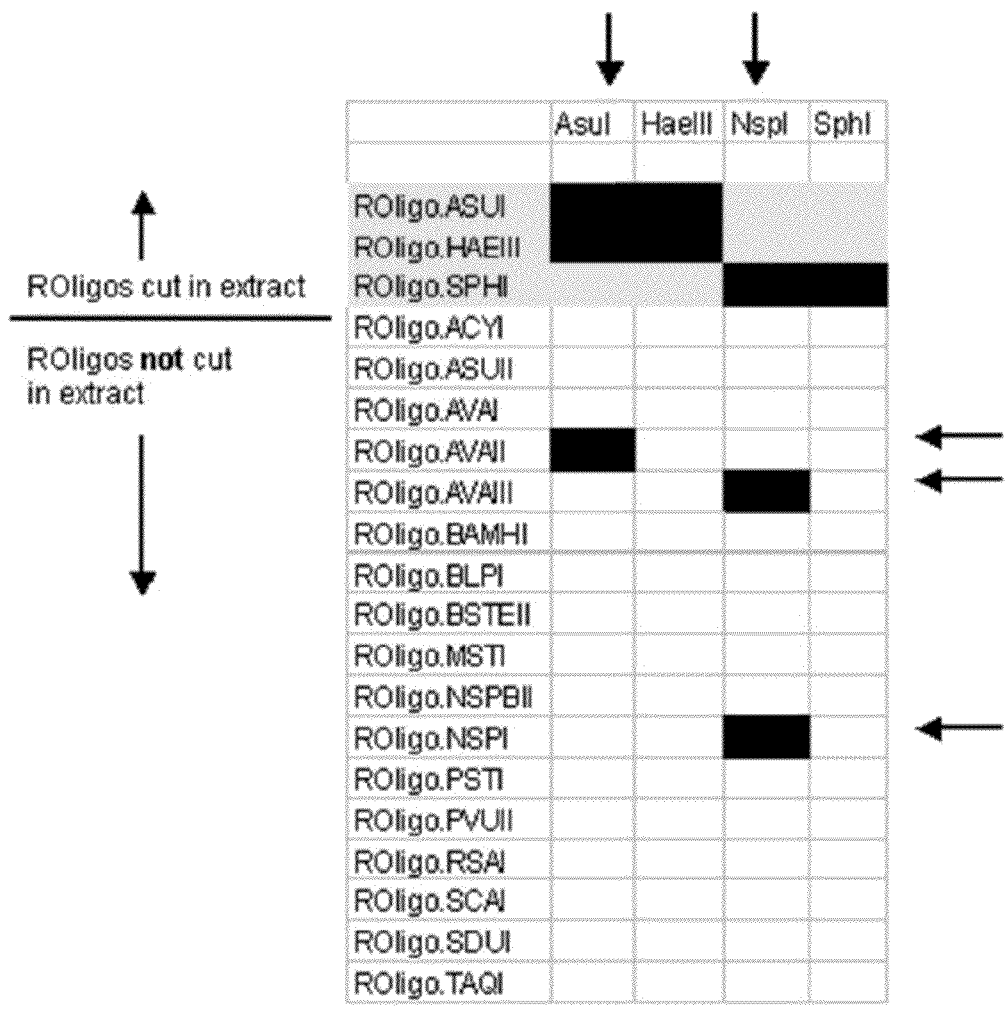
FIG. 13 is an infographic chart depicting the results of incubation of various ROligos as a step in the exemplification of the ROligos method for identifying restriction enzymes in a first *Cyanobacterium* strain extract.

FIG. 13 depicts a list of known cyanobacterial restriction endonucleases and their recognition sequences that were used to construct ROligos. The sequence which is introduced between the ROligo arms is in usually identical to the recognition sequence of the corresponding restriction endonuclease. However, in cases of a degenerate recognition sequence, a specific sequence among multiple potential sequences is chosen. Some recognition sequences are preceded (e.g. R.AsuI) or followed (e.g. R.SalI) by additional base(s), here a T base, in order to disrupt otherwise emerging recognition sites of further nucleases in the overlap between the introduced site and the adjacent arm sequence. As depicted in the FIG. 1 in the plasmid of K230, contains a "REfree region" from base pairs 7550 to 7926 of SEQ ID NO: 1 that is devoid of recognition sites for known cyanobacterial enzymes. In an embodiment, this REfree region is used as the template for a two-step PCR protocol to construct the left and right arms of ROligos with specific recognition sites and lacking all other known cyanobacterial recognition sequences elsewhere within the ROligo polynucleotide. Depicted as boxes in the right portion of FIG. 1, ROligo recognition sequences are introduced at an uncentered, asymmetrical position in the ROligo.

The design of a ROligo library needs to be carefully considered in order to create as many ROligos that are only digested by a single restriction endonuclease to the double band pattern. FIG. 2 depicts known cyanobacterial restriction enzymes, their general recognition sequence and the specific sequence used to generate the recognition sequence in the corresponding ROligo. In an embodiment, a ROligo library can be created using the recognition sequences of the cyanobacterial restriction endonucleases as depicted in FIG. 2. As an example of decreasing the number of ROligos cut by more than one known cyanobacterial enzyme, the ROligos used in embodiments described herein were designed keeping in mind to following information. As depicted in FIG. 2, the asterisk (*) denotes that these restriction enzymes, found in a second round of literature search after constructing the first ROligos, cut within the arms of the ROligos and, therefore, do not produce the indicative double band pattern of an embodiment of the ROligo method. The superscripted 1 denotes that a blocking base, T, was inserted before the recognition sequence to disrupt an otherwise emerging ApaI site at the junction to the left arm. The superscripted 2 denotes that a blocking base, T, was inserted before the recognition sequence to disrupt an otherwise emerging AsuI site at the junction to the left arm. The superscripted 3 denotes that a blocking base, T, was inserted before the recognition sequence to disrupt an otherwise emerging GC stretch at the junction to the left arm. As the enzyme's recognition site contains a GC, methylation sensitivity could be checked by M.CviPI. Without the additional T base, a possible blockage might result from the outer C, which could only be methylated in specific nucleotide surroundings. The superscripted 4 denotes a blocking base, T, that was inserted after the recognition sequence to disrupt an otherwise emerging CG stretch at the junction to the right arm. As the enzyme's recognition site contains a CG, methylation sensitivity could be checked by M.SssI. Without the additional T base, a possible blockage might result from the outer C, which could only be methylated in specific nucleotide surroundings.

Use of ROligo Method on Cyanobacteria

In an embodiment, the ROligo method disclosed herein is used to identify restriction endonucleases in cyanobacterial genera, species and/or strains. Non-limiting examples of cyanobacterial genera, species and strains that are members thereof, upon which the ROligo method can be used include, but are not limited to, *Prochlorococcus, Synechocystis, Synechococcus, Chroococcales, Cyanobium, Oscillatoriales, Cyanobacterium, Chlorophyta, Pleurocapsales, Geitlerinema, Phormidium, Euhalothece, Anabaena, Lyngbya, Spirulina, Nostoc, Pleurocapsa,* and *Leptolyngbya*. In another embodiment of the ROligo method, cell and cellular extracts to be tested for restriction endonuclease activity include all bacteria and Archaea. In an embodiment, certain eukaryotic cells may be tested by embodiments of the ROligo method.

Development of the ROligo Method

In contrast to other methods used to identify restriction endonucleases, the ROligo method does not rely on complete digestion of the polynucleotides incubated with cellular extracts or other solutions containing restriction endonucleases, i.e. even if only a fraction of the polynucleotide molecules are cleaved at the introduced restriction recognition site, the double band pattern will occur While the sequencing method uses a plasmid with many restriction sites and aims to identify the cleavage point, the ROligo method uses an oligonucleotide with exactly one recognition site for a known cyanobacterial enzyme. In an embodiment of the ROligo method, about 27 different ROligos were constructed by overlapping PCRs using primers having SEQ ID NOs: 5-62 as depicted in FIG. 3. The strand backbone for the ROligo originated from the K230 plasmid (see FIG. 1) which contains a sequence of 360 bp that shows no recognition site for any of the known cyanobacterial restriction endonucleases, see FIG. 2. In an embodiment of the ROligo method, this K230 stretch is used and a known cyanobacterial restriction site is inserted at an uncentered, asymmetric position resulting in a PCR-derived DNA fragment of about 380 bp length, see right side of FIG. 1. In an embodiment, cleavage of the generated ROligos results in a double band of about 216 and about 166 bp that are generated by digestion of a ROligo at the recognition sequence, the approximate length of the individual arms. These bands are readily discernible by using a lane containing size markers as one ROligo cleavage band lies above and one ROligo cleavage band lies below the 200 bp marker band of the size marker standards.

Figure 4:
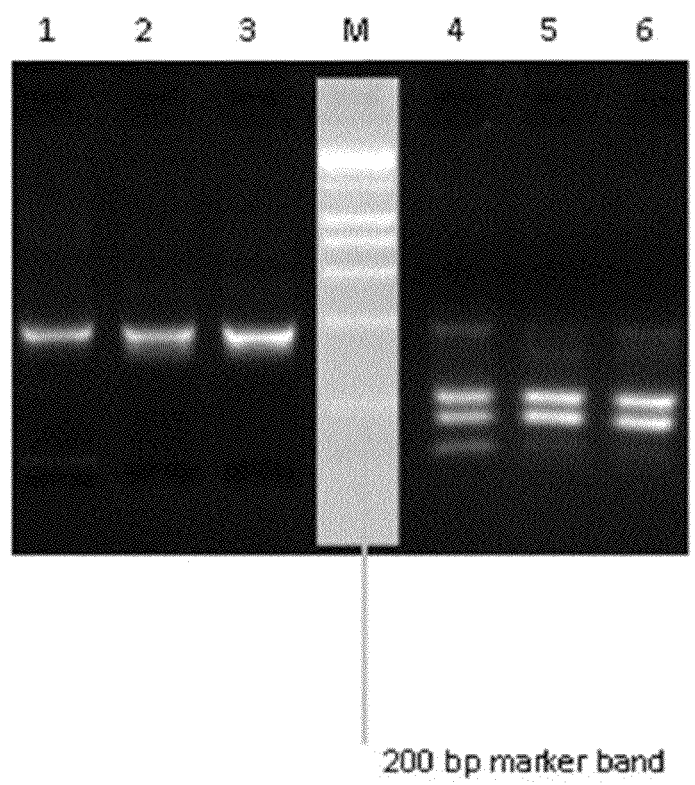
FIG. 4 depicts an agarose gel analysis of ROligo.AvaI. ROligo.AvaII and ROligo.SphI undigested or digested with commercially available, corresponding restriction nucleases.

FIG. 4 depicts digested and undigested ROligos analyzed by agarose gel electrophoresis stained with ethidium bromide and visualized under ultraviolet light. Lanes 1-3 contain, respectively, undigested ROligos, ROligo.AvaI, ROligo.AvaII, and ROligo.SphI. Lanes 4-6, contain, respectively, ROligo.AvaI digested with R.AvaI (R. stands for restriction endonuclease, thus R.AvaI is restriction endonuclease AvaI), ROligo.AvaII digested with R.AvaII, and ROligo.SphI digested with R.SphI. Lane M contains a size marker.

The ROligos with introduced recognition sites for R.AvaI (lane 1), R.AvaII (lane 2) and R.SphI (lane 3) were constructed by PCR. The undigested PCR products (lanes 1-3) depict a full length 380 bp band. ROligos were digested with appropriate commercially available enzymes (lanes 4-6) and the desired double band at 216/166 bp was observed.

For some ROligos, digestion with commercially available enzymes leaves a faint undigested band (see FIG. 4, lane 4). This may be due to the use of three consecutive PCR reactions in the ROligo construction process using a polymerase with relatively low fidelity such as DreamTaq polymerase. To reduce the number of such undigestable PCR molecules, a polymerase with higher fidelity, Pwo available from Roche Applied Science, was used for PCR amplification of the ROligos.

Digestion patterns other than the double band pattern of 216/166 that are created by digestion of a ROligo at the introduced recognition sequence are not investigated. Thus, restriction enzymes that cut at sites other than the introduced recognition sequence will be missed.

Digestions of Plasmids with Cyanobacterial Extracts

Figure 5:
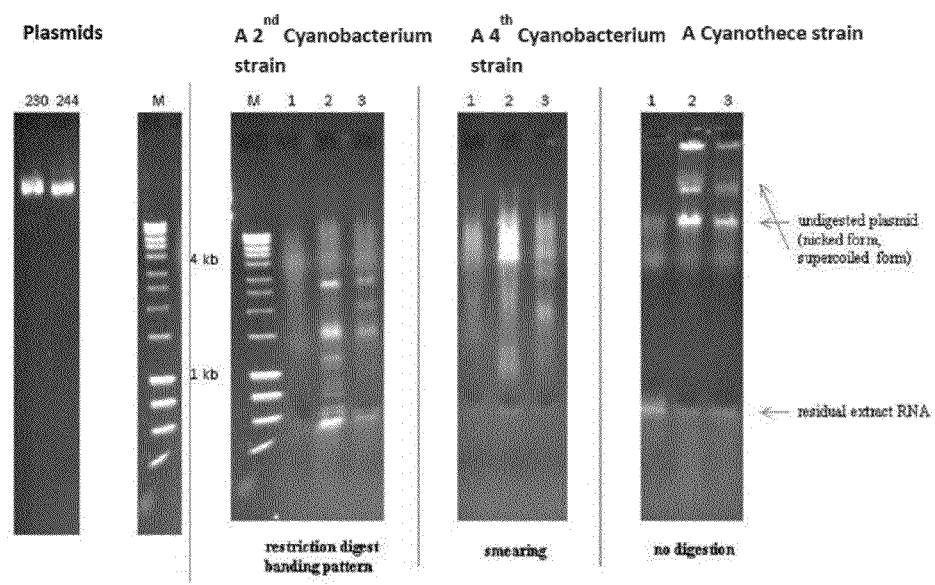
FIG. 5 depicts an agarose gel analysis of the restriction enzyme activity of cyanobacterial extracts on plasmids K230 and K244.

FIG. 5 depicts an analysis of the digestion of plasmids by cyanobacterial extracts. The first panel depicts undigested plasmid K230, undigested plasmid K244, and a marker lane. Moving from left to right, the cyanobacterial extracts used were a fourth *Cyanobacterium* strain, a third *Cyanobacterium* strain, and a *Cyanothece* strain (furthest right panel). For each of the cyanobacterial extract panels, lane M is a size marker, lane 1 is a crude cyanobacterial extract without plasmid addition, lane 2 is plasmid K230 incubated in the extract, and lane 3 is plasmid K244 incubated in the extract. Cyanobacterial extracts were incubated with plasmids K230 and K244 to check for overall restriction activity. A fourth *Cyanobacterium* strain shows a specific digestion banding pattern indicating the presence of one or more restriction endonucleases. A third *Cyanobacterium* strain shows smearing of both plasmids indicating the presence of an unspecific, possibly extracellular, endonuclease or exonuclease that could obscure specific endonucleases that are active at the same time in the same extract upon the same plasmid. Incubation of the plasmids with a *Cyanothece* strain extract depicts the plasmids as being undigested.

Potential Digestions of ROligos

In a first embodiment, a restriction enzyme cuts at the introduced recognition site and thus digests the ROligo into a dual 216/166 bp banding pattern as visualized on an agarose gel stained with ethidium bromide. The dual banding pattern indicates a restriction endonuclease that recognizes the complete introduced site, or part of it.

In a second embodiment, a cellular extract contains an active restriction enzyme that cleaves outside the introduced recognition site of the ROligo. If the cleavage point lies in close vicinity to the introduced restriction site, the resulting band pattern will resemble a double band. However, as the sequences outside the introduced site are identical among all ROligos, cleavage of one ROligo outside of its introduced site would mean that all ROligos would likely be digested and therefore a double band would show up on an agarose gel analysis. This universal digestion of all ROligos is unlikely at least because no more than three restriction endonucleases have been found in any cyanobacterial cellular extract. If a cyanobacterial extract contains an active restriction enzyme that cleaves outside the introduced recognition site of the ROligo, this pattern would indicate that there is at least one restriction enzyme present, but because the enzyme does not specifically cut at the introduced recognition sequence, it cannot be identified by the ROligo method. Deducing its recognition sequence would require other more cumbersome and labor intensive methods such as sequencing the ends of gel-isolated ROligo digestion bands.

In a third embodiment of possible cleavages of ROligos, a restriction endonuclease is present that recognizes an overlap between the introduced restriction site and the bases of the flanking sequences. The introduced recognition site of each ROligo is designed such that no known cyanobacterial enzyme would recognize any overlap created by the insertion of the recognition sequence into the ROligo. If the presence of an additional recognition sequence at the junction site between the flanking regions and the introduced recognition sequence is intrinsically unavoidable, a second, discriminatory, ROligo can be constructed which allows exclusion of one of the possible enzymes. For example, restriction enzyme R.NspI recognizes the overlap between the R.AvaI site and the adjacent flanking arm in the ROligo.AvaIII. Thus, if a ROligo was generated with an R.AvaIII recognition sequence and a double band pattern showed up on the gel, it would not be possible to determine whether the active restriction endonuclease is R.NspI or R.AvaIII by using the ROligo method. However when a second ROligo, ROligo.NspI, is generated where only R.NspI cuts, but not R.AvaIII, the identity of the active restriction enzyme or enzymes can be determined, see, for example, the digestion matrix generated in FIG. 6.

In a fourth and fifth embodiment of possible cleavages of ROligos, a non-double band cleavage pattern or a non-cleavage pattern is generated, respectively. Restriction enzymes that cut an ROligo but do not produce a double band will not be identified by using embodiments of the ROligo method that rely upon the presence of a double band pattern (for example, 216 bp and 166 bp) in the analysis of cellular extract incubated polynucleotides on an agarose gel.

Restriction enzymes that are present in cellular extracts but do not cut any ROligos in the ROligo library will also be missed. This lack of identification of existing, but unknown, restriction endonucleases can be overcome by generating additional ROligos for a ROligo library.

ROligos Containing Degenerate Recognition Sequences

Many cyanobacterial restriction endonucleases have recognition sequences which are degenerate. For example, R.AvaII recognizes GGWCC (where W is A or T) and R.AsuI recognizes GGNCC (where N is A. T, C or G). For the design of a ROligo do distinguish between R.AvaII and R.AsuI using the ROligo method, there are at least two options.

First, degenerate primers can be used to introduce the recognition site into the respective arms. Hence, the ROligo for R.AvaII would contain its two recognized sequences GGACC and GGTCC. Likewise, the ROligo for R.AsuI would contain four sequences, GGACC, GGCCC, GGGCC and GGTCC. The digestion pattern generated using these degenerated ROligos would not be able to distinguish an extract containing R.AvaII from one containing R.AsuI as either enzyme will cut both GGTCC and GGACC containing ROligos to the double band pattern.

In another embodiment, degenerate restriction endonucleases can be distinguished from one another through engineering ROligo recognition sequences of a given ROligo such that fewer of the possible recognition sequences are available to multiple restriction endonucleases. For example, to distinguish between degenerate restriction endonucleases R.AvaII and R.AsuI, GGACC could be used as the sole sequence for the R.AvaII ROligo and GGCCC could be used as the sole sequence for the R.AsuI ROligo. Because GGCCC is not recognized by R.AvaII, extracts with R.AvaII activity can only digest the ROligo.AvaII to the double band pattern but not the ROligo.AsuI, whereas an extract harboring R.AsuI can digest both and therefore the enzymes can be distinguished from one another.

Other examples of identifying degenerate restriction endonucleases include combinations such as R.PvuII having a recognition sequence of CAGCTG and R.NspBII having a recognition sequence of CMGCKG (where M is A or C and K is T or G). In an embodiment, R.PvuII which recognizes CAGCTG and R.NspBII can be distinguished from one another by using CAGCGG as the sole sequence for ROligo.NspBII instead of using all its four sequences recognized, CAGCGG, CAGCTG, CCGCGG, and CCGCTG.

Identification of Restriction Enzymes Using a Digestion Matrix

Infographics can be used to visualize data generated from the analysis of ROligo digestion products in a digestion matrix and to determine the identification of active restriction endonucleases in a cyanobacterial extract through the implementation of various steps of the ROligo method disclosed herein. In an embodiment, a digestion matrix is an infographic table depicting the theoretical capability of various restriction endonucleases as to whether they are capable of digesting the oligonucleotides to a double band pattern. In an embodiment, a digestion matrix can be manipulated through the application of a set of rules to determine the identity of active restriction endonuclease in a cyanobacterial extract. In an embodiment, a digestion matrix is created which depicts the absence or presence of a restriction enzyme in the celhlular extract of a cyanobacterial strain. In an embodiment, the digestion matrix is depicted in the form of an infographic table wherein the rows are labeled with ROligos containing a sequence recognition site and the columns are labeled with known cyanobacterial restriction enzymes. In an embodiment, a digestion matrix depicts, as a filled-in box, which cyanobacterial restriction enzyme(s) would produce a double band digestion pattern (indicative of a digestion of the ROligo at the recognition sequence) for which ROligos, see, for example FIG. 6.

Restriction enzymes that do not share a recognition sequence, degenerate or overlapping, will create a diagonal pattern in a digestion matrix. In a non-limiting sense, ROligos that are digested by only one restriction enzyme are referred to herein as "Optimal ROligos".

If all ROligos were Optimal ROligos, identifying the restriction enzyme constituency of a cellular extract would be a matter of having a comprehensive library of Optimal ROligos encoding recognition sequences for all known restriction enzymes. However, at least because many restriction enzymes exhibit overlap in recognition sequences, R.AvaII/R.AsuI, and R.HaeIII/R.ApaI, for example, additional embodiments of the ROligo method are necessary to identify restriction endonucleases present within various cellular extracts.

Washing Cyanobacterial Cells to Remove Extracellular Nucleases

Figure 7:
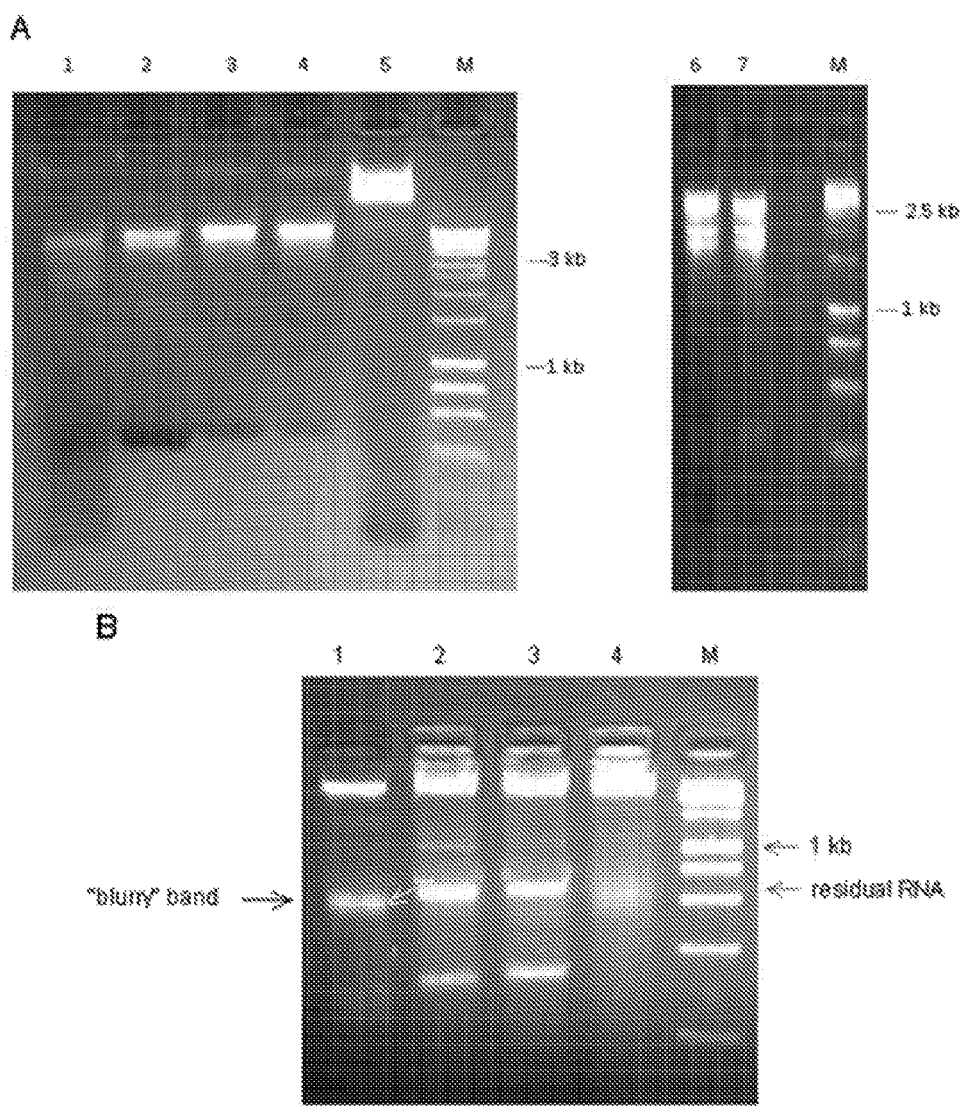
FIG. 7 depicts an agarose gel analysis of the restriction enzyme activity of extracts from Triton or pH/urea treated cyanobacterial cells on plasmids K230, K236Cm, and K244 and a PCR product.
Figure 8:
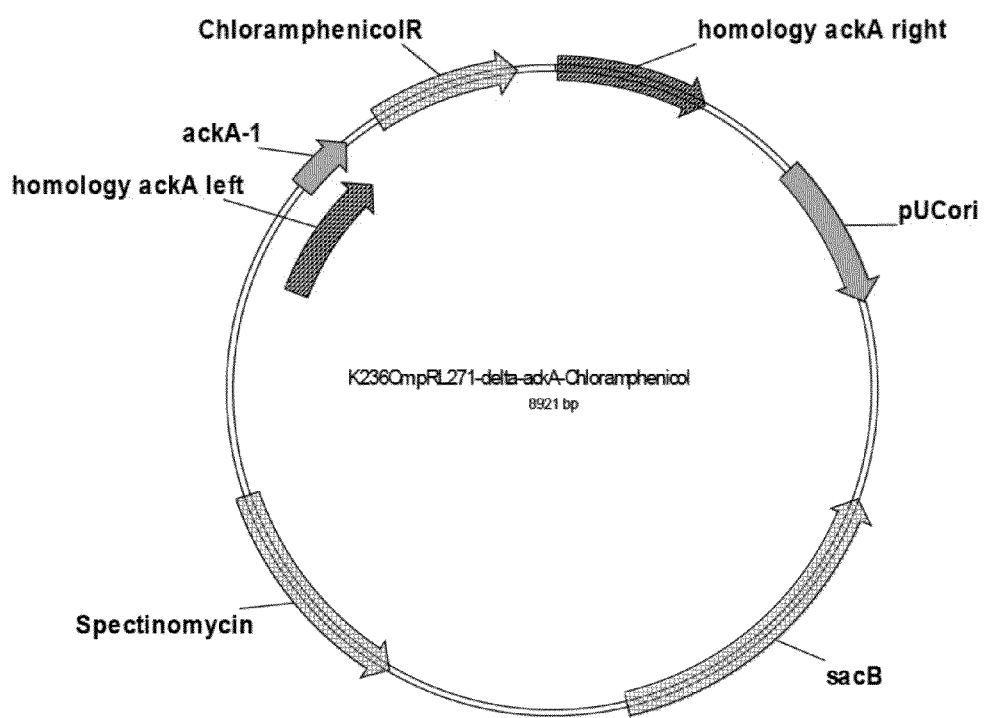
FIG. 8 depicts a plasmid map of K236Cm.
Figure 9:
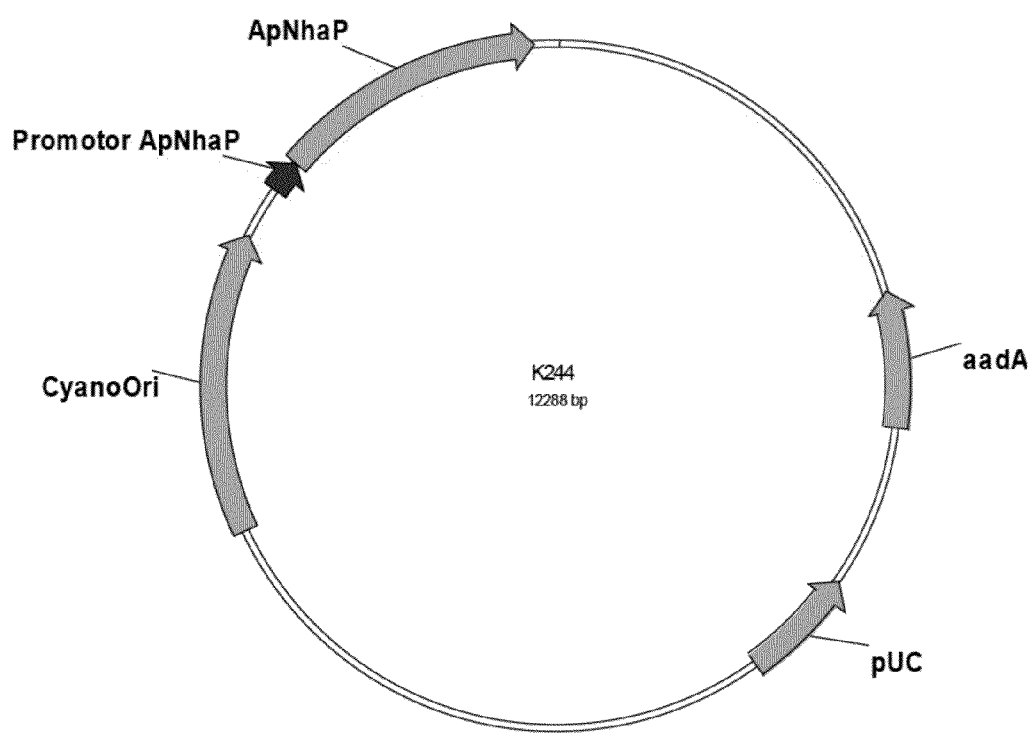
FIG. 9 depicts a plasmid map of K244.

FIG. 7 depicts the results of digestion of plasmids in cyanobacterial extracts that have or have not been washed with either a Triton detergent wash or a pH/urea wash in an attempt to remove extracellular nucleases before disruption of the cyanobacterial cells and testing of their extracts for restriction endonucleases. Plasmids used for digestion include K236Cm (SEQ ID NO: 2) and K244 (SEQ ID NO: 3). Plasmid maps for K236Cm and K244 are depicted in FIG. 8 and FIG. 9, respectively.

Panel A of FIG. 7: Lane 1 is a plasmid mixture of K230, K236Cm and K244 incubated in cell-free medium. Lanes 2-4, are plasmid mixtures incubated with supernatants from respective washing steps with triton solutions. Lane 5 is an unincubated plasmid mixture. Lane M is a size marker. Lane 6 is plasmid K236Cm incubated in a third *Cyanobacterium* strain extract after triton washing at 28° C.; lane 7, plasmid K236Cm incubated in a third *Cyanobacterium* strain extract after triton washing at 37° C.

Cells of a third *Cyanobacterium* strain were washed three times with 0.1% triton in DNase-buffer. A description of the triton washing technique used can be found in Soper, B. W., et. al., J. Bacteriology 1994, 176(17):556-5570. Six hundred nanograms of a plasmid 1:1 mixture containing K230, K236Cm and K244 were incubated over night at 37 OC with the cell's culture media and supernatants. DNA incubated in the cell-free medium (lane 1) showed strong degradation as seen by the smearing towards lower molecular weights and an overall reduction in DNA staining as compared to lanes 3 and 4. DNA incubated in wash supernatant 1 (lane 2) showed weak smearing to lower molecular weights but still a decrease in DNA staining as compared to lanes 3 and 4. DNA incubated in later wash supernatants show only one non-degraded band of similar intensity. The size difference between the unincubated plasmid mixture of lane 5 and the other lanes is likely due to a specific cleavage by an endonucleolytic enzyme which is not removed by triton treatment or a spontaneous reorganization of plasmid DNA during incubation from nicked plasmids to a supercoiled form.

Panel B of FIG. 7: A 1 kb PCR product was used as a template for incubations of DNA with extract from a *Geitlerinema* strain. In lane 1, the template was incubated in crude extract of triton treated cells of a *Geitlerinema* strain incubated overnight at 30° C. In lane 2, the template was incubated overnight at 30° C. in crude extracts of pH/urea washed cells of a *Geitlerinema* strain. In lane 3, the template was incubated overnight at 37° C. in crude extracts of pH/urea washed cells of a *Geitlerinema* strain. Lane 4 depicts a crude extract of pH/urea treated cells from lanes 2 and 3. After triton washing of a *Geitlerinema* strain cells, crude extracts showed unspecific nucleolytic activity (see lane 1) as seen by the blurry band shape after incubating a 1 kb PCR template in a *Geitlerinema* strain extract over night at 30° C. A fresh culture of a *Geitlerinema* strain was then washed with a pH change/urea regimen. As depicted in lane 2, this crude extract did not show smearing of the digestion bands as seen by the sharp bands as visualized. Moreover, incubation at 37° C. did not result in unspecific degradation.

Thus, washing cyanobacterial cells with either a triton or a pH/urea washing regimen was useful for decreasing the amount of non-specific nuclease activity in the cellular extract to be tested for the activity of restriction endonucleases using the ROligo method.

Digestion Matrix of a ROligo Library

Figure 6:
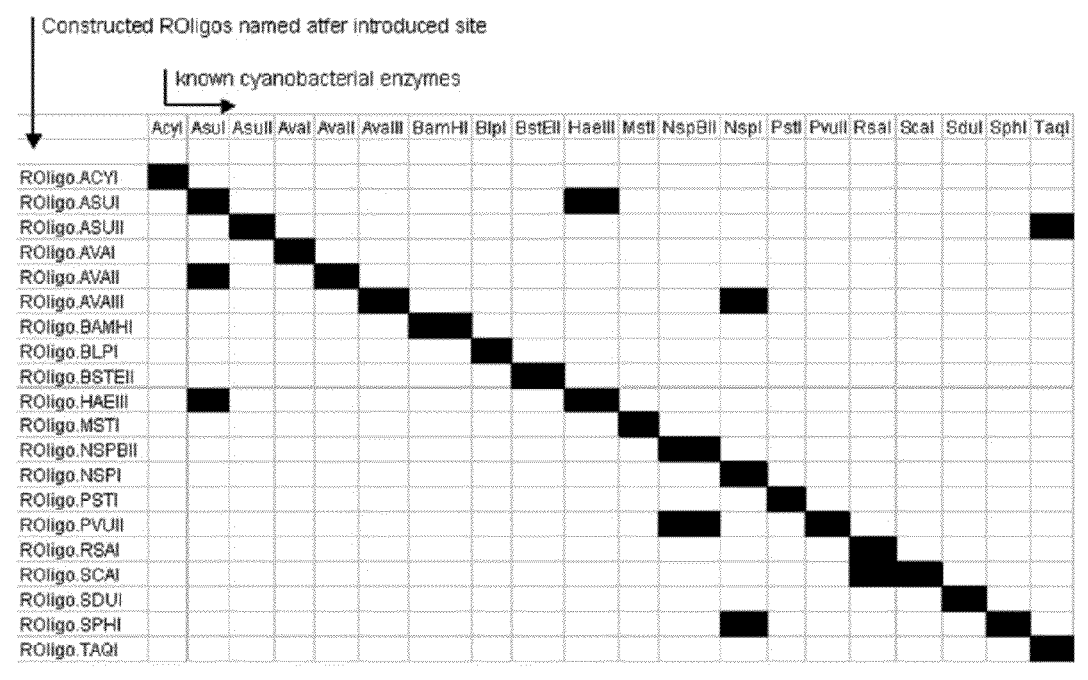

FIG. 6 depicts a predicted digestion matrix of a library of twenty ROligos. Columns are labeled after cyanobacterial enzymes. Rows are labeled after the ROligo. The introduced recognition sequence is reflected by the name of the ROligo. A black box indicates that the enzyme of that column would digest the ROligo of that row to produce a double band of 216/166 bp. Some ROligos not only get cleaved by their specific enzyme, creating the diagonal black box pattern in the matrix, but are also cut by a second or third enzyme recognizing the same sequence, a part thereof or an overlap to the adjacent arm sequence. The digestion of a given ROligo by multiple restriction enzymes can be reduced through careful engineering of the sequence of the recognition site by the addition of surrounding bases. For example, the ROligo.HaeII used to create the digestion matrix of FIG. 6 was engineered without a T base preceding the recognition sequence in an effort to reduce the number of restriction endonucleases that identify the particular ROligo.HaeIII recognition sequence used.

FIG. 6 depicts the theoretical cleavage capability of a set of known cyanobacterial restriction endonucleases to produce the double band pattern on generated ROligos to identify their occurrence in future cyanobacterial extracts. As depicted in FIG. 6, columns are labeled after cyanobacterial restriction enzymes. Rows are named after ROligos. The introduced recognition sequence of the respective restriction endonuclease is reflected by the name of the ROligo. For example, AcyI and ROligo.AcyI. In FIG. 6, a black box indicates that the enzyme of that column can theoretically digest the ROligo of that row to produce a double band of 216 bp and 166 bp as visualized on an agarose gel. Some ROligos not only get cleaved by their respective restriction endonuclease (diagonal black box pattern) but are also cleaved by a second or third enzyme recognizing the same sequence, a part thereof or an overlap to the adjacent arm sequence and thus generating a 216 bp and 166 bp pattern.

After incubation with a cellular extract and analysis by agarose gel, the pattern of digested and undigested ROligos is compared to a predicted digestion matrix to find one enzyme, or a set of enzymes, whose predicted digestion pattern results in exactly the pattern observed. Some incubations result in digestion patterns that predict only one set of enzymes that explain the observed pattern (as the ROligos were designed to be cut by as few other enzymes as possible). However, some combinations of enzymes cannot be distinguished through predicted digestion patterns. For example, the concomitant occurrence of R.HaeIII (recognition sequence of GGCC) and R.AvaII (recognition sequence of GGWCC) would produce the same ROligo digestion pattern as the combination of R.HaeIII and R.AsuI (recognition sequence of GGNCC). This is because R.HaeIII cuts GGCCC and GGGCC, which are the recognition sequences of R.AsuI that are not cleaved by R.AvaII. Thus, using an embodiment of the ROligo method, the concomitant occurrence of R.HaeIII and R.AvaII would be indistinguishable from the concomitant occurrence of R.HaeIII and R.AsuI. Other embodiments of the ROligo method and rules of interpretation of digestion patterns are useful to distinguish concomitant occurrences of restriction endonucleases such as these.

Exemplary Rules Used in Embodiments of the ROligo Method

In an embodiment of the ROligo method, a sequence of rules can be applied to identify a set of restriction endonucleases that explain an observed ROligo digestion pattern as depicted in a digestion matrix.

Rule 1: First, all restriction endonucleases which theoretically do not recognize and cleave at least one of the ROligos that are observed to be cleaved to the double band pattern by a cellular extract are discarded (removed from being included in the digestion matrix). The digestion matrix then only contains enzymes that can theoretically cut at least one of the observably digested ROligos.

Rule 2: Secondly, restriction endonucleases which theoretically recognize and cleave a ROligo that does not show a double band pattern after extract incubation, can be discarded from the digestion matrix.

Rule 3: The occurrence of the remaining restriction endonucleases then explains the observed pattern of digested and non-digested ROligos. Generally, all restriction endonucleases remaining in the digestion matrix after the application of rules 1 and 2 are needed to actually explain the pattern.

However, in some instances, a pattern is present that may be explained by either one enzyme or a combination of restriction endonucleases being responsible for the digestion of multiple ROligos. The digestion pattern presents itself as ambiguous as to whether it is the combination of restriction endonucleases or the single restriction endonuclease is responsible for the observed ROligo digestions. As an example, the ROligo digestion pattern of both R.NspBII (CMGCKG recognition sequence wherein M is A or C, and K is G or T) and R.PvuII having a CAGCTG recognition sequence, is identical to the one produced by R.NspBII alone. The same reasoning applies to the combination of R.AsuI having a GGNCC recognition sequence plus R.AvaII having a GGWCC recognition sequence, and R.AsuI alone. In these ambiguous patterns, the existence of the single restriction enzyme that is responsible for digesting the two ROligos is chosen to exist versus the presence of two restriction endonucleases that perform the identical function. Not being limited by theory, a single restriction endonuclease is more likely to occur in the extract because a cell evolves to conserve metabolic resources and thus would not develop an increase in protection against foreign DNA by expressing two restriction endonucleases where the expression of a single restriction endonuclease would provide the same number and type of recognition sites as the two restriction endonucleases combined. Thus, the restriction endonuclease exhibiting the broader cleavage range is considered more likely to exist alone in the cellular extract and is kept as a restriction endonuclease that exists while the combination of restriction endonucleases are discarded if they cannot be individually eliminated.

Identifying Restriction Endonucleases in a Cyanobacterial Extract Using the ROligo Method Using a ROligo library of the twenty ROligos depicted in FIG. 6, active restriction endonucleases from a first *Cyanobacterium* strain extract were determined. The incubation of the ROligos from the ROligo library with the cellular extract was performed in a two-step process. First, five pools of four ROligos were incubated with a cellular extract and a double band digestion pattern was tested for. Second, the individual ROligos comprising the ROligo pool showing a double band digestion pattern were each individually incubated with the cellular extract and analyzed for the double band digestion pattern.

Figure 10:
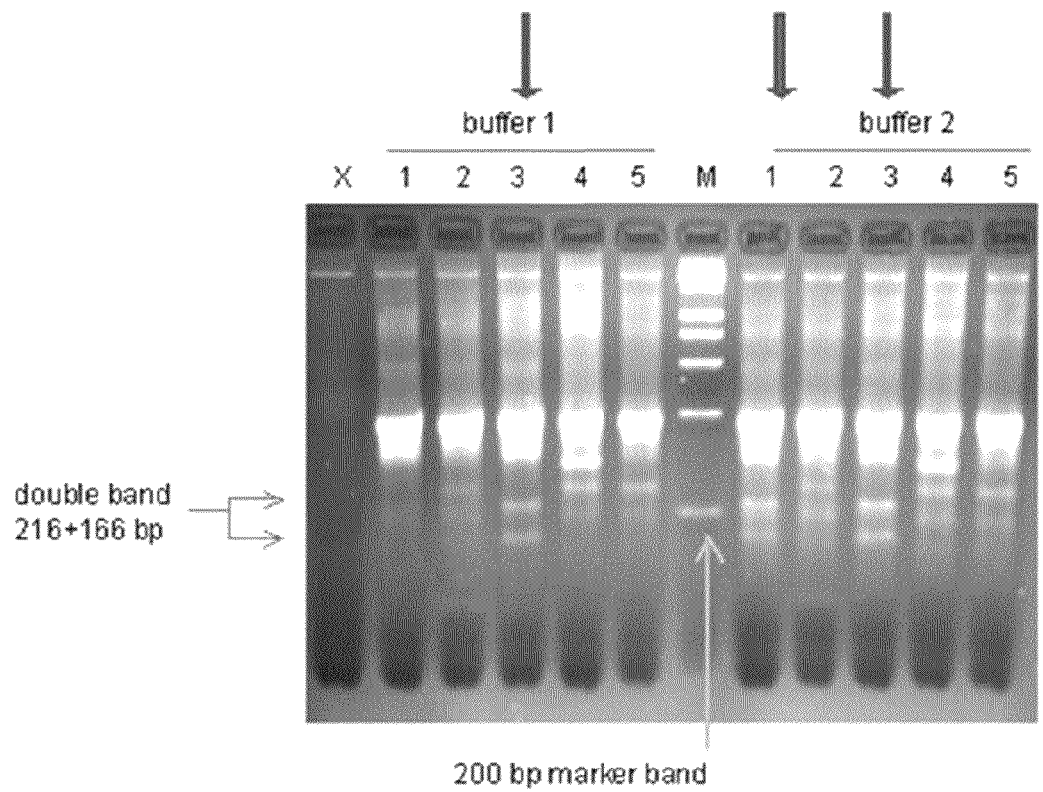
FIG. 10 depicts an agarose gel analysis of the restriction enzyme activity in an extract from a first *Cyanobacterium* strain upon various ROligo pools.

FIG. 10 depicts the results of an ethidium bromide stained agarose gel analysis of several pools of ROligos incubated in a first *Cyanobacterium* strain extract. Lanes 1-5, together, comprise the totality of a ROligo library of 20 ROligos. Each lane has four ROligos (a ROligo pool) from the ROligo library. Each ROligo pool is incubated in either a NEB buffer P1 (left part of the gel) and buffer P2 (right part). The most commonly used NEB buffers P1, P2, P3, and P4 are designed such that most known restriction endonucleases will be active in at least one of the four buffers. Lane X is a first *Cyanobacterium* strain extract without addition of ROligos. Lane M is a size marker.

Some pools of ROligos show a digestion double band at around 216/166 bp (marked by arrows at the top). Pool 1 showed a double band only in buffer P2 but not in buffer P1, pool 3 showed a double band in both P1 and P2 buffers. Not depicted are the incubations performed in NEB buffers P3 and P4. Because pools 2, 4, and 5 showed no double band digestion pattern, their constituent ROligos were eliminated as possibly existing in this first *Cyanobacterium* strain.

Figure 11:
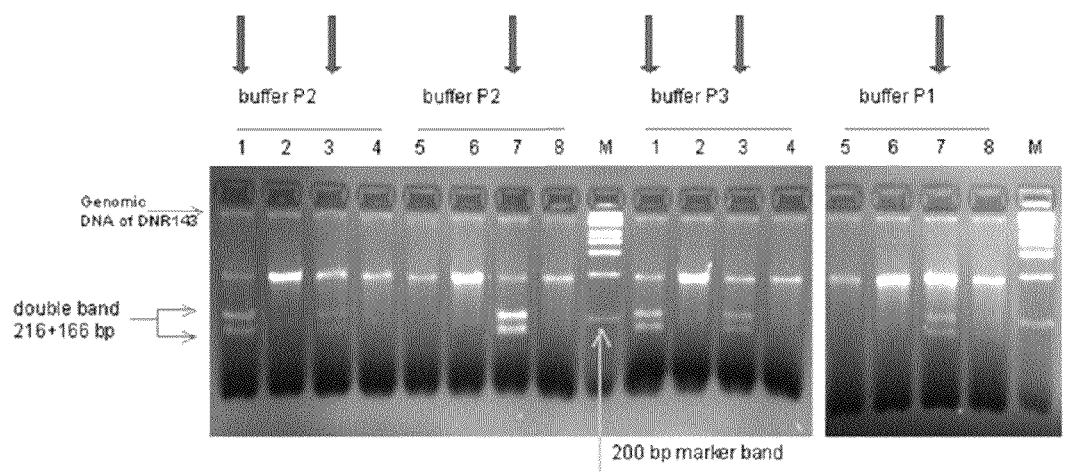
FIG. 11 depicts an agarose gel analysis of the restriction enzyme activity in an extract from a first a first *Cyanobacterium* strain upon ROligo.AsuI, ROligo.AvaII, ROligo.HaeII, ROligo.SduI, ROligo.AvaIII, ROligo.NspI, ROligo.SphI, and ROligo.BamHI.

FIG. 11 depicts the results of incubation of individual ROligos in a first *Cyanobacterium* strain extract. Individual ROligos comprising ROligo pools that resulted in a double band pattern after the first-step incubation, see FIG. 10, were each individually incubated in a first *Cyanobacterium* strain extract in NEB buffers P1, P2 or P3. Lanes 1-8 depict the results of ROligos incubated in a first *Cyanobacterium* strain extract as follows: Lane 1 is ROligo.AsuI having a recognition site of GGNCC constructed as GGCCC. Lane 2 is ROligo.AvaII. Lane 3 is ROligo.HaeIII constructed as GGCC. Lane 4 is ROligo.SduI. Lane 5 is ROligo.AvaII. Lane 6 is ROligo.NspI. Lane 7 is ROligo.SphI constructed as GCATGC. Lane 8 is ROligo.BamHI. Lane M is a marker. ROligos showing a double band were ROligo.AsuI, ROligo.HaeIII and ROligo.SphI and are marked with arrows.

Combining four ROligos in one incubation reaction as a first step in the ROligo method reduces work load significantly as compared to incubating each member of the ROligo library individually. As exemplified above, to identify which of the twenty analyzed cyanobacterial restriction enzymes are present in a first *Cyanobacterium*, strain, the twenty ROligos in the digestion matrix (see FIG. 6) were sorted in a way that ROligos that were digested by the extract, those showing a double banding pattern, were moved to the top of the matrix (see FIG. 12, top three rows). Rule 1 was then applied to the digestion matrix, and all enzymes which theoretically cannot cut at least one of these three ROligos were removed, leaving four possible enzymes, R.AsuI, R.HaeIII, R.NspI and R.SphI, see FIG. 13. Applying rule 2 (restriction enzymes which theoretically would also digest at least one other ROligo to the double band pattern than the observed extract-digested double band pattern showing ROligos can be discarded) allowed to discard enzymes R.AsuI (as ROligo.AvaII was undigested) and R.NspI (as neither ROligo.NspI nor ROligo.AvaIII was digested by the extract, see FIG. 14.

This left two enzymes, R.HaeIII and R.SphI. R.HaeIII theoretically cuts ROligo.AsuI and ROligo.HaeIII. R.SphI only cuts its own ROligo.SphI. The occurrence of both these enzymes in the digestion matrix produces the same pattern (see FIG. 14) as was observed in a first *Cyanobacterium* strain extract, see FIG. 15. Thus, through using an embodiment of the ROligo method, the active restriction endonucleases in a first *Cyanobacterium* strain extract were determined and subsequent vectors and constructs used for transformation of a first *Cyanobacterium* strain extract can be engineered to lack those recognition sequences or can be methylated at those recognition sequences to prevent digestion of the vector by the endogenous restriction endonucleases of a first *Cyanobacterium* strain.

Analyses of Endonuclease Activity in Cyanobacterial Strains Using the ROligo Method FIG. 15 depicts various cyanobacterial strains that were analyzed with an embodiment of the ROligo method to identify restriction nuclease activity therein. If a genomic sequence of the cyanobacterial strain was available, RM ("R"estriction "M"odification) systems were predicted. RM systems were identified when a gene encoding a restriction enzyme and a gene encoding its cognate methyltransferase are present in close genomic proximity. Examples of some of the tested methylation of ROligos that blocks the respective cyanobacterial restriction endonucleases from cleavage are given.

As depicted in FIG. 15, the asterisk (*) denotes that the recognition sequence of a given restriction endonuclease contains two GC stretches. In most cases, both GC stretches were methylated by the methyltransferase M.CviPI. In a prophetic embodiment, restriction enzymes in the respective strain extracts are blocked by methylation of one or both of the GC stretches.

As depicted in FIG. 15, the pound sign (#) denotes enzymes that were previously not known to exist in cyanobacteria and were identified by using the sequencing method. The identified restriction endonuclease's activities were verified by using the ROligos method to identify restriction endonucleases.

As depicted in FIG. 15, the double pound sign (##) denotes an enzyme that was initially detected by cloning and sequencing digestion bands.

In an embodiment, and as depicted in FIG. 15, the restriction endonucleases in extracts of fifteen cyanobacterial strains were analyzed by the ROligo method. Genomic analysis of strains, whose genome had been sequenced, predicted restriction enzymes in a second *Lyngbya* strain, a *Chlorogloeopsis* strain, a second *Cyanobacterium* strain, and a second *Nostoc* strain, see FIG. 15. With the exception of a second *Nostoc* strain, all enzymes whose activity could be demonstrated in crude extracts using the ROligo method, see FIG. 15, were also predicted by in silico methods. However, not all predicted enzymes were found active in extracts, see a second *Nostoc* strain in FIG. 15, for example.

A hitherto unknown cyanobacterial restriction enzyme was detected in a third *Cyanobacterium* strain. Incubation with a third *Cyanobacterium* strain extract showed digestion of plasmids, but none of the ROligos in the library were digested to a double band. Direct sequencing of the ends of the digested plasmid bands revealed a region of about 30 bp where the sequences all showed a signal drop, indicating the possible presence of extracellular nucleases slowly and possibly non-specifically degrading the ends of the digested plasmids. In an effort to remove any extracellular nucleases, the cells were washed with a triton washing protocol as described herein. Analyzing possible restriction enzymes that would have a recognition sequence within that region and further limiting to palindromic enzymes (almost all cyanobacterial restriction endonucleases have recognition sequences that are palindromatic), the recognition sequence of five candidate restriction enzymes were identified and ROligos were constructed accordingly. Of the five candidate restriction enzymes, only the ROligo.EcoRV, having a recognition sequence of R.EcoRV (GATATC), was found to be digested by the extract, see FIG. 15, and R.EcoRV was the only enzyme that could digest the ROligo to the double band as judged by the appropriate digestion matrix. Because R.EcoRV was not previously known to be a cyanobacterial restriction endonuclease, if a plasmid devoid of EcoRV sites had been incubated with the cellular extract, this restriction enzyme would not have been detected. A *Geitlerinema* strain was analyzed as well. Again, none of the ROligos in the library at the time of analysis was digested to a double band. However incubating plasmid K230 and several PCR products derived from it, clearly showed digestion. After sequencing the ends of a digested PCR product, a SauI recognition sequence of CCTNAGG was detected and the corresponding ROligo was constructed and was digested by a *Geitlerinema* strain extract.

In a prophetic embodiment, and according to an embodiment of the ROligo method, the generated ROligo.EcoRV, and ROligo.SauI corresponding to the restriction endonucleases identified could then be methylated by appropriate means. The methylated ROligos could then be incubated with the appropriate cyanobacterial extracts and could be analyzed to determine to what degree digestion was inhibited by their respective restriction endonucleases.

Figure 12:
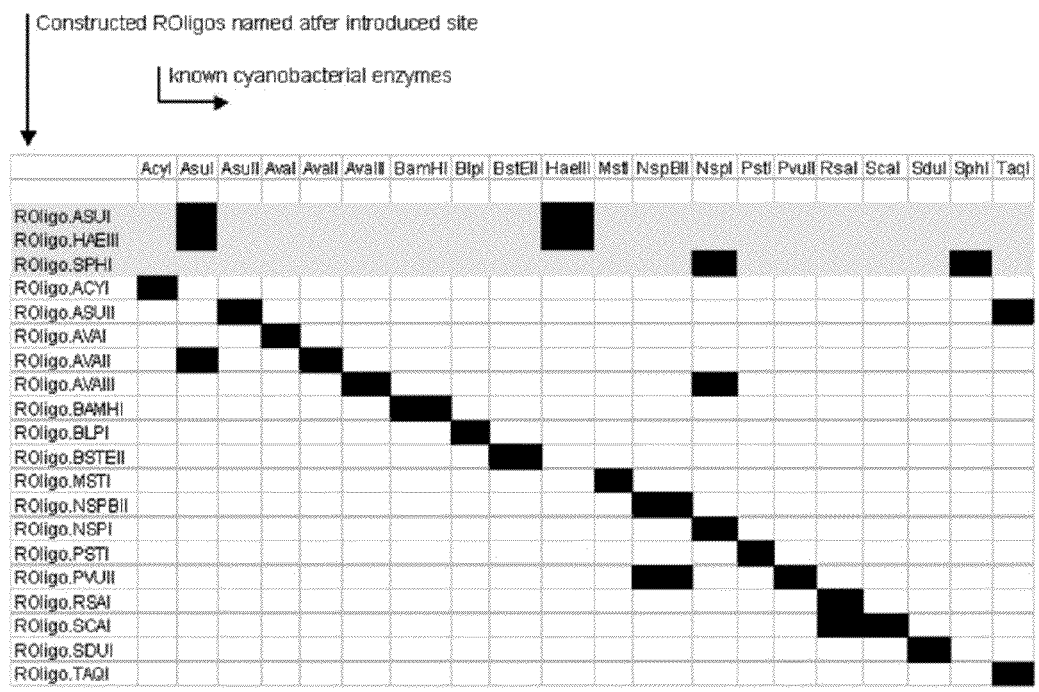
FIG. 12 is an infographic chart depicting the results of incubation of various ROligos as a step in the exemplification of the ROligos method for identifying restriction enzymes in a first *Cyanobacterium* strain extracts.

FIGS. 12-14 depict and embodiment of the ROligo method used to determine the restriction enzymes that are active in an extract of a first *Cyanobacterium* strain.

In an embodiment of the ROligo method, FIG. 12 depicts a digestion matrix that is a useful for the identification of a first *Cyanobacterium* strain's restriction enzymes. A digestion matrix of a library of twenty ROligos was reorganized to reflect the observed pattern of digested and undigested (i.e., double band digestion of a ROligo detected or not) ROligos in a first *Cyanobacterium* strain extract. The top most three ROligos (rows) marked yellow, are digested by a first *Cyanobacterium* strain extract, the unmarked ROligos are not.

FIG. 13 depicts a digestion matrix of a first *Cyanobacterium* strain extract incubated ROligos after applying an embodiment of rule 1 of the ROligo method (removal of any enzyme which does not cut at least one of the three topmost ROligos). Rule 2 (restriction enzymes which theoretically would recognize other ROligos than the ones having been observed to be extract-digested to the double band pattern, can be discarded) was applied to discriminate the R.AsuI/ROligo.AvaI I digestions (black horizontal arrow) and the R.NspI/ROligo.AvaIII digestions.

FIG. 14 depicts a digestion matrix resulting from the incubation of a ROligo library in a first *Cyanobacterium* strain extract after applying rules 1 and 2 and then applying rule 3 (the occurrence of the remaining enzymes then explains the observed pattern of digested and non-digested ROligos). The combination of the activity of the two remaining enzymes, R.HaeIII and R.SphI, cut exactly those ROligos which are digested by the extract.

Therefore, in an embodiment of the ROligo method, FIGS. 12-14 depict steps of the ROligo method used to identify the active restriction endonucleases of a cyanobacterial strain. Thus, vectors for transformation of the cyanobacterial strain can be designed that lack the recognition sequences of R.HaeIII and R.SphI and therefore increase the likelihood of transformation of the cyanobacterial strain for which the ROligo method has been performed upon.

Generation of New Digestion Matrices

In an embodiment, after generating new ROligos, the starting digestion matrix will be constructed anew, and would now include any newly identified ROligos and incorporate the predicted digestion pattern of the newly identified ROligos into a new digestion matrix. The restriction enzymes included in the matrix (showing the double band pattern) can be derived from various sets of enzymes, e.g. all cyanobacterial enzymes, all palindromic enzymes, or all restriction enzymes present, for example, in databases such as REBASE.

DNA Methylation

DNA methylation is the process of transferring a methyl group from a donor molecule to either a cytosine or an adenine by DNA methyltransferases. Three types of methylated bases are predominantly found in DNA: 5-methylcytosine (m5C), N4-methylcytosine (m4C), and N6-methyladenine (m6A). The organism-specific pattern of methylation depends on the methyltransferases' specificity.

In prokaryotes, DNA cleavage by a cognate restriction enzyme is prevented by the methylation of DNA by a sequence-specific methyltransferase which is an integral component of every restriction-modification system. *E. coli* strains used for propagation of plasmid DNA often contain a site-specific DNA adenine methyltransferase, Dam. The methylase encoded by the dam gene methylates the N6-position of an adenine residue within the GATC sequence.

Most restriction enzymes are sensitive to DNA methylation. When a restriction enzyme recognition sequence overlaps a methylation site, no effect, a partial inhibition or complete block of digestion may occur. Furthermore, the ability to cleave methylated DNA is an intrinsic and unpredictable property of each restriction enzyme. Therefore, isoschizomers and neoschizomers which recognize the same DNA sequences can differ in their sensitivity to DNA methylation. To prevent DNA digestion of heterologous vectors, both the type of DNA methylation and the sensitivity of the restriction enzyme to that type of methylation should be considered.

Methylation Sensitivity of Identified Restriction Endonucleases

In an embodiment, the ROligo method is used to improve the efficiency of determining the methylation sensitivity of identified restriction endonucleases. Methylation sensitivity usually has to be checked for each restriction enzyme found and cannot be inferred from a recognition sequence alone. As an example, the non-cyanobacterial restriction enzymes R.DpnI, R.MboI and R.Sau3AI all recognize the four base pair palindrome sequence of GATC. However, they show different sensitivity to methylation of GATC at the adenine or cytosine position (see REBASE). R.DpnI only cuts fully adenine methylated Gm6ATC. MboI is blocked by hemi-methylation at Gm6ATC but is not affected by C5-cytosine methylation. Sau3AI cuts both N6-adenine methylated and unmethylated DNA, but is blocked by C5-methylation GATm5C.

Different types of in vitro methylation can be used to methylate a ROligo. The effect of methylation can subsequently be checked by incubation of the methylated ROligo in an extract that cuts the non-methylated ROligo. If a suitable methylation type that protects from cleavage has been identified, methyltransferase databases like REBASE can be searched for a known methyltransferase that catalyzes that type of methylation. If these methyltransferases can subsequently be expressed in yeast or *E. coli*, the sequencing of the cyanobacterial genome to find endogenous methyltransferases is not necessary.

Methylation of ROligos

Identification of restriction endonucleases that are present in a given strain of cyanobacteria allows for site specific methylation of heterologous DNA prior to transformation of that given strain of cyanobacteria. In an embodiment, methylation of ROligos can be achieved by heterologous overexpression of methyltransferases. For example, plasmids that overexpress methyltransferases, such as M.AvaI and M.AvaII methyltransferases, may be constructed and used in an *E. coli* donor strain and then transferred into a cyanobacterial strain via conjugation (see Elhai J., et. al., J. Bacteriology 1997, 179(6):1998-2005) or other transformation means.

In another embodiment, commercially available methyltransferases can be used to methylate ROligos. Methylation success is checked by restriction digestion with a corresponding commercially available restriction enzyme that is blocked by the type of methylation used (which can be found for example in charts depicting methylation sites for known restriction endonucleases, e.g., REBASE). Any methylations that result in protection of the ROligos from digestion can then be applied to methylate plasmids or other exogenous DNA prior to transformation of cyanobacterial strains having the identified restriction endonuclease activity. For example, M.CviPI methylates cytosine at the C5 position in its GC recognition sequence. M.SssI methylates cytosine at the C5 position in its CG recognition sequence. M.CviPI or M.SssI, for example, can therefore be used to methylate DNA at cytosines. Many of the cyanobacterial enzymes contain a CG or GC stretch and can, therefore, be checked for their sensitivity to m5CG and/or Gm5C methylation, see FIG. 2. As an example, protection from digestion of ethanologenic plasmids and ROligos methylated by M.CviPI and M.SssI from restriction endonucleases is depicted in FIG. 16.

Figure 16:
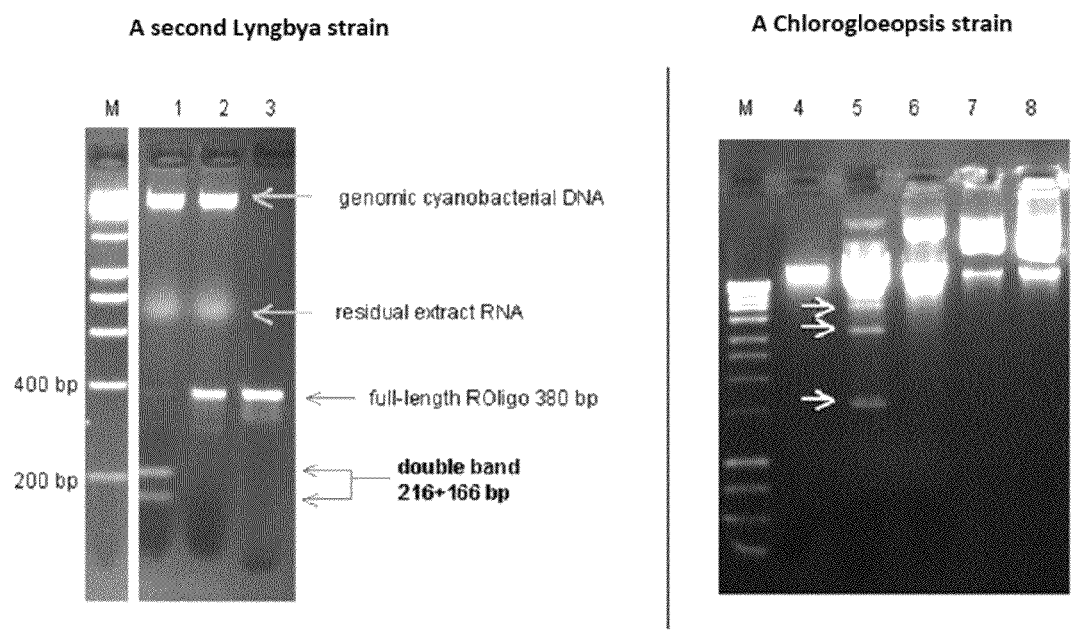
FIG. 16 depicts an agarose gel analysis of Gm5C-methylated ROligo.PvuII or TK18 plasmid incubated with a first *Lyngbya* strain and a *Chlorogloeopsis* strain extract.

FIG. 16 depicts analysis of a possible protective effect of Gm5C-methylation against a first *Lyngbya* strain extract and a *Chlorogloeopsis* strain extract. The left panel of FIG. 16 depicts lane M which is a reference marker; lane 1 which is an unmethylated ROligo.PvuII incubated in a first *Lyngbya* strain extract; lane 2 which is Gm5C-methylated ROligo.PvuII incubated in a first *Lyngbya* strain extract; and lane 3 which is methylated ROligo.PvuII that has not been digested. Thus, as depicted in the left panel of FIG. 16, ROligo.PvuII, having a recognition sequence of CAGCTG was methylated using commercially available M.CviPI which methylates the cytosine at the C5 position in its recognition sequence GC resulting in CAGm5CTG. Methylated and unmethylated ROligo.PvuII were incubated in a first *Lyngbya* strain extract and only the umnethylated ROligo.PvuII was digested by the extract. Thus, R.PvuII activity in a first *Lyngbya* strain is blocked by M.CviPI methylation. Therefore, the left panel of FIG. 8 depicts the protective effect of methylation of ROligo.PvuII against digestion from a restriction endonuclease in the extract of a first *Lyngbya* strain.

Figure 17:
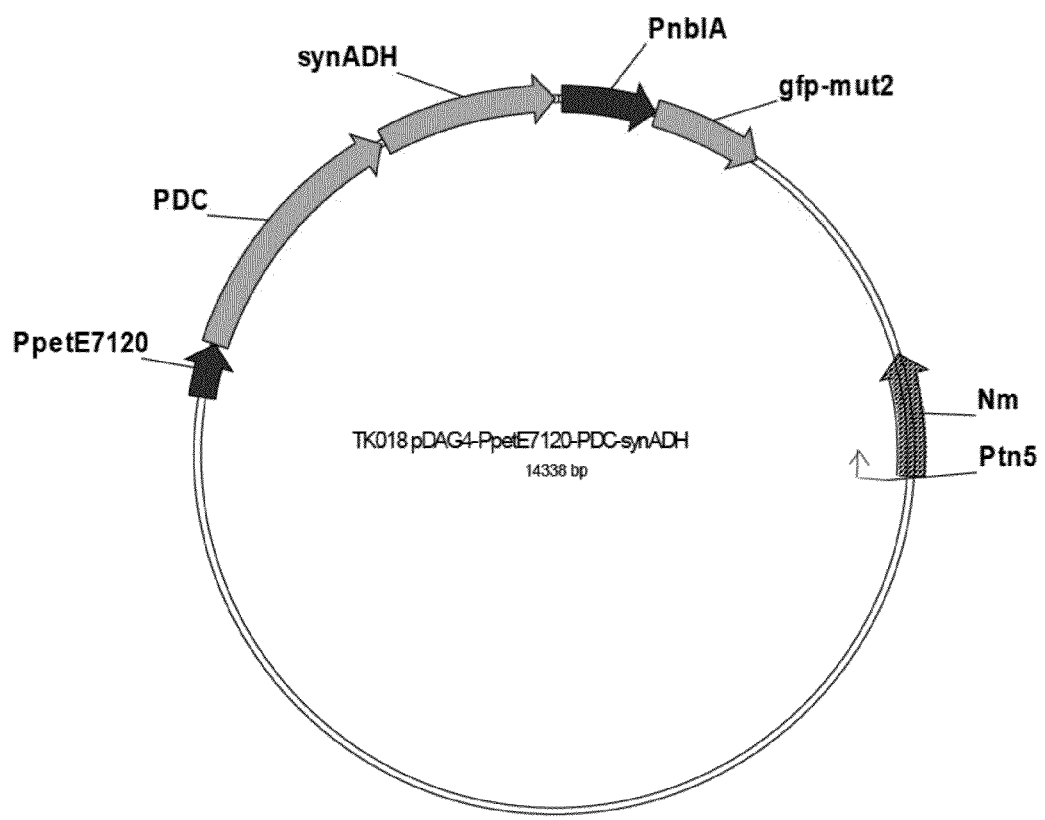
FIG. 17 depicts a plasmid map of TK018.

The right panel of FIG. 16 depicts analysis of a possible protective effect of Gm5C-methylation against a *Chlorogloeopsis* strain extract. TK018 (SEQ ID NO: 4), an exemplary plasmid containing an ethanologenic cassette, was methylated with M.CviPI and then column purified. A plasmid map of TK018 is depicted in FIG. 17. Methylated and unmethylated TK018 were then incubated in a *Chlorogloeopsis* strain extract. The right panel of FIG. 16 depicts lane M which is a size marker; lane 4 which is a *Chlorogloeopsis* strain extract without DNA; lane 5 which is TK18 incubated in a *Chlorogloeopsis* strain extract; lane 6 which is TK18 methylated with M.CviPI and then incubated in a *Chlorogloeopsis* strain extract; lane 7 which is unincubated TK018; and lane 8 which is methylated TK18 that has not been incubated. As depicted in the right panel of FIG. 16, the methylated plasmid in lane 6 does not show the digestion bands of the unmethylated plasmid of lane 5. Therefore, the right panel of FIG. 16 depicts the protective effect of methylation of an exemplary plasmid, TK018, against digestion from a restriction endonuclease in the extract of a *Chlorogloeopsis* strain.

Figure 18:
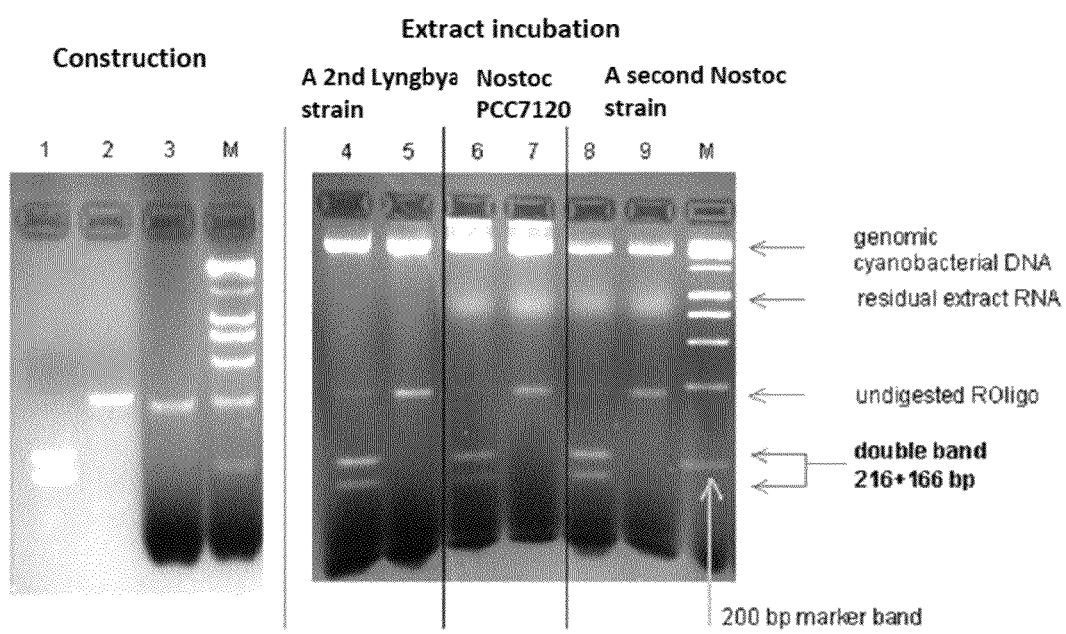
FIG. 18 depicts an agarose gel analysis of methylated (by a DNA-free *Escherichia coli* extract harbouring a plasmid expressing M.AvaII methyltransferase) and unmethylated ROligo.AvaII in various cyanobacterial extracts.

In yet another embodiment, the extract from *E. coli* strains containing methyltransferases expressed from helper plasmids can be used to methylate ROligos. FIG. 18 depicts the protective effect of M.AvaII methylation of ROligo.AvaII against digestion from restriction endonucleases within the extracts of a first *Lyngbya* strain, a first *Nostoc* strain, and a second *Nostoc* strain. As depicted in FIG. 18, lane 1 is an unmethylated ROligo.AvaII digested with commercially available R.AvaII; lane 2 is a methylated ROligo.AvaII subjected to digestion with R.AvaII; lane 3 is a methylated ROligo.AvaII that is undigested; lanes 4, 6, and 8 are unmethylated ROligo.AvaII incubated in extract of a first *Lyngbya* strain, a first *Nostoc* strain, and a second *Nostoc* strain, respectively; lanes 5, 7, and 9 are methylated ROligo.AvaII incubated in extract of a first *Lyngbya* strain, a first *Nostoc* strain, and a second *Nostoc* strain, respectively; and lane M is a reference marker.

ROligo.AvaII as used in FIG. 18 incubations was, as applicable, methylated using an extract from *E. coli* HB101 containing a M.AvaII expressing plasmid pRL528. Success of methylation of ROligo.AvaI was verified by digesting the methylated ROligo.AvaII with commercially available and methylation sensitive R.AvaII, see lanes 1 and 2 of FIG. 18. The methylated and unmethylated ROligo.AvaII were incubated in extracts of a first *Lyngbya* strain, a first *Nostoc* strain and a second *Nostoc* strain which all demonstrated R.AvaII activity, see lanes 4, 6 and 8 of FIG. 18. R.AvaII activity in all strains depicted in FIG. 18 is blocked by M.AvaII methylation; compare lanes 4 to 5, 6 to 7, and 8 to 9 of FIG. 18.

In another embodiment, endogenous *E. coli* Dam methyltransferase from a DNA free extract of *E. coli* can be used to methylate ROligos and plasmids. Effects of methylation by an endogenous *E. coli* Dam methyltransferase can be analyzed by using an *E. coli* extract to methylate ROligos. ROligos complimentary to restriction enzymes that contain a GATC site, such as R.BglII with a recognition site of AGATCT or R.BamHI with a recognition site of GGATCC, can be methylated and tested for protection against digestion.

In another embodiment, methylated nucleotides could be incorporated into ROligos by PCR. For recognition sites which cannot be methylated by in vitro methyltransferases, PCR could be used to incorporate methylated nucleotides. This method could be especially useful when there is no commercial enzyme available which methylates any given position in a restriction enzyme recognition sequence.

Additional Means of Identification of Unknown Restriction Endonucleases

Restriction endonucleases that do not recognize a ROligo from an existing ROligo library will not be identified. Thus, increasing the number of ROligos in a ROligo library will increase the number of potentially identifiable restriction enzymes.

In an embodiment, a method of identifying unidentified, cyanobacterial, restriction endonucleases is to generate a sequence that contains recognition sequences for restriction enzymes which are currently unknown in cyanobacteria. Thus, in a prophetic example, a sequence could be constructed in silico that contains recognition sequences of all known restriction enzymes in a database, e.g., REBASE, except for cyanobacterial recognition sequences or recognition sequences that are cleaved by cyanobacterial enzymes. For example, the cyanobacterial R.HaeIII has a recognition sequence of GGCC and also cuts the recognition sequence of the non-cyanobacterial restriction endonuclease R.NotI having a recognition sequence of GCGGCCGC. Therefore, the recognition sequence of R.NotI would be omitted.

After construction of the polynucleotide sequence containing all of the appropriate recognition sequences, the sequence would be incubated with cyanobacterial extracts. If the sequence was digested, the resulting band(s) would be isolated from a gel and directly sequenced with primers spanning the artificial sequence. This sequencing information would provide the recognition sequence and also the identity of the restriction enzyme active in the cyanobacterial extract. Thus, this prophetic embodiment would allow for the detection and identification of new enzymes currently not described in cyanobacteria.

In a prophetic embodiment, restriction endonucleases that cleave outside of the recognition sequence of a given ROligo could be detected through construction of a "megaROligo". Detecting a double band cleavage product of a ROligo digested at the recognition site can be obfuscated when two restriction enzymes occur in one cyanobacterial extract, each digesting the ROligo. The restriction activity of both of the restriction endonucleases acting upon the ROligo at, for example, the recognition sequence and at a site in one of the flanking regions would result in a digestion pattern different from the predicted double band digestion product indicative of a single digestion at the recognition sequence by the correlating restriction endonuclease.

To account for restriction endonucleases that cut within a flanking arm of a given ROligo, a megaROligo could be constructed. The megaROligo would contain a recognition sequence that contains all recognition sequences that occur within the flanking arms that are used in the construction of the ROligos in a ROligo library. Consistent with the design principles of ROligos, this multiple recognition sequence would be flanked by an artificial sequence that is devoid of any recognition sequences from any known restriction enzymes.

In a prophetic embodiment, pre-incubation of this megaROligo in cyanobacterial extracts would allow testing for the presence of restriction endonucleases that recognize sequences in the flanking arms of all ROligos in the library. Thus, by incubating the megaROligo in the extract of cyanobacterial cells to be analyzed by the ROligo method, multiple restriction enzymes that digest a given ROligo and obscure the double band pattern expected by only digestion at the recognition sequence could be detected. This detection of multiple restriction enzymes digesting a ROligo in parallel would provide an additional quantum of information useful for determining the full complement of restriction endonucleases in a cyanobacterial extract.

In a prophetic example, to avoid digestion of ROligos in flanking regions ROligos could be engineered to be devoid of any recognition sequences in the flanking regions for any known restriction endonucleases.

All currently identified cyanobacterial enzymes except R.MboII are palindromic. Therefore, in a prophetic example, a "polypalindromic" sequence could be constructed that contains all possible palindromic sequences from 4-8 bp in length that are not recognized by any known restriction enzymes. In a prophetic embodiment, incubating this polypalindromic sequence in a cyanobacterial extract could identify novel restriction enzymes from cyanobacteria.

Labeled Roligos

In a prophetic embodiment, ROligos could be labeled with fluorescent dyes, radiolabels, antigens or other labels. The labels could be incorporated through post-labeling techniques or could be incorporated using pre-labeled nucleotides through polynucleotide synthetic techniques well known in the art, see for example oligonucleotide synthetic services available through Iba life sciences in Olivette, Mo. at http://www.iba-lifesciences.com/Service Custom oligos.html and Shibata A., Molecules 2012 Feb. 29; 17(3):2446-63 which discloses various techniques and references to techniques well known in the art of oligonucleotide labeling.

In an embodiment, the labels used on each individual ROligo in a given ROligo pool would be uniquely identifiable. As an example, if a ROligo pool contained four different ROligos, each could be labeled with a dye that fluoresces at a wavelength that is different from the other three labels. Thus, even if multiple ROligos were digested and they all created digestion bands that were indistinguishable from one another on an ethidium bromide stained agarose gel, the identity of the double bands present could be visualized by measuring fluorescence at the four different wavelengths at which the four dyes fluoresce. For example, four different ROligos, ROligo.MstI, ROligo.SduI, ROligo.BlpI, and ROligo.BsteII could each be respectively labeled at a flanking region with a blue, green, yellow and red fluorescing dye. If a dual band pattern was visualized, one could not a priori determine which of the four ROligos had been digested. However, if the bands were then measured for fluorescence and a blue and red fluorescence were detected, the restriction enzymes of R.MstI and R.BsteII would have been identified. This multi-dimensional measurement would eliminate the additional step of runnming each of the ROligos individually from a ROligo pool that demonstrated a dual band pattern via ethidium bromide visualization on an agarose gel.

In another prophetic embodiment, as many different labels as there are ROligos in a library could individually be incorporated into an individual ROligo. Thus, if there were twenty ROligos in a ROligo library, there could be twenty different labels that are visualized by twenty distinct wavelengths, antibody-antigen bindings or other visualization means. In this prophetic embodiment, all twenty ROligos could be incubated in a cellular extract. The entire extract would then be run in a single lane on an agarose gel and the digestion bands present would be measured according to the twenty different visualization means.

Universal Methyltransferases

In a prophetic embodiment, *E. coli* strains are used to express cyanobacterial methyltransferases, e.g., M.SphI, M.BlpI, and M.AsuI from a *Chlorogloeopsis* strain, M.AcyI from a second *Cyanobacterium* strain and M.PvuI from a second *Lyngbya* strain. Activity of the expressed methyltransferases will then be analyzed in crude *E. coli* extracts similar to those depicted in FIG. 16. The expressed methyltransferases will be analyzed for methylation and transformation efficiency. The effects that the expressed methyltransferases have on the resistance of ROligos to digestion and to transformation efficiency of methylated vectors in a cyanobacterial strain will also be compared to 2 bp-methyltransferases such as M.CviPI and M.SssI.

M.CviPI and M.SssI lead to hypermethylation of DNA while cyanobacterial methyltransferases methylate DNA at specific recognition sites. Hypermethylation could result in difficulty of the initial replication of plasmids in cyanobacteria and/or for the expression of a resistance marker. However, hypermethylation would not be maintained during replication as newly synthesized strands of DNA would be subject to only methylation by the endogenous methyltransferases which may or may not be able to act upon hemi-hypermethylated double stranded DNA.

Transformation success in a *Chlorogloeopsis* strain was increased by M.CviPI hypermethylation of a vector used for transformation. The cloned cyanobacterial methyltransferases that were used to methylate the vector used for transformation of a *Chlorogloeopsis* strain could also be used to check for their effect on digestion of vectors in different strains with the corresponding restriction enzyme.

Digestion by most of the identified cyanobacterial restriction endonucleases can be protected against by a combination of M.CviPI, M.SssI and M.AvaII. Thus, in a prophetic embodiment, a "universal" helper plasmid would be constructed wherein M.CviPI, M.SssI and M.AvaII methyltransferases are expressed. This universal helper plasmid could be used to help increase the transformation efficiency of many different vectors into various cyanobacterial strains.

EXAMPLES

Triton Washing of Cyanobacterial Cells

Cyanobacterial cells were washed three times with DNase-buffer (40 mM TRIS pH 7.4, 6 mM magnesium chloride, 2 mM calcium chloride) supplemented with 0.1% (v/v) triton X-100. After a final wash step with lysis buffer, cells were disrupted with glass beads. Cell-free medium (supplemented with DNase buffer) and cell-free supernatants after each wash step were incubated with about 300 ng to about 900 ng plasmid overnight at about 28° C. to account for the activity of unspecific nucleases.

Washing of Cyanobacterial Cells Using Buffers with pH Changes and Urea Supplementation Cyanobacterial cells were washed two to three times with alternating buffers of acidic and basic pH (acidic buffer: 20 mM potassium phosphate pH 3 supplemented with 1 M urea; basic buffer: 20 mM potassium phosphate pH 11 supplemented with 1 M urea). Urea was used to destabilize proteins and expose amino acids. By rapidly changing the pH, a permanent denaturation of proteins might result and render unspecific nucleases ineffective at digestion. Finally, cells were washed twice with lysis buffer and disrupted with glass beads. The cell-free supernatant was used as the crude extract.

Preparation of Cyanobacterial Extracts

From a liquid preculture, 50 mL of a given cyanobacterial strain was inoculated to an $OD_{750}$ of between 0.5 to 1.0. After 10 days, 30 mL of that culture was pelleted (5 min 3000×g at room temperature), washed once with lysis buffer (40 mM sodium hydrogenphosphate pH 7.4, 1 mM EDTA, 5% (v/v) glycerol) and resuspended in 1 mL lysis buffer with 1 U RNaseI. Cells were disrupted with glass beads in a tissue lyser. The cell debris was removed by two consecutive centrifugation steps for each 5 min at 14000×g at room temperature. The final supernatant was used as crude extract.

Construction of ROligos

Examples of PCR primers used to generate various left arms and right arms of various ROligos can be found in FIG. 3. The left arm, approximately a 170 bp fragment, was amplified using K230 (FIG. 1) as a template and DreamTaq polymerase (35 cycles of (1 min at 95° C., 1 min at 59° C., 1 min at 72° C.) with forward primer #474 (see FIG. 3) and a reverse primer containing the site to be introduced. Similarly, the right arm, approximately a 210 bp fragment, was amplified with a forward primer containing the site to be introduced and thus was overlapping with the reverse primer of the respective left arm and a reverse primer #475. Both arms were gel isolated and used in a 1:20 dilution in an overlapping PCR with booster primers #472 and #473 (3'-truncated versions of primers #474 and #475) that resulted in a approximately 380 bp fragment, which was gel isolated and quantitatively amplified using primers #474 and #475 again and a proofreading polymerase, Pwo, with 250 µM dNTP each, 250 nM each primer, 2 U Pwo/100 µL reaction, 1.5 mM $MgSO_4$ and 35 cycles of (94° C. 15 sec, 63° C. 30 sec, 45 sec at 68° C.). ROligos were then checked by digesting with commercially available restriction enzymes to verify correct insertion.

Incubation of Plasmids with Crude Extract

Plasmid DNA was incubated in cyanobacterial extracts over night at 28° C. with up to 30 µg protein (with the extract volume comprising up to about 25% (v/v) of the total reaction volume) in NEB buffer P4. To test for restriction endonuclease activity, a 40 µL reaction with 600 ng plasmid was loaded directly onto a 0.8% (w/v) agarose gel. For direct sequencing, 2 µg of plasmidial DNA were digested and then column purified, for example.

Determination of Restriction Endonucleases in a Cyanobacterial Crude Extract

A cyanobacterial extract was incubated with a mixture of four different ROligos, a "ROligo pool". Each constituent ROligo was added to the pool at 150 ng overnight at 28° C. with 25% (v/v) extract, in NEB buffers P1, P2, P3 and P4 (compositions thereof are well known in the art and can be found at REBASE or ordered from New England Biolabs) and analyzed on a 2% (w/v) agarose gel. Pool/buffer combinations, where a double band at 216/166 bp was observed were further analyzed by incubating the individual ROligos separately in the respective buffer overnight. The resulting pattern of digested, i.e., showing a double band of 216/166 bp, and non-digested ROligos in a given extract was evaluated using a digestion matrix and restriction endonucleases were identified accordingly.

Methylation of ROligos

Identification of restriction endonucleases that are present in a given strain of cyanobacteria allows for site specific methylation of heterologous DNA prior to transformation. Methylation of ROligos was achieved through using the following protocol: 1 µg ROligo was methylated in a buffer containing 40 mM potassium phosphate buffer at pH 8.0 (or TRIS), 10 mM DTT, 25 mM EDTA supplemented with 640 µM S-adenosylmethionine (SAM) and a suitable methyltransferase. Methyltransferases were used at either 50 µL of an *E. coli* extract containing suitable methyltransferases or commercially available methyltransferases such as M.CviPI or M.SssI at about 0.5 to 2 U per µg DNA to be methylated. The final volume for the methylation reaction was 200 µL. The methylation reaction proceeded overnight at 37° C. Afterwards, the ROligo was column purified. Methylation success was checked by restriction digestion with an appropriate, commercially available restriction enzyme that is blocked by the type of methylation used (which can be found in charts depicting methylation sites for known restriction endonucleases, see REBASE). Methylation events that prevented the methylated ROligos from digestion by cyanobacterial extracts can then be applied to methylate heterologous plasmids prior to transformation into a given cyanobacterial strain.

Preparation of an *E. coli* Extract with Methyltransferase Activity

To methylate using the endogenous *E. coli* Dam methyltransferase, an extract of *E. coli* alphaSelect (available from Bioline USA Inc. of Taunton Mass.) was grown for 2 days at room temperature in 1% (w/v) soy bean peptone/0.5% (w/v) yeast extract was used (the final extract volume was 1/100 of the initial culture volume). Cells were disrupted in lysis buffer as above for cyanobacterial extracts. To methylate using the M.AvaII methyltransferase, *E. coli* HB101 harboring the pRL528 plasmid (Elhai, J, et. al, J. Bacteriology 1997, 179 (6):1998-2005) grown for 2 days was used. *E. coli* extracts were DNaseI-treated (2 U per ml extract volume) for 30 min at 37° C. after supplementation with DNaseI buffer (NEB). The DNA-free extract was then used to methylate ROligos.

Sequencing of Extract-Digested Plasmids

Figure 19:
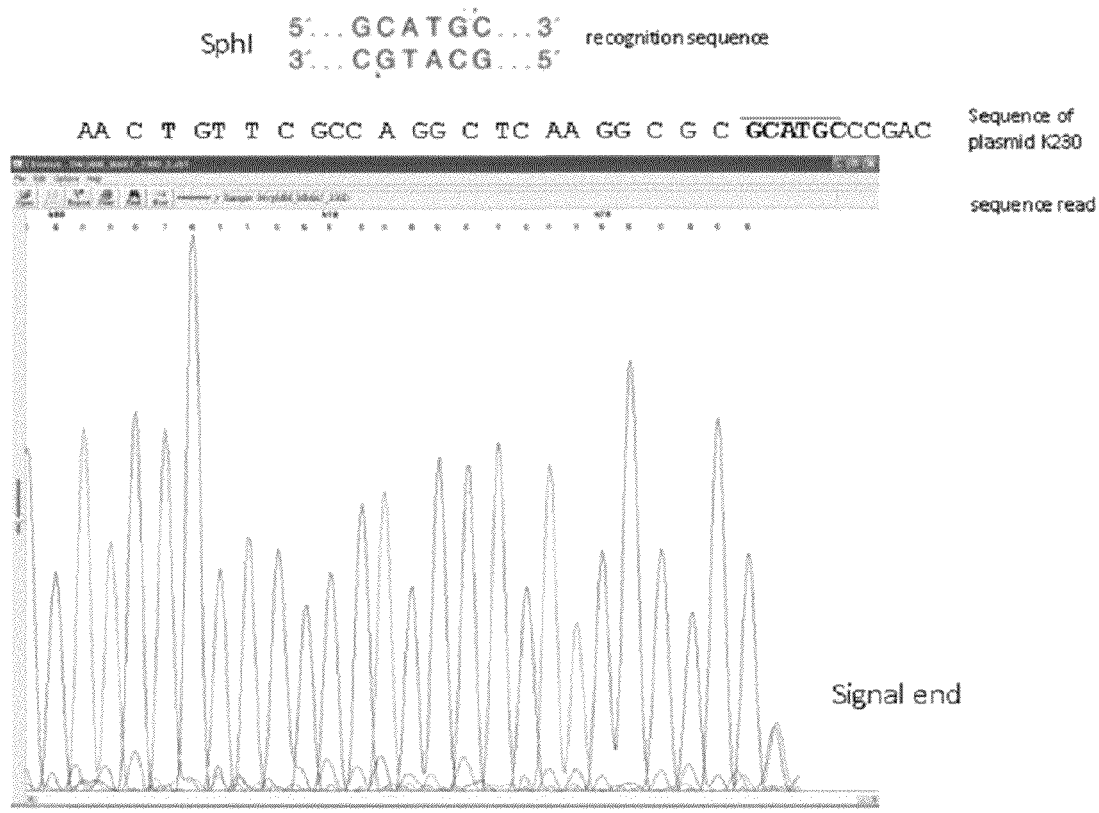
FIG. 19 depicts a sequencing readout of a plasmid K230 digested in a *Chlorogloeopsis* strain extract.

A cyanobacterial-extract digested plasmid was sequenced after column purification with a variety of sequencing primers that span the whole plasmid in about 1 kb distances between adjacent primers. A cleavage point was identified when the sequencing signal drops sharply, see FIG. 19, for example. A recognition site around a given cleavage point was then identified and thus the corresponding restriction endonuclease was identified.

Other Embodiments

A number of embodiments of the disclosure have been described. Nevertheless, it will be understood that various modifications may be made without departing from the spirit and scope of the disclosure. Such modifications will become apparent to those skilled in the art from a consideration of this disclosure or practice of the disclosure disclosed herein. Consequently, it is not intended that this disclosure be limited to the specific embodiments disclosed herein, but that it cover all modifications and alternatives coming within the true scope and spirit of the disclosure as embodied in the attached claims.

The invention claimed is:

1. A method for identifying restriction endonucleases in a cyanobacterial cell comprising:
   a) incubating oligonucleotides from a ROligo library with a cyanobacterial cell extract from said cyanobacterial cell, wherein each oligonucleotide comprises recognition sequence of a cyanobacterial restriction endonuclease, and
   b) analyzing digestion products of said oligonucleotides for digestion at said recognition sequences, and
   c) identifying restriction endonucleases in said cyanobacterial cell extract by analyzing digestion products of said oligonucleotides.

2. The method of claim 1 wherein said cyanobacterial cell is selected from the group consisting of *Prochlorococcus*, *Synechocystis*, *Synechococcus*, *Chroococcales*, *Cyanobium*, *Oscillatoriales*, *Cyanobacterium*, *Pleurocapsales*, *Geitierinerna*, *Phormidium*, *Euhalothece*, *Anabaena*, *Lyngbya*, *Spirulina*, *Nostoc*, *Pleurocapsa*, and *Leptolyngbya*.

3. The method of claim 1 wherein said restriction endonucleases of step c) are analyzed through depicting the results of digestion patterns at recognition sequences of said oligonucleotides from a ROligo library in an infographic table comprising all incubated oligonucleotides and all restriction endonucleases whose recognition sequences are part of said oligonucleotides, and wherein restriction endonucleases are identified from said cyanobacterial cell extract through the following stepwise manipulations of said digestion patterns depicted in said infographic table:
   a) first, removing from said infographic table restriction endonucleases which do not digest at least one of said oligonucleotides incubated with said cyanobacterial cell extract and
   b) second, removing from said infoqraphic table restriction endonucleases that would be ca able of digesting an oligonucleotide from said ROligo library other than oligonucleotides in the digestion products that are digested b the extract at recognition sequences of the restriction endonucleases, and
   c) third, identifying restriction endonucleases in said cyanobacterial extract as the restriction endonucleases not removed from said infographic table.

4. The method of claim 3 wherein said infographic table is a digestion matrix.

5. The method of claim 3 wherein said each oligonucleotide comprises a left arm, a right arm, and a recognition sequence for a cyanobacterial restriction endonuclease wherein said oligonucleotide is produced through using a polymerase chain reaction wherein said left arm is a double stranded polynucleotide and said right arm is a double stranded polynucleotide and wherein the 5' end of a single stranded reverse primer of said left arm and the 5' end of a single stranded forward primer of the right arm overlap and comprise a recognition sequence for a cyanobacterial restriction endonuclease and wherein said left arm and said right arm primers use a template lacking any recognition sites for cyanobacterial restriction endonucleases.

6. The method of claim 5 wherein said recognition sequence is positioned asymmetrically along the length of said each oligonucleotide such that digestion by said restriction endonuclease creates two digestion products of different sizes.

7. The method of claim 6 wherein said template is base pairs 7550 to 7926 of SEQ ID NO: 1 and wherein said left arm primer and said right arm primer comprise single stranded polynucleotide primers selected from the group consisting of SEQ ID NOs: 5-62.

* * * * *